(12) United States Patent
Chi et al.

(10) Patent No.: US 9,896,467 B1
(45) Date of Patent: Feb. 20, 2018

(54) ORGANIC COMPOUND WITH TETRAHEDRAL-LIKE GEOMETRY

(71) Applicant: National Tsing Hua University, Hsinchu (TW)

(72) Inventors: Yun Chi, Hsinchu (TW); Yang Wang, Fujian Province (CN); Han-Yan Tsai, Kaohsiung (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/467,940

(22) Filed: Mar. 23, 2017

(30) Foreign Application Priority Data

Dec. 7, 2016 (TW) .............................. 105140354 A

(51) Int. Cl.
| | |
|---|---|
| *C07D 487/04* | (2006.01) |
| *C07D 491/20* | (2006.01) |
| *C07D 495/20* | (2006.01) |
| *C07D 487/20* | (2006.01) |
| *C07F 9/6561* | (2006.01) |

(52) U.S. Cl.
CPC .......... *C07F 9/6561* (2013.01); *C07D 487/04* (2013.01); *C07D 487/20* (2013.01); *C07D 491/20* (2013.01); *C07D 495/20* (2013.01)

(58) Field of Classification Search
CPC ... C07F 9/6561; C07D 487/04; C07D 487/20; C07D 491/20; C07D 495/20
USPC ....................................................... 544/60
See application file for complete search history.

(56) References Cited

U.S. PATENT DOCUMENTS

| | | |
|---|---|---|
| 2015/0060808 A1 | 3/2015 | Kim et al. |
| 2015/0228915 A1 | 8/2015 | Cho et al. |
| 2015/0311440 A1 | 10/2015 | Seok et al. |

FOREIGN PATENT DOCUMENTS

| | | |
|---|---|---|
| CN | 104513245 | 4/2015 |
| CN | 103848967 | 1/2016 |
| TW | I318210 | 12/2009 |
| TW | 201538478 | 10/2015 |

OTHER PUBLICATIONS

Renata Marcia de Figueiredo, Synthesis (2007), (4), 529-540.*
"Office Action of Taiwan Counterpart Application," dated Aug. 16, 2017, p. 1-p. 6.

* cited by examiner

*Primary Examiner* — Kahsay Habte
(74) *Attorney, Agent, or Firm* — J.C. Patents

(57) ABSTRACT

An organic compound with a tetrahedral-like geometry is disclosed. The organic compound has a structure represented by formula (I):

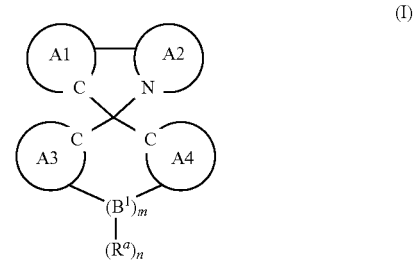

wherein A1 to A4 each independently represent a 5-membered or 6-membered unsaturated ring; $B^1$ represents direct bonding, —C—, —O—, —N—, —S— or —C=C—; m is 0 or 1; each of $R^a$'s is independently hydrogen, fluorine, oxygen, substituted or unsubstituted $C_1$-$C_{12}$ alkyl or substituted or unsubstituted $C_6$-$C_{12}$ aryl; and n is an integer of 0 to 2.

9 Claims, 6 Drawing Sheets

ORGANIC COMPOUND WITH TETRAHEDRAL-LIKE GEOMETRY

CROSS-REFERENCE TO RELATED APPLICATION

This application claims the priority benefit of Taiwan application serial no. 105140354, filed on Dec. 7, 2016. The entirety of the above-mentioned patent application is hereby incorporated by reference herein and made a part of this specification.

BACKGROUND OF THE INVENTION

1. Field of the Invention

The invention is related to an organic compound, and particularly related to an organic compound with a tetrahedral-like geometry or a spiro-arrangement.

2. Description of Related Art

A solar cell is a device that converts sunlight into electrical energy. The use of solar cells for power generation is a renewable environmental-friendly power generation method, greenhouse gases such as carbon dioxide are not produced during power generation, and therefore, the environment is not polluted. On the contrary, an organic light-emitting diode is an environmental lighting and photoelectric display device that converts electrical energy into light. The energy loss during the light-emitting process is low, so the negative impact to the environment is low as well.

The hole transporting material for a solar cell and the electron transporting material for an organic light-emitting diode play important roles in energy conversion efficiency of photoelectric devices. Therefore, the development of hole or electron transporting material is a matter of great concern to those skilled in the art. The conventional organic hole and electron transporting materials have a symmetrical configuration, and their energy conversion efficiency is poor when applied to a solar cell and an organic light-emitting diode. Therefore, the industry expectation cannot be met.

SUMMARY OF THE INVENTION

Accordingly, the invention provides an organic compound with a tetrahedral-like geometry (or spiro-arrangement) that has excellent photophysical properties.

The invention provides an organic compound with a tetrahedral-like geometry that has a structure represented by formula (I):

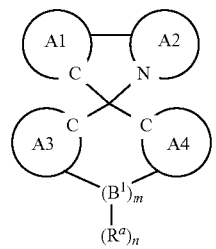

(I)

wherein A1 to A4 each independently represent a 5-membered or 6-membered unsaturated ring; $B^1$ represents direct bonding, —C—, —O—, —N—, —S— or —C=C—; m is 0 or 1; each of $R^a$'s is independently hydrogen, fluorine, oxygen, substituted or unsubstituted $C_1$-$C_{12}$ alkyl or substituted or unsubstituted $C_6$-$C_{12}$ aryl; and n is an integer of 0 to 2.

In an embodiment, A1 is a 6-membered unsaturated ring, A2 is a 5-membered unsaturated ring, and a structure of A3 and a structure of A4 are substantially identical.

In an embodiment, the organic compound has a structure represented by the following formula (IA):

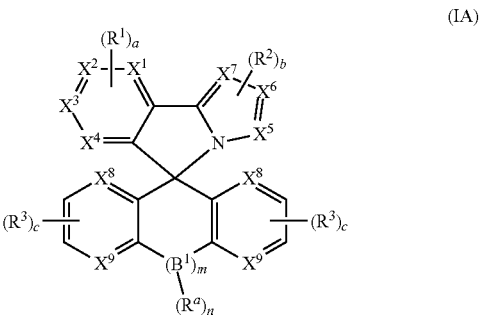

(IA)

wherein $X^1$ to $X^9$ are each independently carbon or nitrogen; each of $R^1$'s and $R^2$'s is independently hydrogen, substituted or unsubstituted $C_1$-$C_{12}$ alkyl, substituted or unsubstituted $C_1$-$C_6$ alkoxy, substituted or unsubstituted $C_6$-$C_{12}$ aryl or —$C_yF_{2y+1}$, y is an integer of 0 to 3; a is an integer of 0 to 4; b is an integer of 0 to 3; each of $R^3$'s is independently hydrogen, halogen, cyano, substituted or unsubstituted $C_1$-$C_{12}$ alkyl, substituted or unsubstituted $C_1$-$C_6$ alkoxy, substituted or unsubstituted $C_6$-$C_{12}$ aryl, substituted or unsubstituted amino or substituted or unsubstituted phosphinyl; c is an integer of 0 to 4; when c is equal to or greater than 1, each of $R^3$'s can be the same or different; $B^1$ represents direct bonding, —C—, —O—, —N—, —S— or —C=C—; m is 0 or 1; each of $R^a$'s is independently hydrogen, fluorine, oxygen, substituted or unsubstituted $C_1$-$C_2$ alkyl or substituted or unsubstituted $C_6$-$C_{12}$ aryl; and n is an integer of 0 to 2.

In an embodiment, the organic compound has a structure represented by the following formula (IA-a):

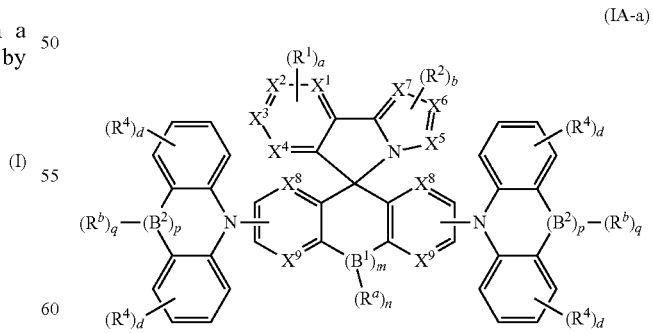

(IA-a)

wherein each of $R^4$'s is independently hydrogen, fluorine, substituted or unsubstituted $C_1$-$C_{12}$ alkyl, substituted or unsubstituted $C_1$-$C_6$ alkoxy or substituted or unsubstituted $C_6$-$C_{12}$ aryl; d is an integer of 0 to 4; when d is equal to or greater than 1, each of $R^4$'s can be the same or different, and two or more $R^4$'s can joint to form a $C_3$-$C_8$ aromatic ring; $B^2$ represents —O—, —S—, —C— or —N—; p is 0 or 1; each of $R^b$'s is independently hydrogen, fluorine, substituted or unsubstituted $C_1$-$C_{12}$ alkyl; and q is an integer of 0 to 2. The organic compound with a tetrahedral-like geometry of the invention has an excellent hole transporting property. When such organic compound is applied to the production of the photoelectric device, excellent energy conversion efficiency can be provided, and a high application value can be achieved.

In an embodiment, the organic compound has a structure represented by the following formula (IA-b):

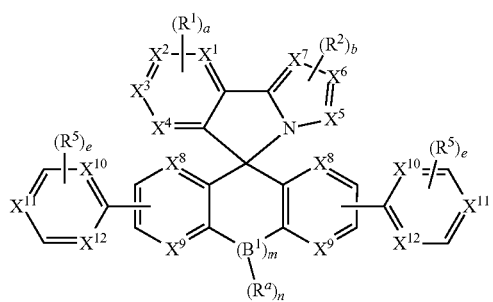

(IA-b)

wherein $X^{10}$ to $X^{12}$ are each independently carbon or nitrogen; each $X^{10}$ can be the same or different; each $X^{11}$ can be the same or different; each $X^{12}$ can be the same or different; each of $R^5$'s is independently hydrogen, fluorine, substituted or unsubstituted $C_1$-$C_{12}$ alkyl, substituted or unsubstituted $C_1$-$C_6$ alkoxy or substituted or unsubstituted $C_6$-$C_{12}$ aryl; e is an integer of 0 to 5; and when e is equal to or greater than 1, each of $R^5$'s can be the same or different. The organic compound with a tetrahedral-like geometry mentioned in the invention has an excellent electron transporting property.

When such organic compound is applied to the production of the photoelectric device, excellent energy conversion efficiency can be provided, and a high application value can be achieved.

In an embodiment, the organic compound has a structure represented by the following formula (IA-c):

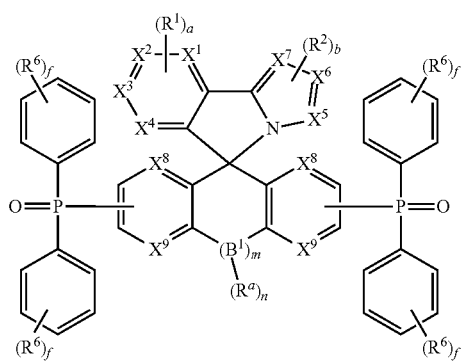

(IA-c)

wherein each of $R^6$'s is independently hydrogen, fluorine, substituted or unsubstituted $C_1$-$C_{12}$ alkyl, substituted or unsubstituted $C_1$-$C_6$ alkoxy or substituted or unsubstituted $C_6$-$C_{12}$ aryl; f is an integer of 0 to 5; and when f is equal to or greater than 1, each of $R^6$'s can be the same or different.

In an embodiment, at least one of $X^1$ to $X^4$ is nitrogen.

Based on the above, in the organic compound of the invention, at least one C—N bond replaces the conventional C—C bond, so that the organic compound of the invention has an asymmetry tetrahedral-like geometry. The organic compound with a tetrahedral-like geometry of the invention has excellent photophysical properties. When such organic compound is applied to the production of the photoelectric device, excellent energy conversion efficiency can be provided, and a high application value can be achieved.

To make the above features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
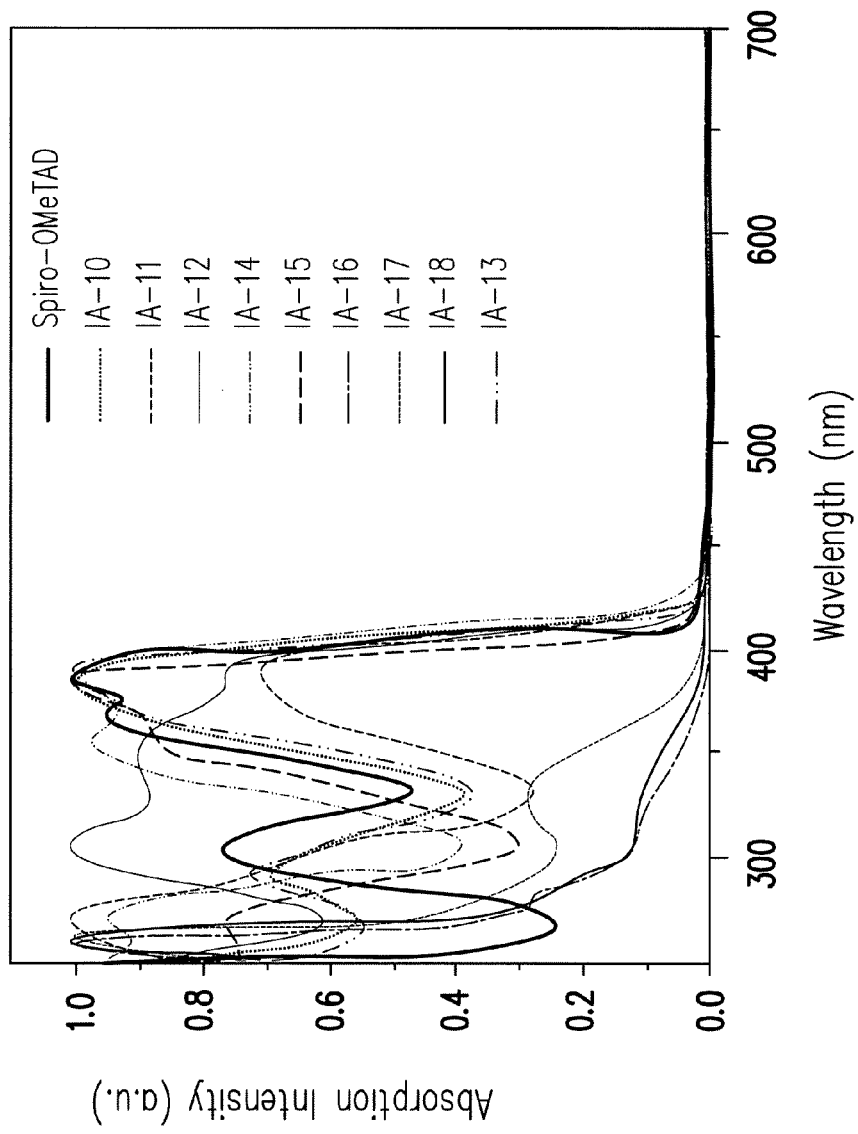
FIG. 1 is the absorption spectrum of each of compounds (IA-10) to (IA-18) of some embodiments of the invention.

The invention provides an organic compound with a tetrahedral-like geometry that has a structure represented by formula (I):

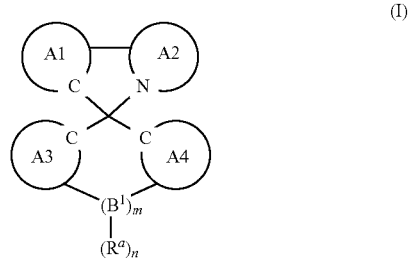

(I)

wherein A1 to A4 each independently represent a 5-membered or 6-membered unsaturated ring; $B^1$ represents direct bonding, —C—, —O—, —N—, —S— or —C=C—; m is 0 or 1; each of $R^a$'s is independently hydrogen, fluorine, oxygen, substituted or unsubstituted $C_1$-$C_{12}$ alkyl or substituted or unsubstituted $C_6$-$C_{12}$ aryl; and n is an integer of 0 to 2.

The above-mentioned "direct bonding" indicates, for example, a single bond between an atom on A3 and an atom on A4. That is, the atom on A3 and the atom on A4 are directly bonded without an additional bridging atom.

As shown in formula (I), at least one C—N bond replaces the conventional C—C bond, so that the organic compound of the invention has an asymmetry tetrahedral-like geometry. The photophysical properties of the organic compound with such tetrahedral-like geometry are relatively easy to be adjusted. Therefore, the organic compound of the invention has great potential application in the field of photoelectric materials.

In an embodiment, when the substituents on A3 and A4 of the organic compound represented by formula (I) provide donor properties with hole transporting capabilities, the organic compound of the invention can serve as a hole transporting material. When the substituents on A3 and A4 of the organic compound represented by formula (I) provide acceptor properties with electron transporting capabilities, the organic compound of the invention can serve as an electron transporting material. When the substituents of A1 and A2 have acceptor properties and the substituents on A3 and A4 have donor properties, the organic compound of the invention can exhibit higher thermally activated delayed fluorescence, so the application thereof can be accordingly broadened.

In an embodiment, A1 is a 6-membered unsaturated ring, A2 is a 5-membered unsaturated ring, and a structure of A3 and a structure of A4 are substantially identical. The 5-membered unsaturated ring has a reactivity different from that of the 6-membered unsaturated ring, so different substituents can be modified on the 5-membered and 6-membered unsaturated rings respectively, and the property of the organic compound of the invention can be adjusted easily.

Herein, the technical term "substantially identical structure" is defined as "completely identical ring structures with completely identical or partially identical substituents on the ring structures". In an embodiment, each of A3 and A4 is a 5-membered unsaturated ring or a 6-membered unsaturated ring. In an embodiment, each of A3 and A4 is a 5-membered unsaturated ring or a 6-membered unsaturated ring containing 0, 1 or 2 nitrogen atoms and 0 oxygen or sulfur atom.

In an embodiment, the organic compound with a tetrahedral-like geometry has a structure represented by the following formula (IA):

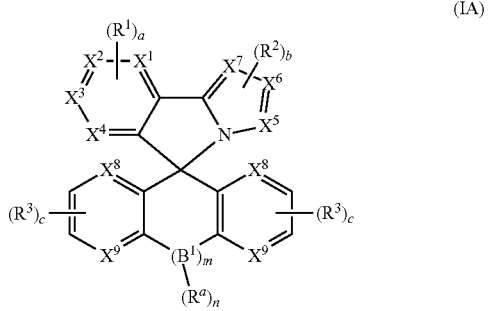

(IA)

wherein $X^1$ to $X^9$ are each independently carbon or nitrogen; each of $R^1$'s and $R^2$'s is independently hydrogen, substituted or unsubstituted $C_1$-$C_{12}$ alkyl, substituted or unsubstituted $C_1$-$C_6$ alkoxy, substituted or unsubstituted $C_6$-$C_{12}$ aryl or —$C_yF_{2y+1}$, y is an integer of 0 to 3; a is an integer of 0 to 4; b is an integer of 0 to 3; each of $R^3$'s is independently hydrogen, halogen, cyano, substituted or unsubstituted $C_1$-$C_{12}$ alkyl, substituted or unsubstituted $C_1$-$C_6$ alkoxy, substituted or unsubstituted $C_6$-$C_{12}$ aryl, substituted or unsubstituted amino or substituted or unsubstituted phosphinyl; c is an integer of 0 to 4; when c is equal to or greater than 1, each of $R^3$'s can be the same or different; $B^1$ represents direct bonding, —C—, —O—, —N—, —S— or —C═C—; m is 0 or 1; each of $R^a$'s is independently hydrogen, fluorine, oxygen, substituted or unsubstituted $C_1$-$C_{12}$ alkyl or substituted or unsubstituted $C_6$-$C_{12}$ aryl; and n is an integer of 0 to 2.

The above-mentioned "direct bonding" indicates, for example, a single bond between a carbon atom on the left side of $B^1$ and a carbon atom on the right side of $B^1$. That is, the carbon on the left side of $B^1$ and the carbon on the right side of $B^1$ are directly bonded without an additional bridging atom.

In an embodiment, the organic compound with a tetrahedral-like geometry has a structure represented by the following formula (IA-a):

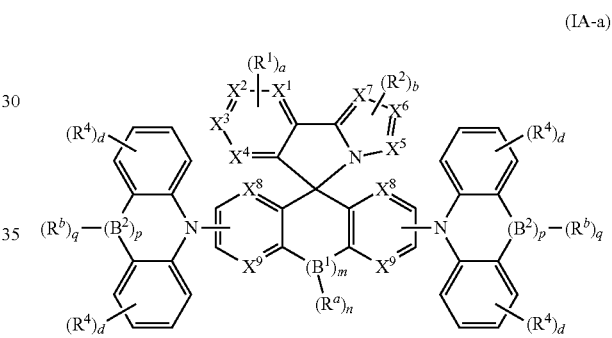

(IA-a)

wherein each of $R^4$'s is independently hydrogen, fluorine, substituted or unsubstituted $C_1$-$C_{12}$ alkyl, substituted or unsubstituted $C_1$-$C_6$ alkoxy or substituted or unsubstituted $C_6$-$C_{12}$ aryl; d is an integer of 0 to 4; when d is equal to or greater than 1, each of $R^4$'s can be the same or different, and two or more $R^4$'s can joint to form a $C_3$-$C_5$ aromatic ring; $B^2$ represents —O—, —S—, —C— or —N—; p is 0 or 1; each of $R^b$'s is independently hydrogen, fluorine, substituted or unsubstituted $C_1$-$C_{12}$ alkyl; and q is an integer of 0 to 2.

The aromatic ring can include an aromatic hydrocarbon ring or an aromatic heterocyclic ring. Specific examples of the aromatic ring include a phenyl ring, a pyridine ring, a pyrazine ring, a pyrimidine ring, a pyridazine ring, a triazine ring, a pyrrole ring, a furan ring, a thiophene ring, a selenophene ring, a tellurophene ring, an imidazole ring, a thiazole ring, a selenazole ring, a tellurazole ring, a thiadiazole ring, an oxadiazole ring, and a pyrazole ring.

In the organic compound with a tetrahedral-like geometry as shown in formula (IA-a), substituted or unsubstituted amino groups are modified on both side thereof. In an embodiment, substituted or unsubstituted amino groups have donor properties, so that the organic compound of the invention can exhibit higher thermally activated delayed fluorescence and excellent hole transporting properties.

In an embodiment, the organic compound with a tetrahedral-like geometry has a structure represented by one of formula (IA-1) to formula (IA-32):

IA-1
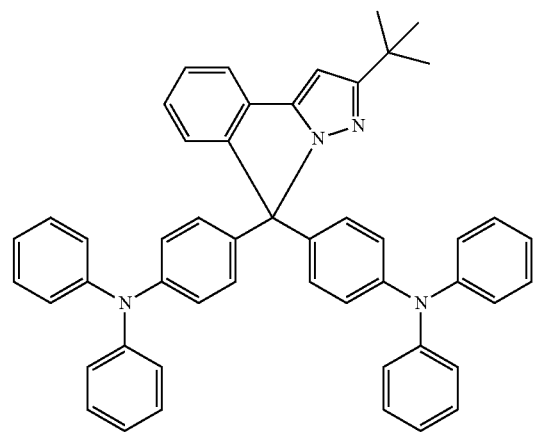 [SMILES: CC(C)(C)c1cc2n(n1)C(c1ccc(N(c3ccccc3)c3ccccc3)cc1)(c1ccc(N(c3ccccc3)c3ccccc3)cc1)c1ccccc1-2]
IA-2
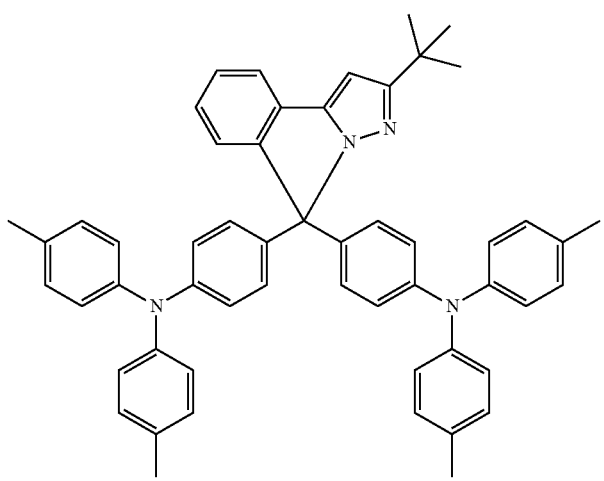
IA-3
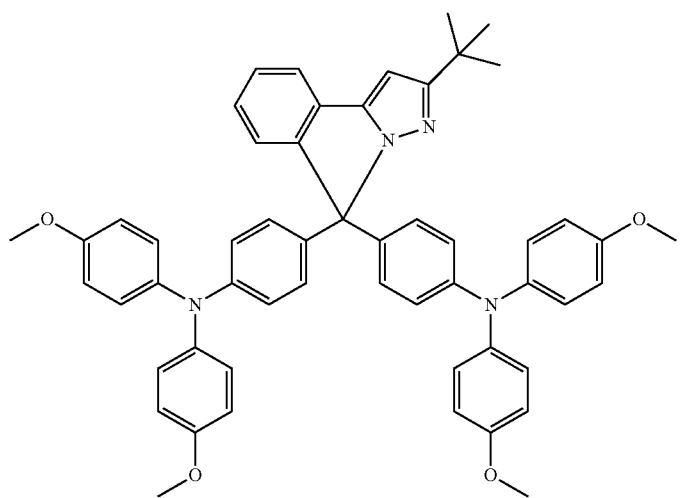

-continued
IA-4
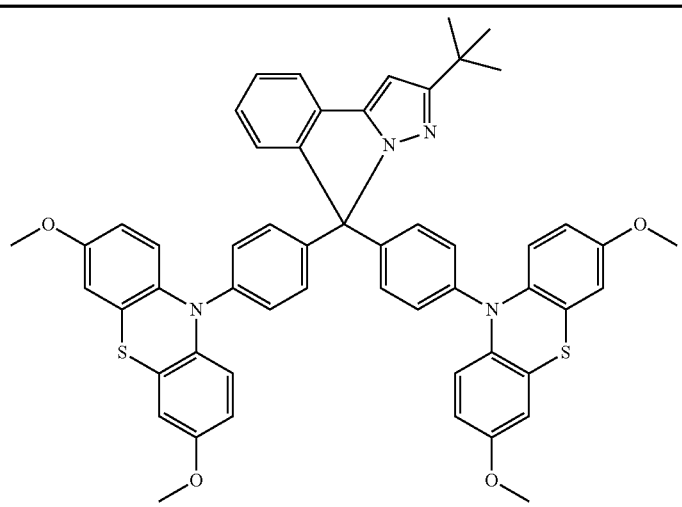
IA-5
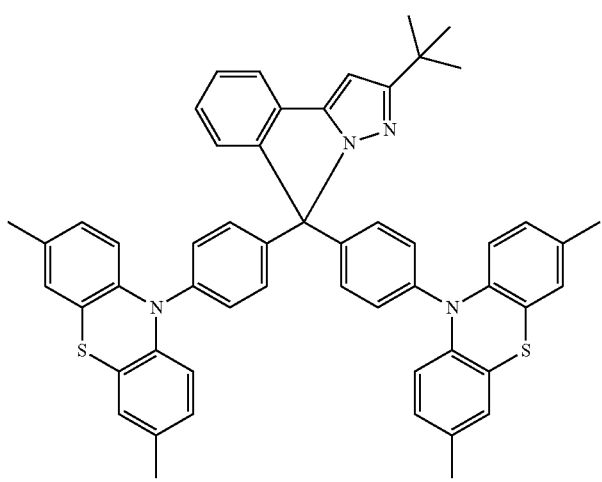
IA-6
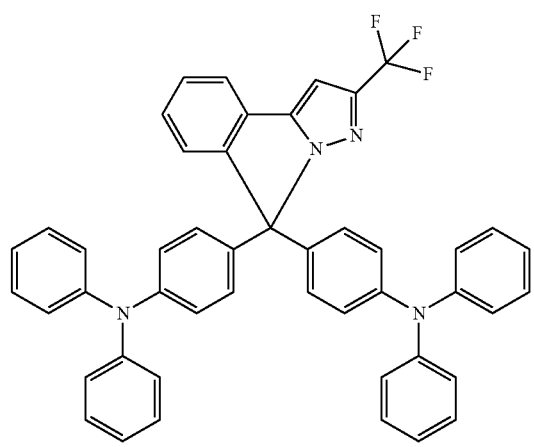 [SMILES: FC(F)(F)c1cc2n(n1)C(c1ccc(N(c3ccccc3)c3ccccc3)cc1)(c1ccc(N(c3ccccc3)c3ccccc3)cc1)c1ccccc1-2]

-continued
IA-7
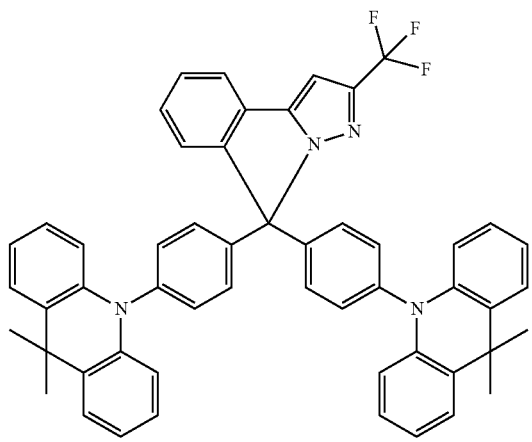 [SMILES: CC1(C)c2ccccc2N(c2ccc(C3(c4ccc(N5c6ccccc6C(C)(C)c6ccccc65)cc4)c4ccccc4-c4cc(C(F)(F)F)nn43)cc2)c2ccccc21]
IA-8
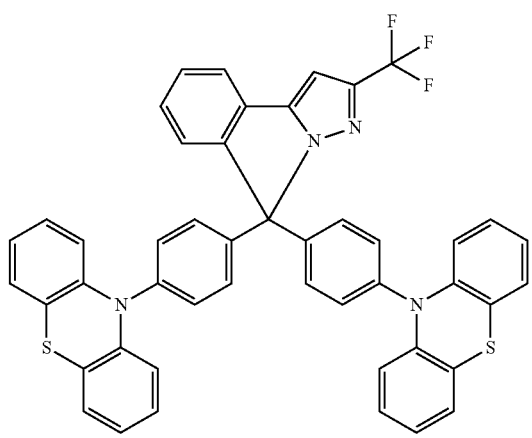 [SMILES: FC(F)(F)c1cc2n(n1)C(c1ccc(N3c4ccccc4Sc4ccccc43)cc1)(c1ccc(N3c4ccccc4Sc4ccccc43)cc1)c1ccccc1-2]
IA-9
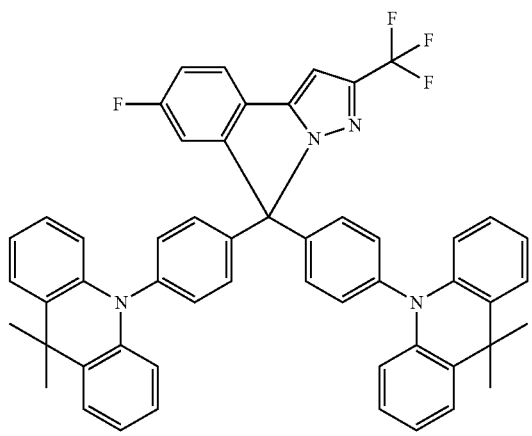 [SMILES: CC1(C)c2ccccc2N(c2ccc(C3(c4ccc(N5c6ccccc6C(C)(C)c6ccccc65)cc4)c4cc(F)ccc4-c4cc(C(F)(F)F)nn43)cc2)c2ccccc21]

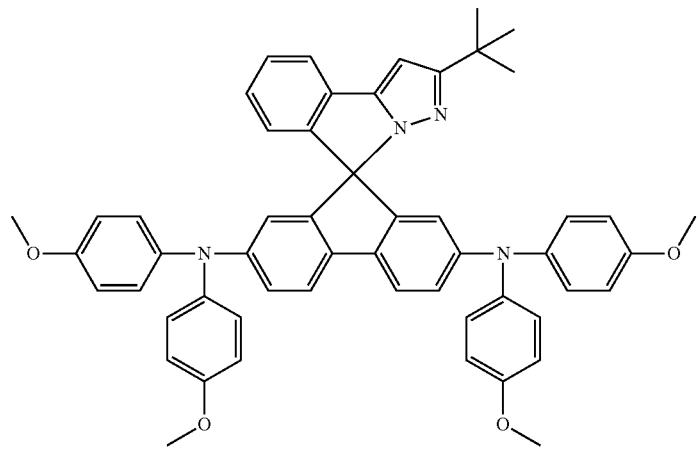
IA-10
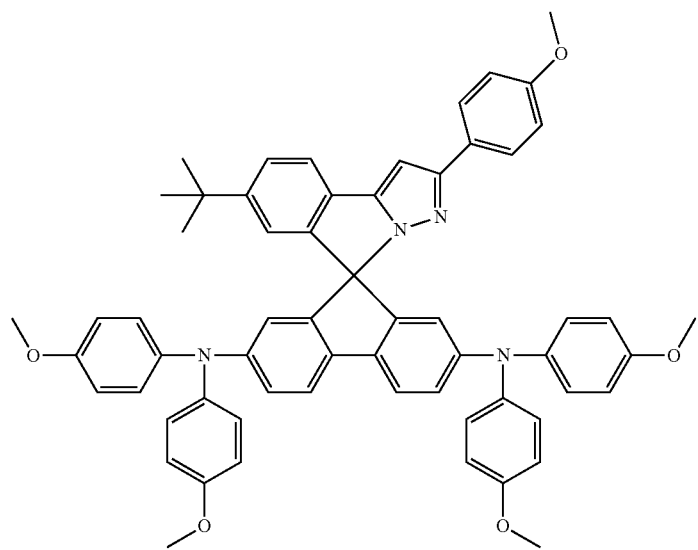
IA-11

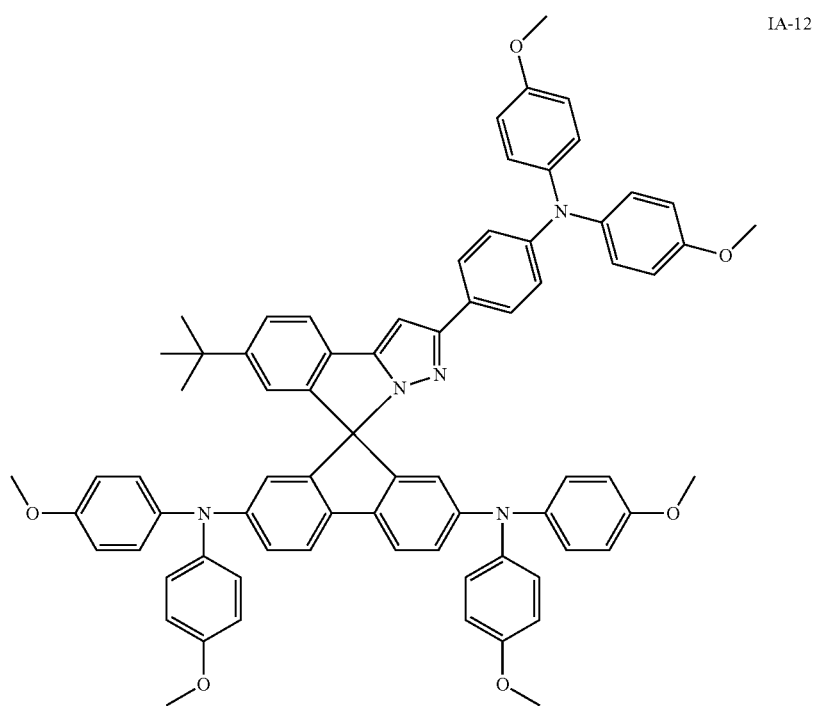
IA-12
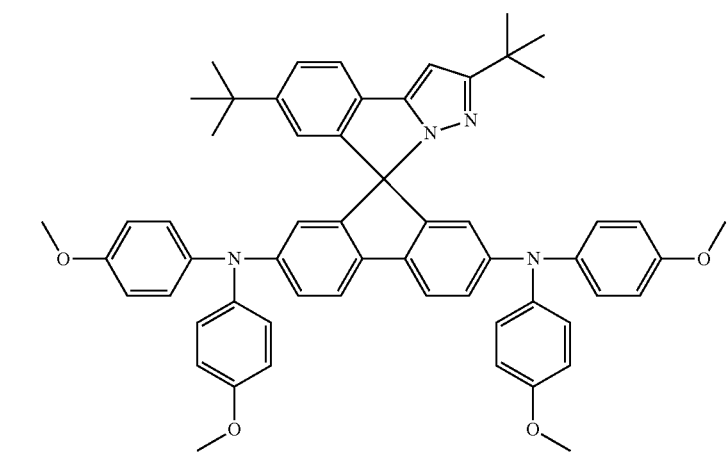
IA-13
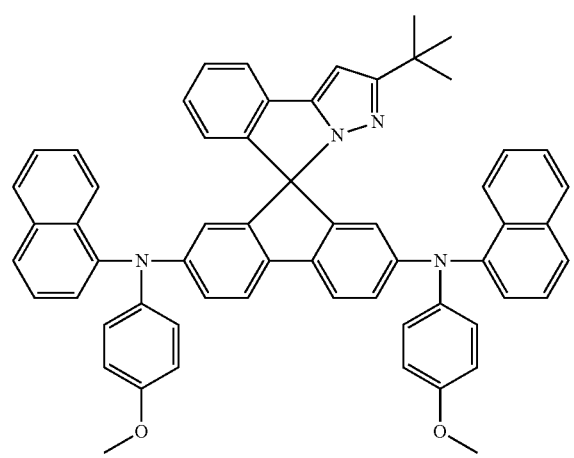 [SMILES: COc1ccc(N(c2ccc3c(c2)C2(c4cc(N(c5ccc(OC)cc5)c5cccc6ccccc56)ccc4-3)c3ccccc3-c3cc(C(C)(C)C)nn32)c2cccc3ccccc23)cc1]
IA-14

-continued
IA-15
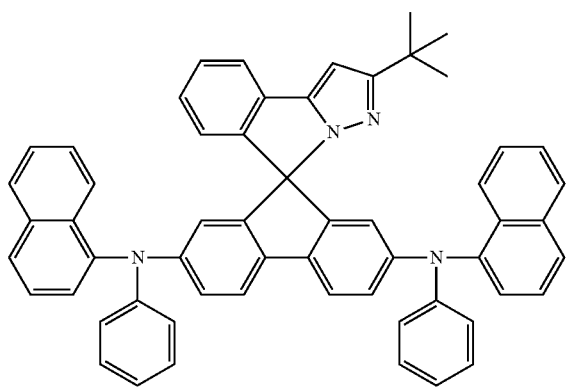 [SMILES: CC(C)(C)c1cc2n(n1)C1(c3cc(N(c4ccccc4)c4cccc5ccccc45)ccc3-c3ccc(N(c4ccccc4)c4cccc5ccccc45)cc31)c1ccccc1-2]
IA-16
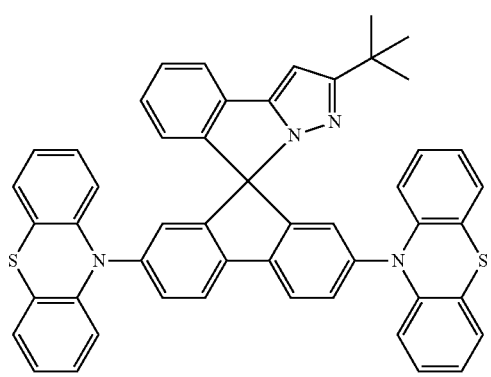 [SMILES: CC(C)(C)c1cc2n(n1)C1(c3cc(N4c5ccccc5Sc5ccccc54)ccc3-c3ccc(N4c5ccccc5Sc5ccccc54)cc31)c1ccccc1-2]
IA-17
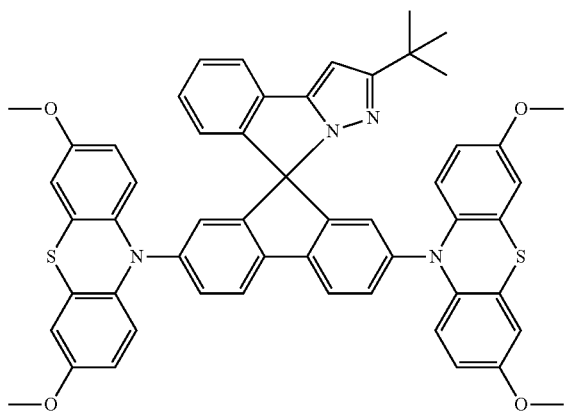
IA-18
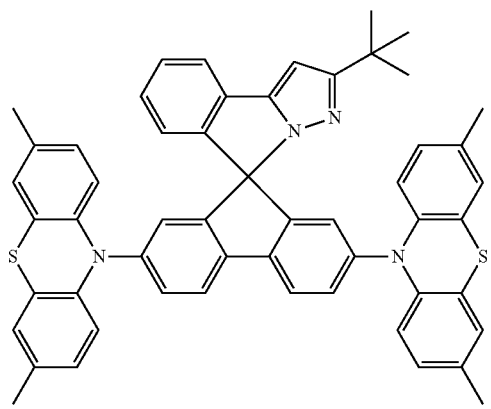 [SMILES: Cc1ccc2c(c1)Sc1cc(C)ccc1N2c1ccc2c(c1)C1(c3cc(N4c5ccc(C)cc5Sc5cc(C)ccc54)ccc3-2)c2ccccc2-c2cc(C(C)(C)C)nn21]

-continued
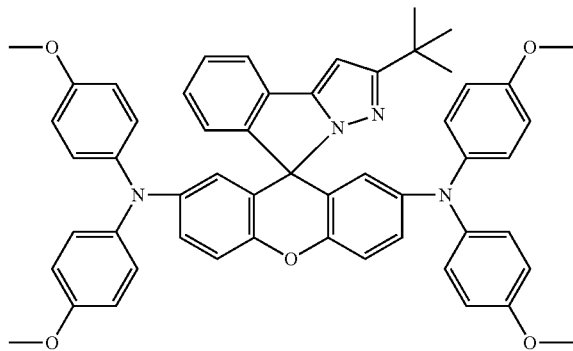
IA-19
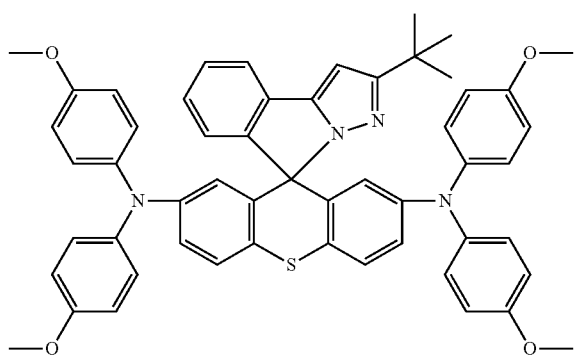
IA-20
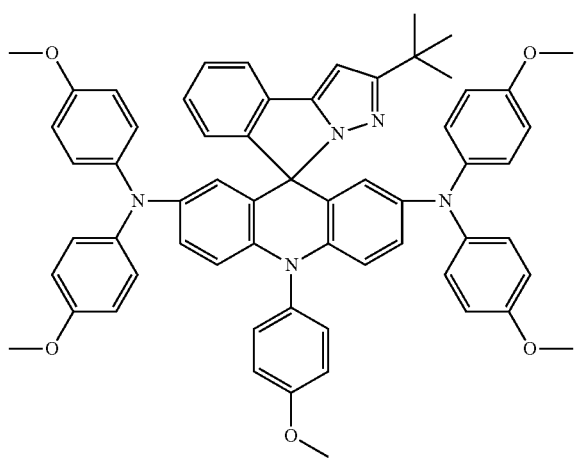
IA-21
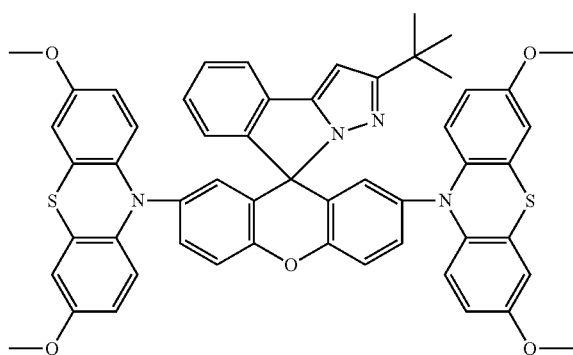
IA-22

-continued
IA-23
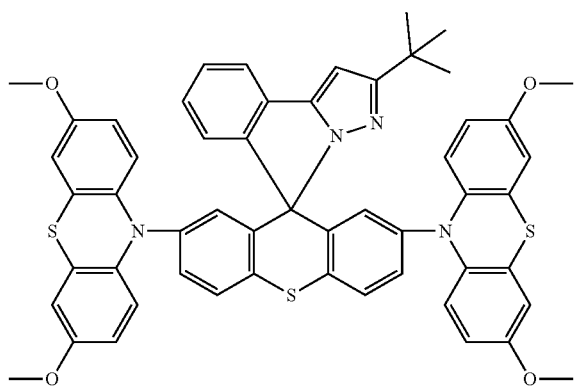
IA-24
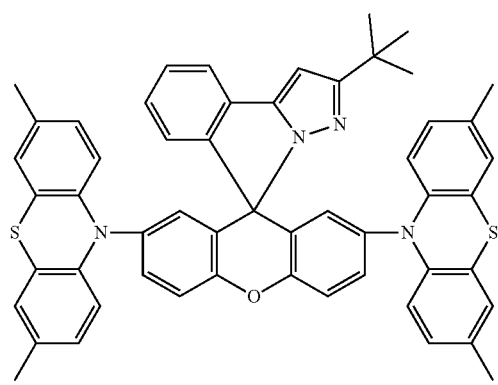 [SMILES: Cc1ccc2c(c1)Sc1cc(C)ccc1N2c1ccc2c(c1)C1(c3cc(N4c5ccc(C)cc5Sc5cc(C)ccc54)ccc3O2)c2ccccc2-c2cc(C(C)(C)C)nn21]
IA-25
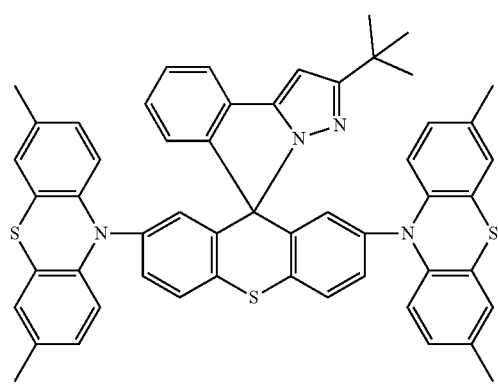
IA-26
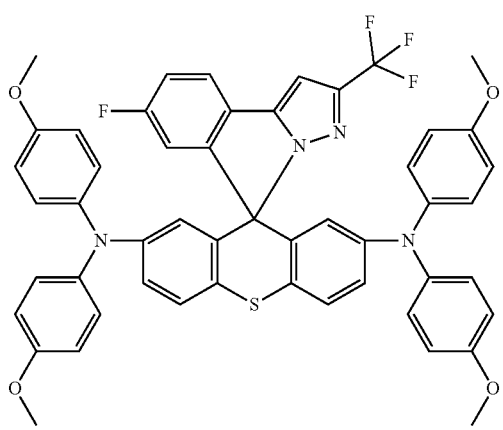 [SMILES: COc1ccc(N(c2ccc(OC)cc2)c2ccc3c(c2)C2(c4cc(N(c5ccc(OC)cc5)c5ccc(OC)cc5)ccc4S3)c3cc(F)ccc3-c3cc(C(F)(F)F)nn32)cc1]

-continued
IA-27
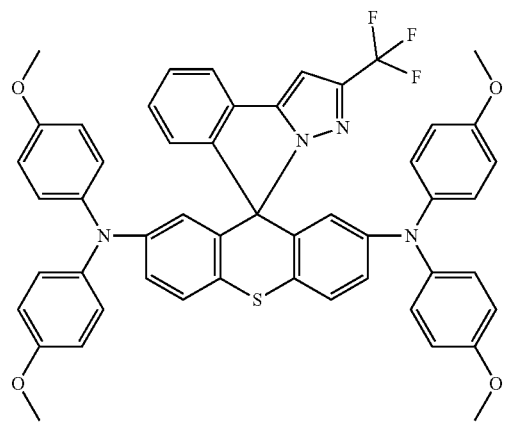 [SMILES: COc1ccc(N(c2ccc(OC)cc2)c2ccc3c(c2)C2(c4cc(N(c5ccc(OC)cc5)c5ccc(OC)cc5)ccc4S3)c3ccccc3-c3cc(C(F)(F)F)nn32)cc1]
IA-28
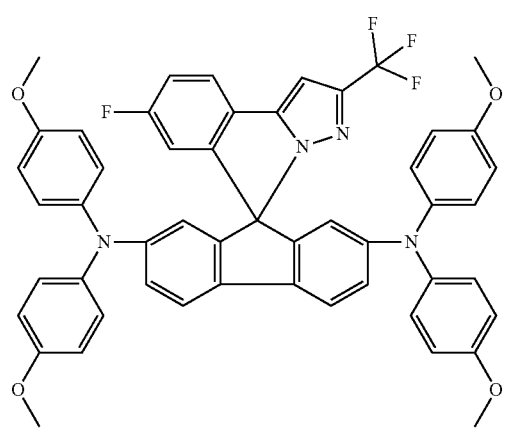 [SMILES: COc1ccc(N(c2ccc(OC)cc2)c2ccc3c(c2)C2(c4cc(N(c5ccc(OC)cc5)c5ccc(OC)cc5)ccc4-3)c3cc(F)ccc3-c3cc(C(F)(F)F)nn32)cc1]
IA-29
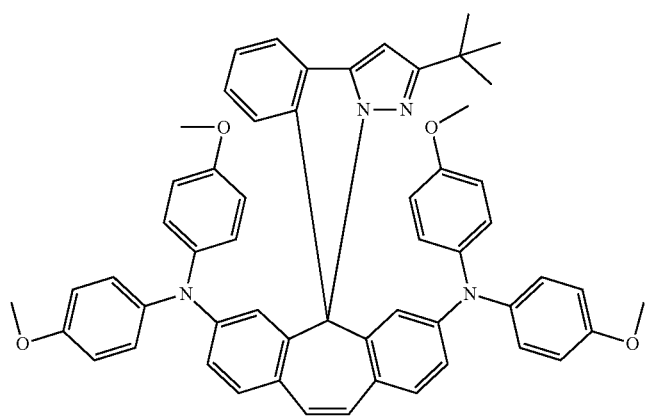

-continued

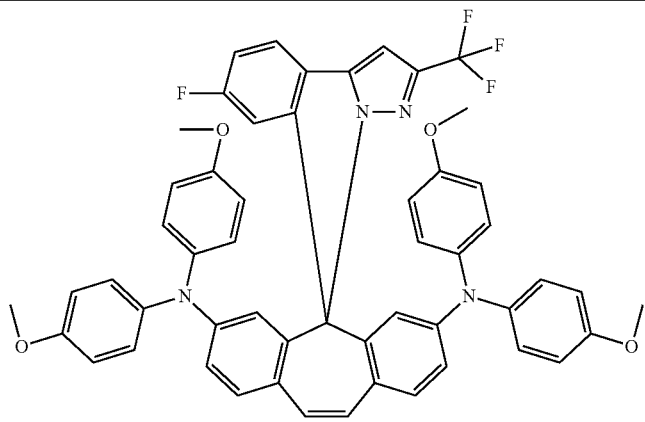

IA-30

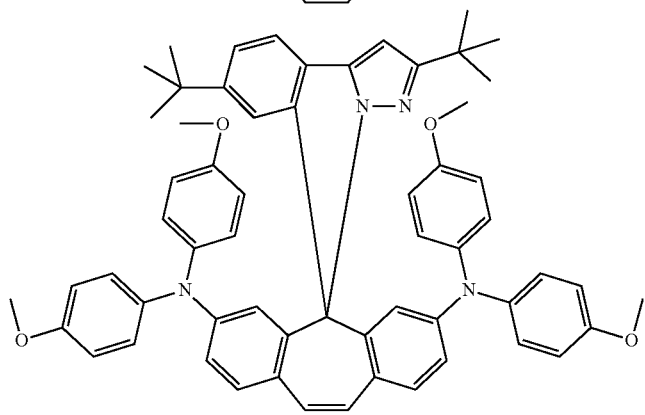

IA-31

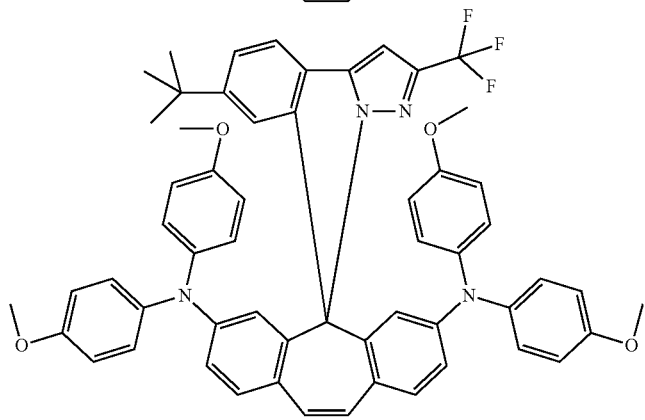

IA-32

In an embodiment, the organic compound with a tetrahedral-like geometry has a structure represented by the following formula (IA-b):

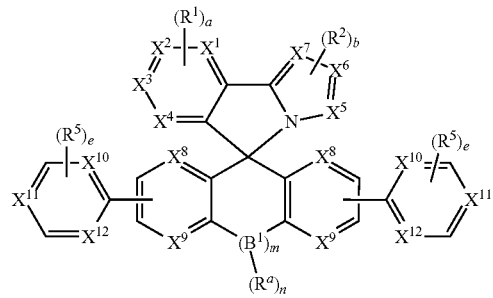

(IA-b)

wherein $X^{10}$ to $X^{12}$ are each independently carbon or nitrogen; each $X^{10}$ can be the same or different; each $X^{11}$ can be the same or different; each $X^{12}$ can be the same or different; each of $R^5$'s is independently hydrogen, fluorine, substituted or unsubstituted $C_1$-$C_{12}$ alkyl, substituted or unsubstituted $C_1$-$C_6$ alkoxy or substituted or unsubstituted $C_6$-$C_{12}$ aryl; e is an integer of 0 to 5; and when e is equal to or greater than 1, each of $R^5$'s can be the same or different.

In an embodiment, the organic compound with a tetrahedral-like geometry as shown in formula (IA-b) has an excellent electron transporting property.

In an embodiment, the organic compound with a tetrahedral-like geometry has a structure represented by one of formula (IA-33) to formula (IA-46):

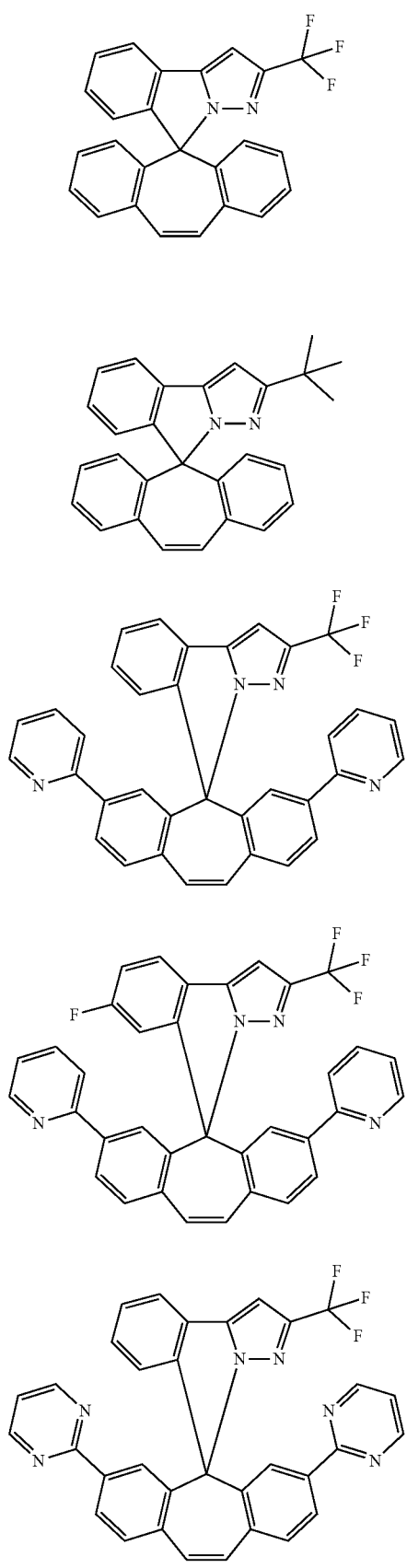
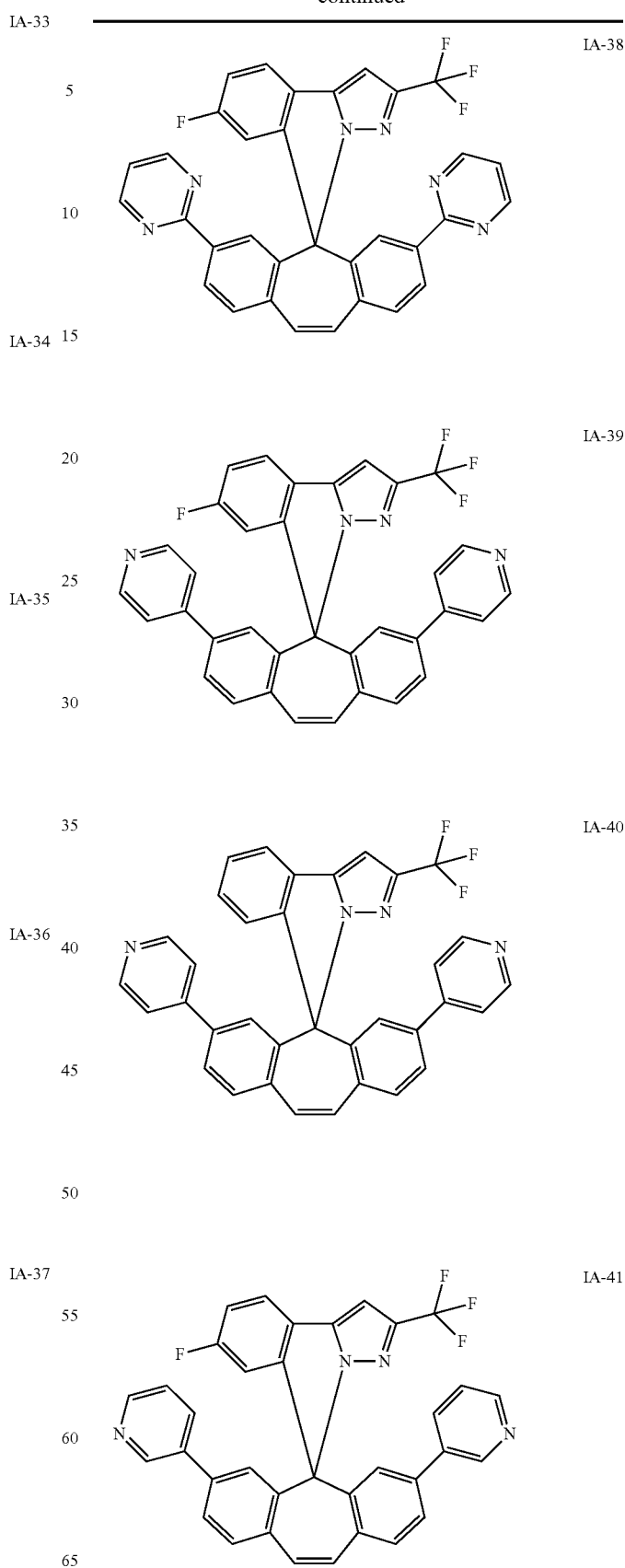

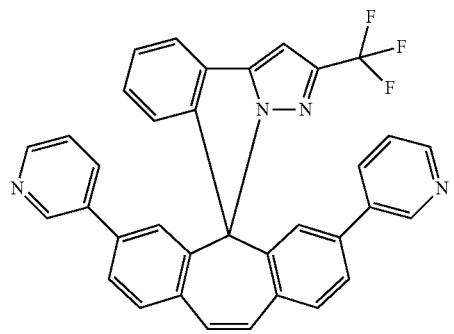 [SMILES: FC(F)(F)c1cc2n(n1)C1(c3cc(-c4cccnc4)ccc3C=Cc3ccc(-c4cccnc4)cc31)c1ccccc1-2]

IA-42

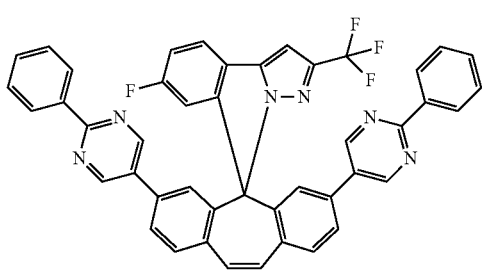 [SMILES: Fc1ccc2c(c1)C1(c3cc(-c4cnc(-c5ccccc5)nc4)ccc3C=Cc3ccc(-c4cnc(-c5ccccc5)nc4)cc31)n1nc(C(F)(F)F)cc1-2]

IA-43

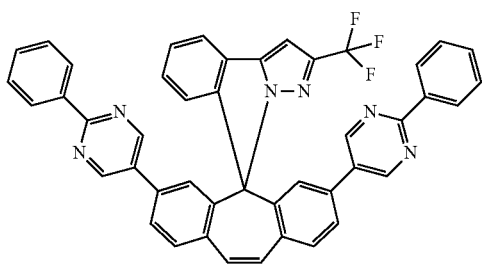

IA-44

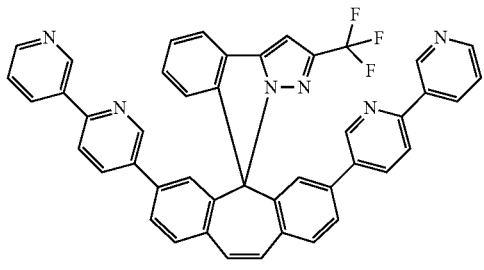 [SMILES: FC(F)(F)c1cc2n(n1)C1(c3cc(-c4ccc(-c5cccnc5)nc4)ccc3C=Cc3ccc(-c4ccc(-c5cccnc5)nc4)cc31)c1ccccc1-2]

IA-45

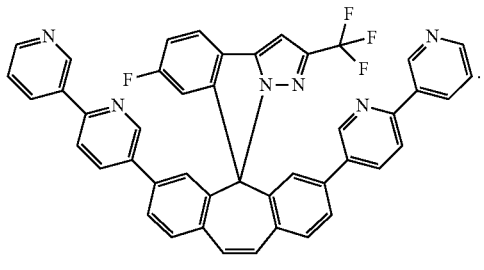 [SMILES: Fc1ccc2c(c1)C1(c3cc(-c4ccc(-c5cccnc5)nc4)ccc3C=Cc3ccc(-c4ccc(-c5cccnc5)nc4)cc31)n1nc(C(F)(F)F)cc1-2]

IA-46

In an embodiment, the organic compound with a tetrahedral-like geometry has a structure represented by the following formula (IA-c):

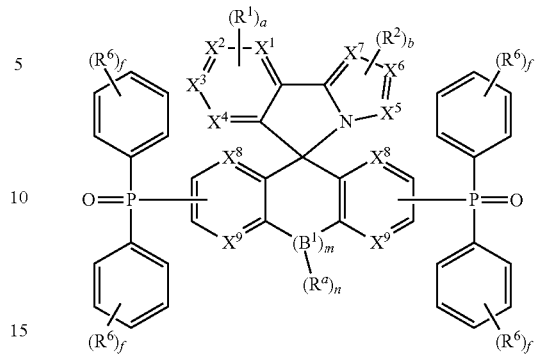

(IA-c)

wherein each of $R^6$'s is independently hydrogen, fluorine, substituted or unsubstituted $C_1$-$C_{12}$ alkyl, substituted or unsubstituted $C_1$-$C_6$ alkoxy or substituted or unsubstituted $C_6$-$C_{12}$ aryl; f is an integer of 0 to 5; and when f is equal to or greater than 1, each of $R^6$'s can be the same or different.

In an embodiment, the organic compound with a tetrahedral-like geometry as shown in formula (IA-c) has an excellent electron transporting property.

In an embodiment, the organic compound with a tetrahedral-like geometry has a structure represented by one of formula (IA-47) to formula (IA-48):

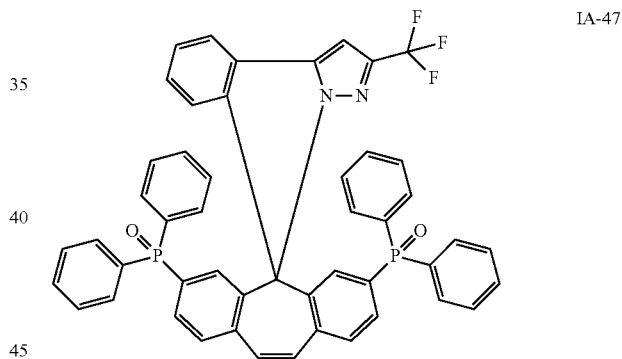

IA-47

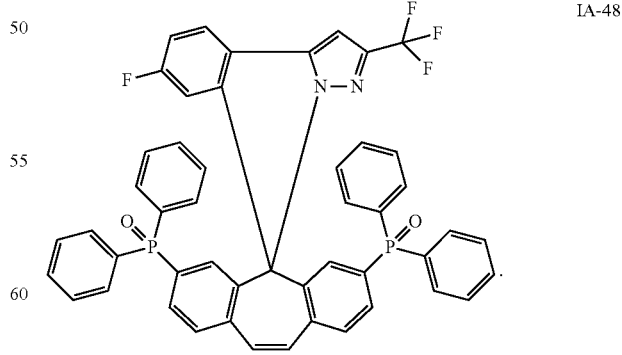

IA-48

In an embodiment, the organic compound with a tetrahedral-like geometry has a structure represented by one of formula (IA-49) to formula (IA-52):

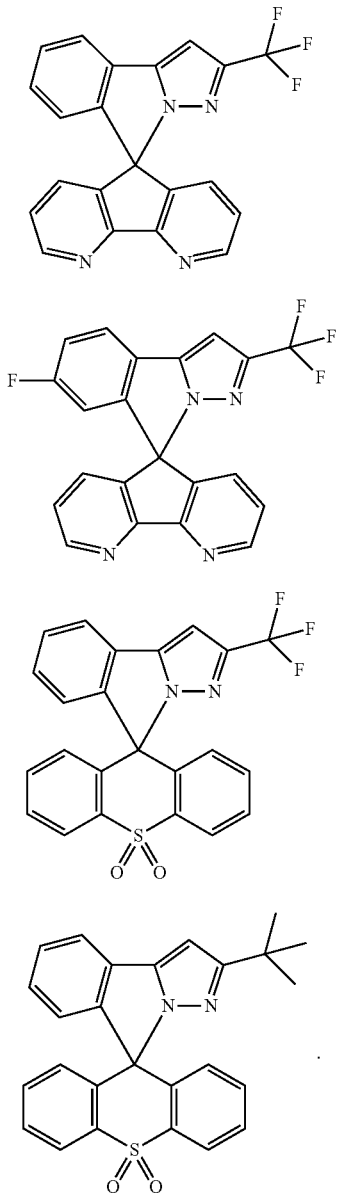

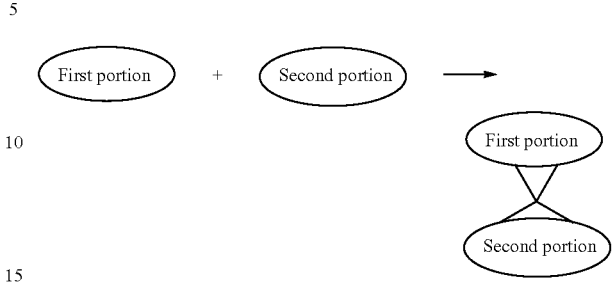

[Synthesis of the Organic Compounds of the Invention]

The organic compound with a tetrahedral-like geometry of the invention is, for example, synthesized by the following method:

Specifically, the synthesis method of the organic compound with a tetrahedral-like geometry of the invention includes, for example, synthesizing each of a first portion and a second portion of the organic compound, and then reacting the first portion with the second portion of the organic compound, so as to obtain the organic compound of the invention. Those having ordinary skill in the art can select suitable reactants and reaction conditions according to the changes of each of the organic compounds, and the synthesis reaction can be modified based on a known technique in the art, so the details are not repeated herein.

EMBODIMENTS

In the following, several examples are provided to further describe the invention, but the examples are only exemplary and are not intended to limit the scope of the invention. The organic compounds represented by formulas (IA-1), (IA-2), (IA-3) . . . are abbreviated as compounds (IA-1), (IA-2), (IA-3) . . . hereinafter. The abbreviations also apply to organic compounds represented by other chemical structures in the following.

Embodiment 1: Synthesis of Compound (Ia-10)

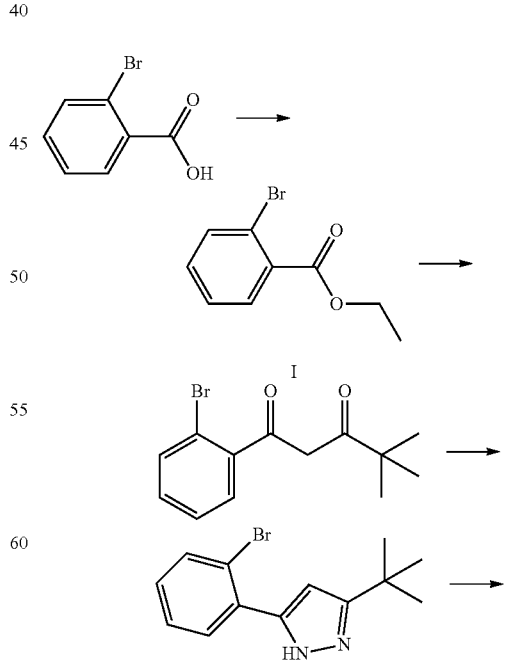

In an embodiment, at least one of $X^1$ to $X^4$ is nitrogen. More specifically, at least one of $X^1$ to $X^4$ in the organic compound represented by each of formulae (IA), (IA-a), (IA-b) and (IA-c) is nitrogen indicates that the upper-left 6-membered unsaturated ring thereof has one or more nitrogen atoms. The 6-membered unsaturated ring with one or more nitrogen atoms provides an acceptor property, so that the organic compound of the invention can exhibit higher thermally activated delayed fluorescence.

Based on the above, the organic compound of the invention has an asymmetry tetrahedral-like geometry, so that the organic compound of the invention has excellent photophysical properties. In addition, as compared to the conventional technology, the solar cell containing the organic compound of the invention has comparable (or even better) energy conversion efficiency. Therefore, the organic compound of the invention has a considerably high application value.

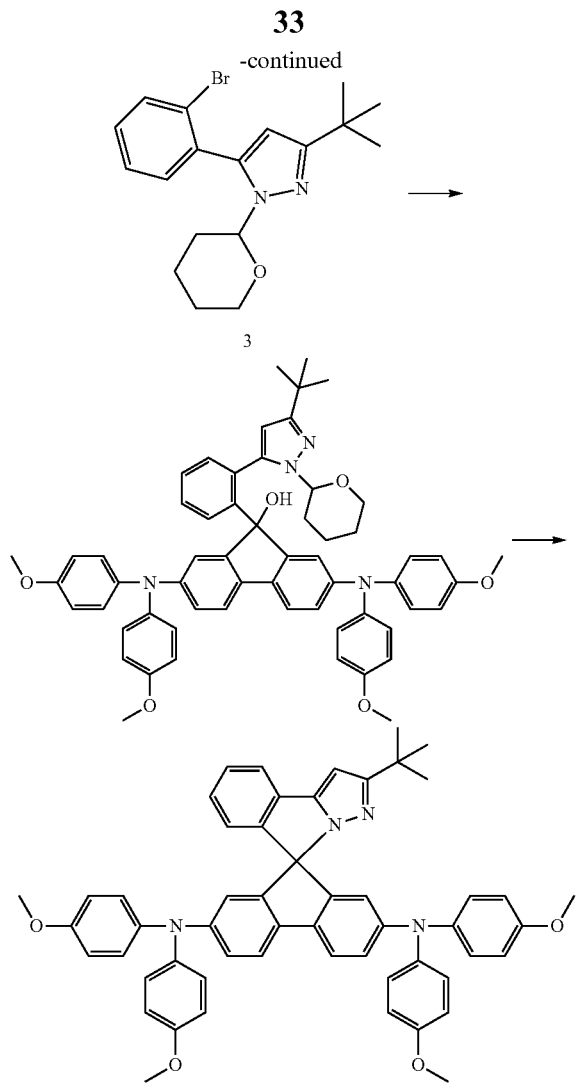

Synthesis of Compound (1):

2-Bromobenzoic acid (2.0 g, 10 mmol) was dissolved in EtOH (80 mL), $H_2SO_4$ (3 mL) and refluxed for 12 hours. The mixture was poured into water and extracted with ethyl acetate. The organic layer was washed with $NaHCO_3$, brine and water in sequence, and dried over $Na_2SO_4$. The colorless product was obtained (1.8 g) by column chromatography using hexane:EA=30:1 as the eluent in a yield of 80%.

Spectral data of compound (1): $^1$H NMR (400 MHz, $CDCl_3$): δ 7.76 (dd, J=7.6, 1.9 Hz, 1H), 7.64 (dd, J=7.6, 1.6 Hz, 1H), 7.37-7.28 (m, 2H), 4.39 (q, J=6.8 Hz, 2H), 1.39 (t, J=7.1 Hz, 3H).

Synthesis of Compound (2):

NaH (478 mg, 19 mmol) was suspended in 16 mL of dry THF under nitrogen. 3,3-dimethylbutan-2-one (1.27 g, 12.6 mmol) was dissolved in 8 mL of dry THF and added dropwise at 0° C. Then, the mixture was stirred at room temperature for 1 hour. After that, compound (1) (4.38 g, 18.7 mmol) dissolved in 16 mL of dry THF was added dropwise at 0° C. The mixture was refluxed for 4 hours. The mixture was poured into a mixture of water and ethyl acetate, and acidified with 2M HCl. The organic layer was washed with brine and water in sequence, and dried over $Na_2SO_4$. The crude product was obtained by removal of all solvent. This crude product, hydrazine hydrate (3 mL, 63 mmol) and p-toluenesulfonic acid monohydrate (228 mg, 1.2 mmol) were added to EtOH (65 mL) under nitrogen and refluxed for 12 hours. Then, the mixture was poured into a mixture of water and ethyl acetate and acidified with 2M HCl. The organic layer was washed with $NaHCO_3$, brine and water, and finally dried over $Na_2SO_4$. The product was obtained by column chromatography using hexane:EA=4:1 as the eluent in a yield of 60%.

Spectral data of compound (2): $^1$H NMR (400 MHz, $CDCl_3$): δ 7.63 (d, J=8.0 Hz, 1H), 7.59 (d, J=7.8 Hz, 1H), 7.31 (t, J=7.5 Hz, 1H), 7.16 (t, J=8.4 Hz, 1H), 6.48 (s, 1H), 1.33 (s, 9H).

Synthesis of Compound (3):

A mixture of compound (2) (2.09 mg, 7.5 mmol), 3,4-dihydro-2H-pyran (2.52 g, 30 mmol), p-toluenesulfonic acid monohydrate (140 mg, 0.75 mmol) and $CH_2Cl_2$ (50 mL) was refluxed overnight under nitrogen. Then, the mixture was washed with $NaHCO_3$, brine and water in sequence, and finally dried over $Na_2SO_4$. The product was obtained by column chromatography using hexane:EA=20:1 as the eluent in a yield of 77%.

Spectral data of compound (3): $^1$H NMR (400 MHz, $CDCl_3$): δ 7.65 (dd, J=7.8, 1.1 Hz, 1H), 7.43 (dd, J=7.6, 1.7 Hz, 1H), 7.35 (td, J=7.5, 1.3 Hz, 1H), 7.27-7.22 (m, 1H), 6.16 (s, 1H), 4.93-4.87 (m, 1H), 4.00-3.96 (m, 1H), 3.39-3.33 (m, 1H), 2.46-2.40 (m, 1H), 2.03-1.99 (m, 1H), 1.88-1.83 (m, 2H), 1.67-1.64 (m, 1H), 1.45-1.41 (m, 1H), 1.33 (s, 9H).

Synthesis of Compound (IA-10):

A solution of compound (3) (433 mg, 1.22 mmol) in dry THF (5 mL) was treated with n-BuLi (731 μL, 2.5 M in n-hexane) under nitrogen at −78° C. After stirring for 30 min, a solution of 2,7-bis(bis(4-methoxyphenyl)amino)-9H-fluoren-9-one (551 mg, 0.87 mmol) in THF (5 mL) was added dropwise. The mixture was stirred for 30 minutes at −78° C., and allowed to warm up to room temperature. After stirring for another 12 hours, the solution was concentrated and the residue was extracted with $CH_2Cl_2$ and washed with brine and water in sequence and finally dried over $Na_2SO_4$.

The intermediate of tertiary alcohol could be obtained by column chromatography using hexane:EA=4:1 as the eluent. Then, the intermediate was added to a mixture of concentrated aqueous HCl (1.5 mL) and acetic acid (20 mL). After stirring at room temperature for 1 hour, the reaction mixture was quenched with ice water and neutralized with $NaHCO_3$ (aq). The crude product was extracted with $CH_2Cl_2$ and washed with water. The organic layer was dried over anhydrous $Na_2SO_4$ and purified by silica gel column chromatography eluting with hexane:EA=8:1 as the eluent in a yield of 45%.

Spectral data of compound (IA-10): $^1$H NMR (400 MHz, DMSO-$d_6$): δ 7.59-7.56 (m, 3H), 7.34 (t, J=7.6 Hz, 1H), 7.17 (t, J=7.6 Hz, 1H), 6.81-6.72 (m, 19H), 6.33 (s, 1H), 6.00 (s, 2H), 3.64 (s, 12H), 1.19 (s, 9H). MS [FAB], m/z 816.4, M$^+$. Anal. Calcd. for $C_{54}H_{48}N_4O_4$: C, 79.39; H, 5.92; N, 6.86. Found: C, 78.52; H, 5.90; N, 6.16.

Embodiment 2: Synthesis of Compound (IA-11)

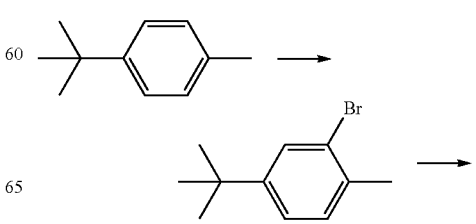

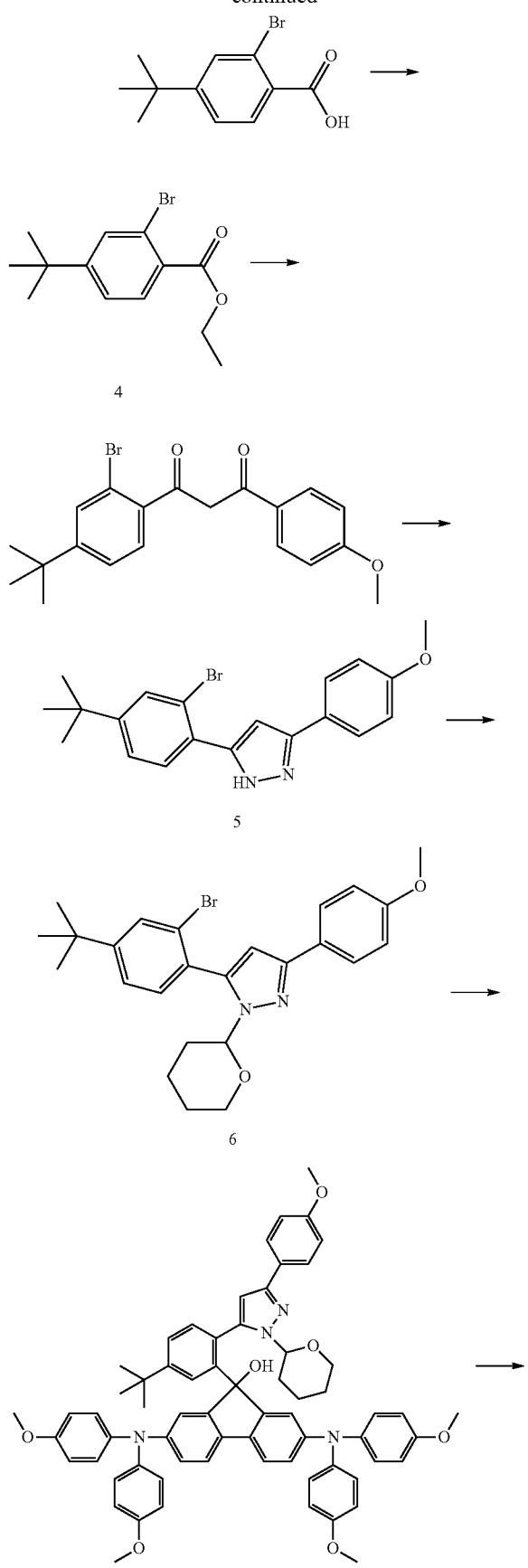
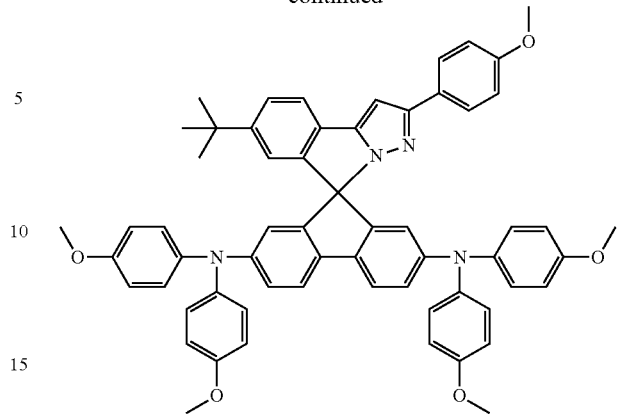

Synthesis of Compound (4):

p-tert-butyltoluene (5.0 mL, 29 mmol) was dissolved in 60 mL of CH$_3$CN. NaBrO$_3$ (13.2 g, 87.0 mmol) dissolved in H$_2$O (45 mL) was added, followed by addition of NaHSO$_3$ (9.0 g, 87.0 mmol) dissolved in H$_2$O (90 mL) over 15 minutes. The reaction was stirred for 16 hours. The reaction mixture was extracted with Et$_2$O. The combined organic layer was washed with sat. Na$_2$S$_2$O$_3$, brine and water in sequence, and finally dried over Na$_2$SO$_4$. The crude product was obtained by removal of all solvents. Then, it was dissolved in t-BuOH (50 mL) and H$_2$O (50 mL). KMnO$_4$ (13.8 g, 87 mmol) was added and the mixture was refluxed for 16 hours. The mixture was cooled to room temperature and filtered through a pad of Celite. The filtrate was acidified with 2M HCl and extracted with ethyl acetate. The organic layer was washed with brine and water, and finally dried over Na$_2$SO$_4$. The white crude product can be obtained by removal of all solvents. Finally, it was dissolved in EtOH (100 mL), H$_2$SO$_4$ (1.5 mL) was next added, and refluxed for 12 hours. The mixture was poured into water and extracted with ethyl acetate. The organic layer was washed with NaHCO$_3$, brine and water in sequence, and dried over Na$_2$SO$_4$. The pure white product was obtained (4.8 g) by column chromatography using hexane:EA=30:1 as the eluent in a yield of 58%.

Spectral data of compound (4): $^1$H NMR (400 MHz, CDCl$_3$): δ 7.73 (d, J=8.2 Hz, 1H), 7.63 (d, J=1.9 Hz, 1H), 7.35 (dd, J=7.3, 2.8 Hz, 1H), 4.37 (q, J=7.2 Hz, 2H), 1.38 (t, J=7.1 Hz, 3H), 1.30 (s, 9H).

Synthesis of Compound (5):

The procedure described for compound (2) was performed, except that different reactants were employed, to obtain a white product of compound (5) in a yield of 75%.

Spectral data of compound (5): $^1$H NMR (400 MHz, CDCl$_3$): δ 7.69 (d, J=8.8 Hz, 2H), 7.66 (d, J=1.9 Hz, 1H), 7.52 (d, J=8.1 Hz, 1H), 7.38 (dd, J=8.2, 1.9 Hz, 1H), 6.95 (d, J=8.8 Hz, 2H), 6.82 (s, 1H), 3.84 (s, 3H), 1.33 (s, 9H).

Synthesis of Compound (6):

The procedure described for compound (3) was performed, except that different reactants were employed, to obtain a white product of compound (6) in a total yield of 85%.

Spectral data of compound (6): $^1$H NMR (400 MHz, CDCl$_3$): δ 7.80 (d, J=8.9 Hz, 2H), 7.68-7.67 (m, 1H), 7.39 (d, J=1.1 Hz, 2H), 6.91 (d, J=8.9 Hz, 2H), 6.53 (s, 1H), 4.98-4.96 (m, 1H), 4.04-4.01 (m, 1H), 3.82 (s, 3H), 3.46-3.40 (m, 1H), 2.59-2.57 (m, 1H), 2.10-2.05 (m, 1H), 1.97-1.93 (m, 1H), 1.74-1.68 (m, 2H), 1.63-1.60 (m, 1H), 1.35 (s, 9H). MS [FAB], m/z 470.2, M$^+$.

Synthesis of Compound (IA-11):

The procedure described for compound (IA-10) was performed, except that different reactants were employed, to obtain a pale yellow product of compound (IA-11) in a yield of 54%.

Spectral data of compound (IA-11): $^1$H NMR (400 MHz, DMSO-$d_6$): δ 7.65-7.56 (m, 5H), 7.44 (d, J=8.0 Hz, 1H), 6.92 (d, J=12.9 Hz, 2H), 6.79-6.74 (m, 12H), 6.66-6.64 (m, 9H), 6.10 (s, 1H), 3.74 (s, 3H), 3.60 (s, 12H), 1.18 (s, 9H). MS [FAB], m/z 922.5, M$^+$. Anal. Calcd. for $C_{61}H_{54}N_4O_5$: C, 79.37; H, 5.90; N, 6.07. Found: C, 78.66; H, 5.91; N, 6.14.

Embodiment 3: Synthesis of Compound (IA-12)

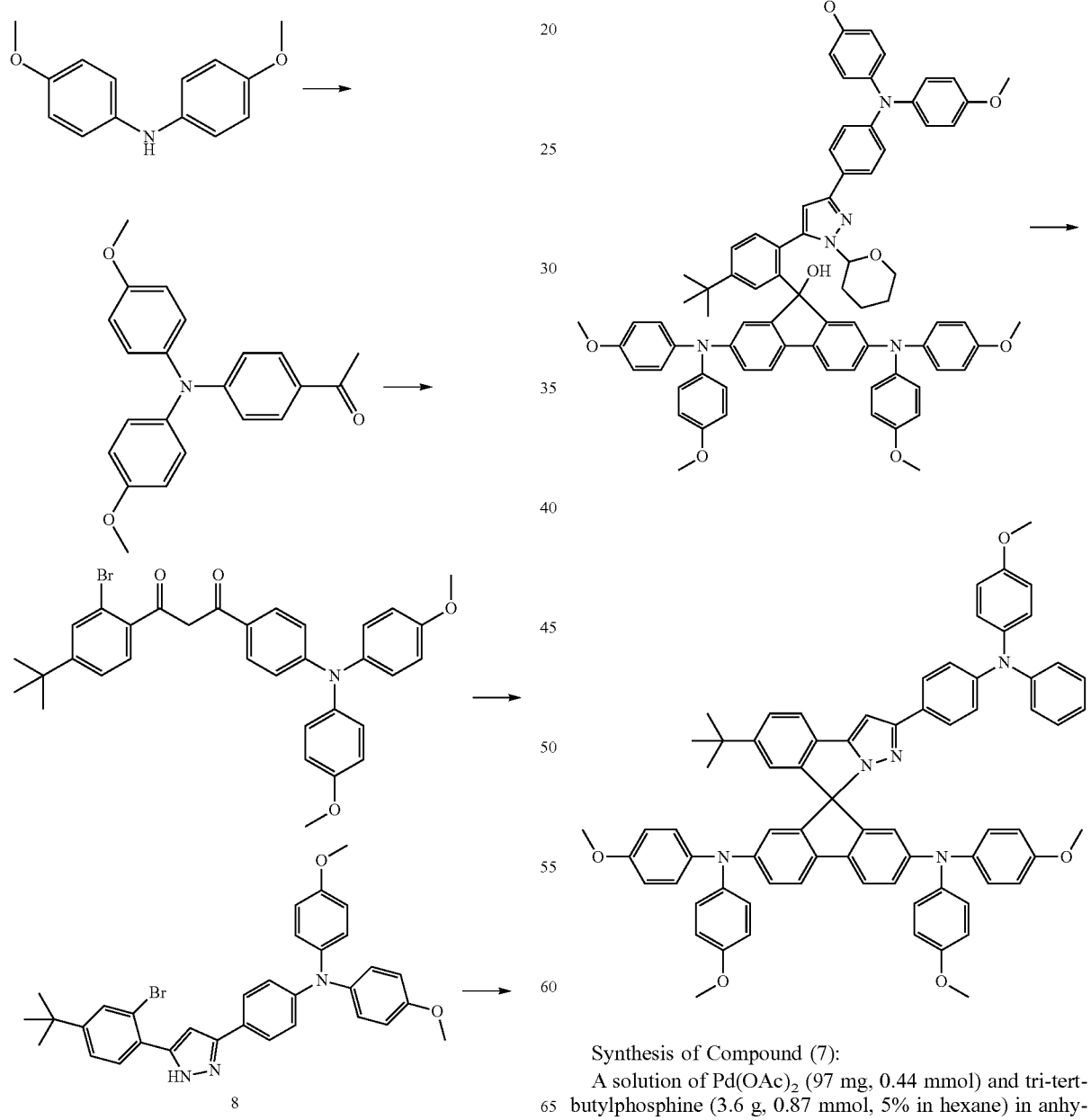

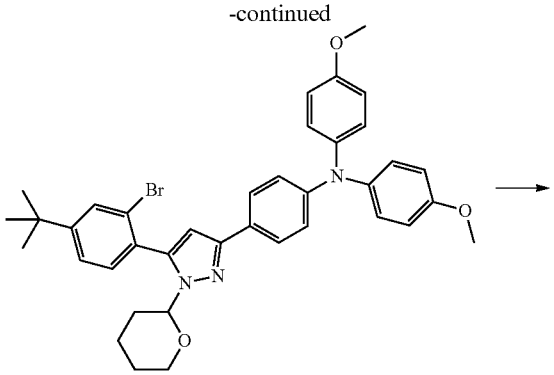

Synthesis of Compound (7):

A solution of Pd(OAc)$_2$ (97 mg, 0.44 mmol) and tri-tert-butylphosphine (3.6 g, 0.87 mmol, 5% in hexane) in anhydrous toluene (20 mL) was added to a suspension of bis(4-methoxyphenyl)amine (2.00 g, 8.7 mmol), 4'-bromoacetophenone (2.6 g, 13.1 mmol) and sodium tert-butoxide (1.67 g, 17.4 mmol) in anhydrous toluene (50 mL) under nitrogen. The mixture was refluxed for 24 hours. After cooling, the reaction mixture was filtered, followed by removal of all solvents. Then, $CH_2Cl_2$ and water were added, the organic layer was washed with brine and water, and dried over $Na_2SO_4$. The pure product (1.6 g) was obtained by column chromatography using hexane:EA=10:1 as the eluent in a yield of 55%.

Spectral data of compound (7): $^1$H NMR (400 MHz, $CDCl_3$): δ 7.73 (d, J=9.0 Hz, 2H), 7.09 (d, J=9.0 Hz, 4H), 6.86 (d, J=9.0 Hz, 4H), 6.79 (d, J=6.9 Hz, 2H), 3.79 (s, 6H), 2.48 (s, 3H).

Synthesis of Compound (8):

The procedure described for compound (2) was performed, except that different reactants were employed, to obtain a white product of compound (8) in a yield of 63%.

Spectral data of compound (8): $^1$H NMR (400 MHz, acetone-$d_6$): δ 7.71 (d, J=1.9 Hz, 1H), 7.68-7.64 (m, 3H), 7.49 (dd, J=8.2, 2.0 Hz, 1H), 7.07-6.90 (m, 11H), 3.78 (s, 6H), 1.34 (s, 9H).

Synthesis of Compound (9):

The procedure described for compound (3) was performed, except that different reactants were employed, to obtain a white product of compound (9) in a yield of 90%.

Spectral data of compound (9): $^1$H NMR (400 MHz, $CDCl_3$): δ 7.66 (d, J=7.5 Hz, 1H), 7.50-7.46 (m, 3H), 7.39-7.33 (m, 1H), 7.11 (d, J=8.7 Hz, 1H), 7.05-7.03 (m, 3H), 6.94 (d, J=7.5 Hz, 2H), 6.86-6.79 (m, 4H), 6.50 (s, 1H), 5.23-5.20 (m, 1H), 4.17-4.13 (m, 1H), 3.78 (s, 6H), 3.64-3.60 (m, 1H), 2.69-2.62 (m, 1H), 2.08-2.04 (m, 1H), 1.84-1.72 (m, 4H). MS [FAB], m/z 667.3, M$^+$.

Synthesis of Compound (IA-12):

The procedure described for compound (IA-10 was performed, except that different reactants were employed, to obtain a pale yellow product of compound (IA-12) in a yield of 36%.

Spectral data of compound (IA-12): $^1$H NMR (400 MHz, DMSO-$d_6$): δ 7.58 (d, J=8.3 Hz, 2H), 7.56-7.51 (m, 3H), 7.42 (dd, J=8.1, 1.6 Hz, 1H), 6.97-6.96 (m, 4H), 6.88-6.85 (m, 4H), 6.78-6.72 (m, 15H), 6.66-6.63 (m, 8H), 6.09 (s, 1H), 3.70 (s, 6H), 3.60 (s, 12H), 1.16 (s, 9H). MS [FAB], m/z 1119.5, M$^+$. Anal. Calcd. for $C_{74}H_{65}N_5O_6$: C, 79.33; H, 6.25; N, 5.85. Found: C, 78.50; H, 6.24; N, 5.89.

Embodiment 4: Synthesis of Compound (IA-14)

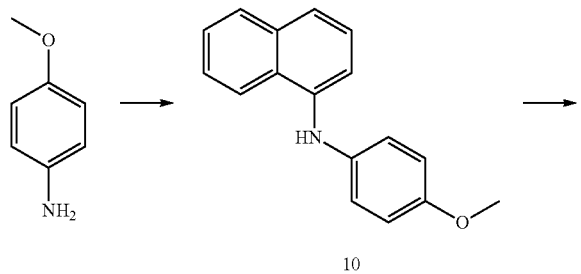

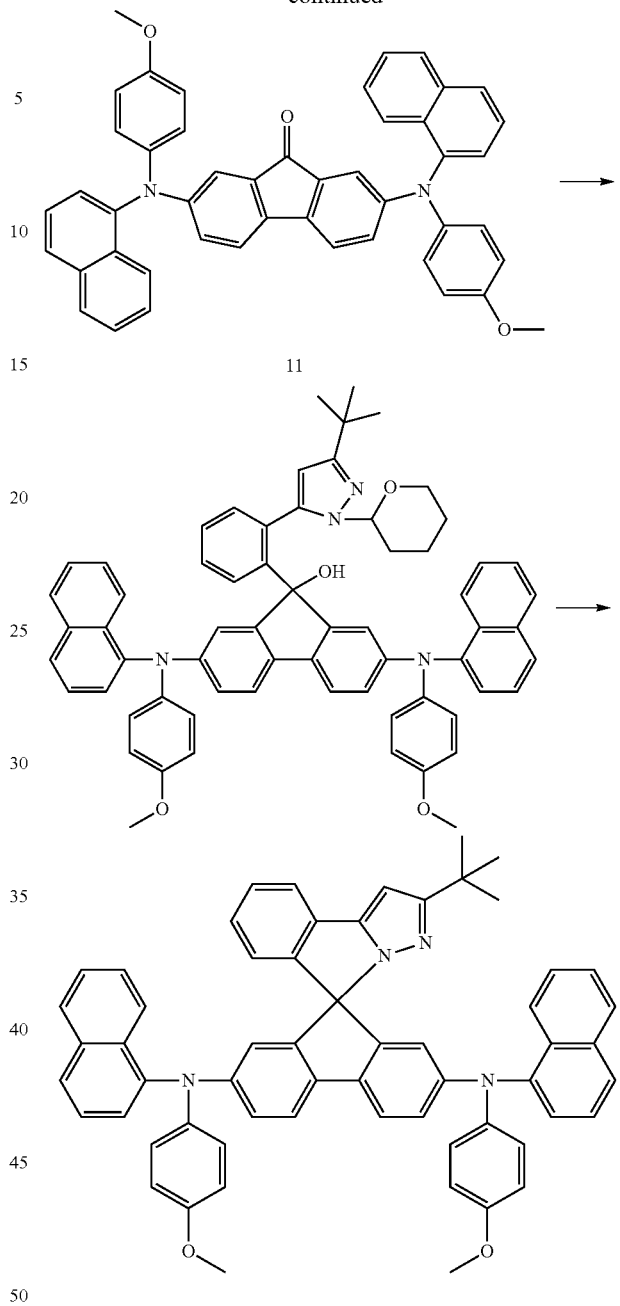

Synthesis of Compound (10):

A solution of 1-bromonaphthalene (1.03 g, 5 mmol), 4-methoxybenzenamine (739 mg, 6 mmol), Pd(OAc)$_2$ (22 mg, 0.1 mmol) and (±)-2,2'-Bis(diphenylphosphino)-1,1'-binaphthalene (BINAP) (99 mg, 0.16 mmol) and $Cs_2CO_3$ (1.95 g, 6 mmol) in anhydrous toluene (25 mL) was heated to reflux for 12 hours under nitrogen. After cooling, the reaction mixture was filtered, followed by removal of all solvent mixture. Then, $CH_2Cl_2$ and water were added, the organic layer was washed with brine and water, dried over $Na_2SO_4$. The pure product (750 mg) was obtained by column chromatography using hexane:EA=6:1 as the eluent in a yield of 60%.

Spectral data of compound (10): $^1$H NMR (400 MHz, $CDCl_3$): δ 7.99 (d, J=9.5 Hz, 1H), 7.83 (d, J=9.4 Hz, 1H), 7.50-7.42 (m, 3H), 7.31 (t, J=7.8 Hz, 1H), 7.10 (d, J=7.5 Hz, 1H), 7.05 (d, J=8.8 Hz, 2H), 6.87 (d, J=8.9 Hz, 2H), 3.81 (s, 3H).

Synthesis of Compound (11):

A solution of 2,7-dibromo-9H-fluoren-9-one (1.2 g, 3.5 mmol), N-(4-methoxyphenyl)naphthalen-1-amine (1.83 g, 7.35 mmol), Pd(dba)$_2$ (200 mg, 0.35 mmol), P(t-Bu)$_3$ (141 mg, 0.7 mmol) and Na$^t$OBu (1.03 g, 10.85 mmol) in anhydrous toluene (30 mL) was heated to reflux for 12 hours under nitrogen. After cooling, the reaction mixture was filtered, followed by removal of all solvent mixture. Then, CH$_2$Cl$_2$ and water were added, the organic layer was washed with brine and water, and finally, dried over Na$_2$SO$_4$. The pure product (1.97 g) was obtained by column chromatography using hexane:EA=5:1 as the eluent in a yield of 83%.

Spectral data of compound (11): $^1$H NMR (400 MHz, CDCl$_3$): δ 7.87 (dd, J=15.1, 8.3 Hz, 4H), 7.73 (d, J=8.1 Hz, 2H), 7.45-7.41 (m, 4H), 7.34-7.32 (m, 2H), 7.25 (d, J=8.1 Hz, 2H), 7.10 (d, J=2.1 Hz, 2H), 7.06-7.02 (m, 6H), 6.79-6.77 (m, 6H), 3.76 (s, 6H).

Synthesis of Compound (IA-14):

The procedure described for compound (IA-10) was performed, except that different reactants were employed, to obtain a pale yellow product of compound (IA-14) in a yield of 36%.

Spectral data of compound (IA-14): $^1$H NMR (400 MHz, DMSO-d$_6$): δ 7.86 (d, J=8.2 Hz, 2H), 7.72 (d, J=8.2 Hz, 2H), 7.65 (d, J=8.5 Hz, 2H), 7.53 (d, J=8.4 Hz, 2H), 7.46 (d, J=7.3 Hz, 1H), 7.42-7.35 (m, 4H), 7.31-7.25 (m, 3H), 7.15-7.11 (m, 3H), 6.81 (d, J=8.8 Hz, 4H), 6.72-6.64 (m, 5H), 6.63 (dd, J=8.3, 2.1 Hz, 2H), 6.20 (s, 1H), 5.92 (d, J=2.0 Hz, 2H), 3.60 (s, 6H), 1.12 (s, 9H). MS [FAB], m/z 856.4 M+. Anal. Calcd. for C$_{60}$H$_{48}$N$_4$O$_2$: C, 84.08; H, 5.65; N, 6.54. Found: C, 83.48; H, 5.71; N, 6.65.

Embodiment 5: Synthesis of Compound (IA-15)

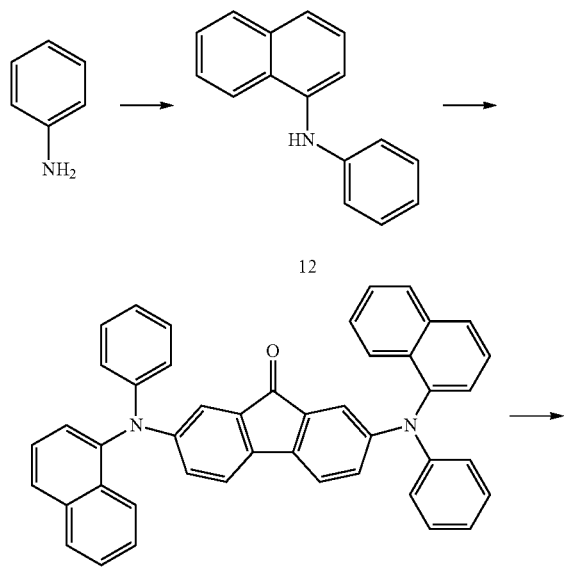

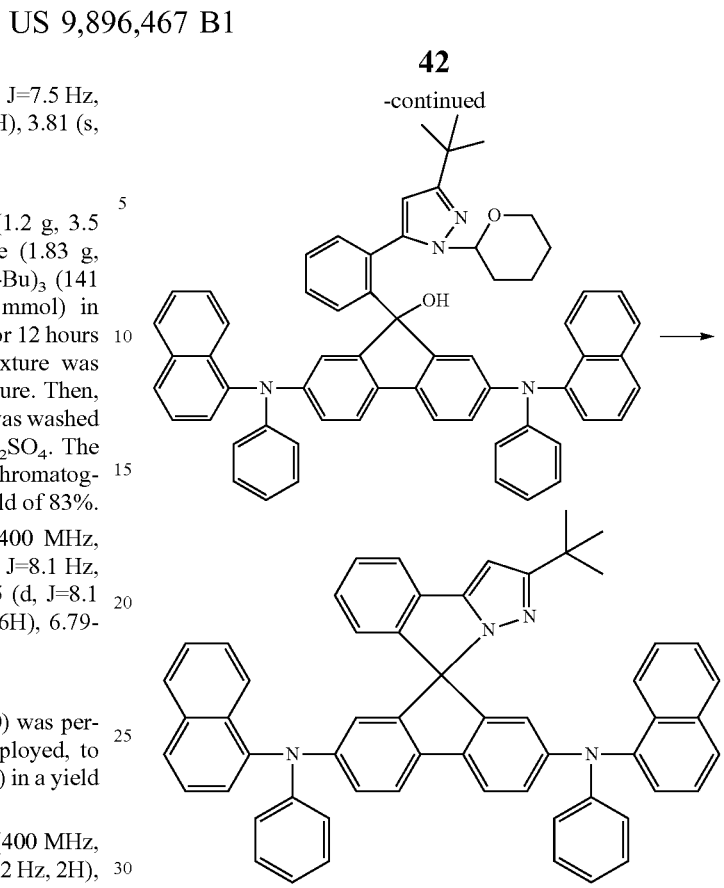

Synthesis of Compound (12):

The procedure described for compound (10) was performed, except that different reactants were employed, to obtain a pure product of compound (12) in a yield of 82%.

Spectral data of compound (12): $^1$H NMR (400 MHz, CDCl$_3$): δ 8.01 (d, J=7.6 Hz, 2H), 7.86 (d, J=7.4 Hz, 2H), 7.56 (d, J=7.3 Hz, 1H), 7.51-7.44 (m, 2H), 7.41-7.37 (m, 2H), 7.27-7.23 (m, 2H), 6.98 (d, J=7.4 Hz, 2H), 6.93-6.88 (m, 1H).

Synthesis of Compound (13):

The procedure described for compound (11) was performed, except that different reactants were employed, to obtain a pure product of compound (13) in a yield of 86%.

Spectral data of compound (13): $^1$H NMR (400 MHz, CDCl$_3$): δ 7.87 (d, J=9.3 Hz, 4H), 7.76 (d, J=8.3 Hz, 2H), 7.47-7.42 (m, 4H), 7.36-7.32 (m, 2H), 7.29 (dd, J=7.3, 1.1 Hz, 2H), 7.23 (d, J=2.2 Hz, 2H), 7.21-7.17 (m, 4H), 7.13 (d, J=8.2 Hz, 2H), 7.02-7.00 (m, 4H), 6.97-6.94 (m, 4H).

Synthesis of Compound (IA-15):

The procedure described for compound (IA-10) was performed, except that different reactants were employed, to obtain a pale yellow product of compound (IA-15) in a yield of 30%.

Spectral data of compound (15): $^1$H NMR (400 MHz, DMSO-d$_6$): δ 7.89 (d, J=8.1 Hz, 2H), 7.78 (d, J=8.1 Hz, 2H), 7.62 (dd, J=8.4, 3.0 Hz, 4H), 7.51 (d, J=7.2 Hz, 1H), 7.42 (t, J=7.7 Hz, 4H), 7.32-7.27 (m, 3H), 7.18-7.14 (m, 3H), 7.05 (t, J=7.7 Hz, 4H), 6.85-6.72 (m, 9H), 6.25 (s, 1H), 6.14 (d, J=2.0 Hz, 2H), 1.14 (s, 9H). MS [FAB], m/z 796.4 M$^+$. Anal. Calcd. for C$_{58}$H$_{44}$N$_4$: C, 87.41; H, 5.56; N, 7.03. Found: C, 87.30; H, 5.60; N, 6.82.

Embodiment 6: Synthesis of Compound (IA-16)

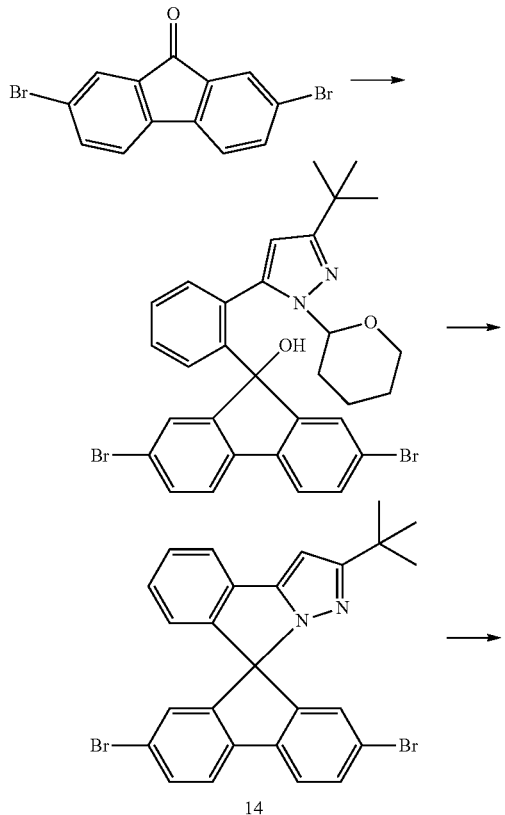

Synthesis of Compound (14):

A solution of 3-tert-butyl-5-(2-bromophenyl)-1-(tetrahydro-2H-pyran-2-yl)-1H-pyrazole (1.7 g, 4.55 mmol) in dry THF (15 mL) was treated with n-BuLi (2.02 mL, 2.5 M in n-hexane) under nitrogen at −78° C. After 30 minutes, a solution of 2,7-dibromo-9H-fluoren-9-one (1.18 g, 3.5 mmol) in THF (10 mL) was added dropwise. The mixture was stirred for 30 minutes at −78° C., and allowed to warm up to room temperature. After stirring for 12 hours, the solution was concentrated and the residue was extracted with $CH_2Cl_2$ and washed with brine and water in sequence and finally dried over $Na_2SO_4$. The intermediate of tertiary alcohol could be obtained by column chromatography using hexane:EA=10:1 as the eluent. Then, the intermediate was added to a mixture of concentrated aqueous HCl (2 mL) and acetic acid (30 mL). After 1 hour of reflux, the reaction was quenched with ice water and neutralized with $NaHCO_3$(aq). The crude product was extracted with $CH_2Cl_2$ and washed with water. The organic layer was dried over anhydrous $Na_2SO_4$ and purified by silica gel column chromatography eluting with hexane:EA=10:1 as the eluent in a yield of 40%.

Spectral data of compound (14): $^1$H NMR (400 MHz, $CDCl_3$): δ 7.64-7.60 (m, 3H), 7.52 (dd, J=8.1, 1.6 Hz, 2H), 7.38 (t, J=7.5 Hz, 1H), 7.12 (t, J=7.5 Hz, 1H), 6.88 (d, J=1.5 Hz, 2H), 6.65 (d, J=7.7 Hz, 1H), 6.38 (s, 1H). MS [EI], m/z 520.0 M$^+$.

Compound (IA-16): A solution of compound (14) (302 mg, 0.58 mmol), 10H-phenothiazine (254 mg, 1.27 mmol), $Pd(dba)_2$ (33 mg, 0.058 mmol), $P(t-Bu)_3$ (23 mg, 0.116 mmol) and Na$^t$OBu (169 mg, 1.79 mmol) in anhydrous toluene (5 mL) was heated to reflux for 12 hours under nitrogen. After cooling, the reaction mixture was filtered, followed by removal of all solvents. Then, $CH_2Cl_2$ and water were added, the organic layer was washed with brine and water, and finally, dried over $Na_2SO_4$. The pure product (359 mg) was obtained by column chromatography using hexane:DCM=2:1 as the eluent in a yield of 82%.

Spectral data of compound (IA-16): $^1$H NMR (400 MHz, $CDCl_3$): δ 8.07 (d, J=7.9 Hz, 2H), 7.57 (d, J=7.5 Hz, 1H), 7.50 (d, J=7.8 Hz, 2H), 7.35 (t, J=7.5 Hz, 1H), 7.15 (t, J=7.6 Hz, 1H), 6.97-6.89 (m, 7H), 6.77 (br, 8H), 6.28 (s, 1H), 6.15-6.14 (br, 4H), 1.24 (s, 9H). MS [EI], m/z 756.2 M$^+$. Anal. Calcd. for $C_{50}H_{36}N_4S_2$: C, 79.33; H, 4.79; N, 7.40. Found: C, 79.40; H, 4.80; N, 7.20.

Embodiment 7: Synthesis of Compound (IA-17)

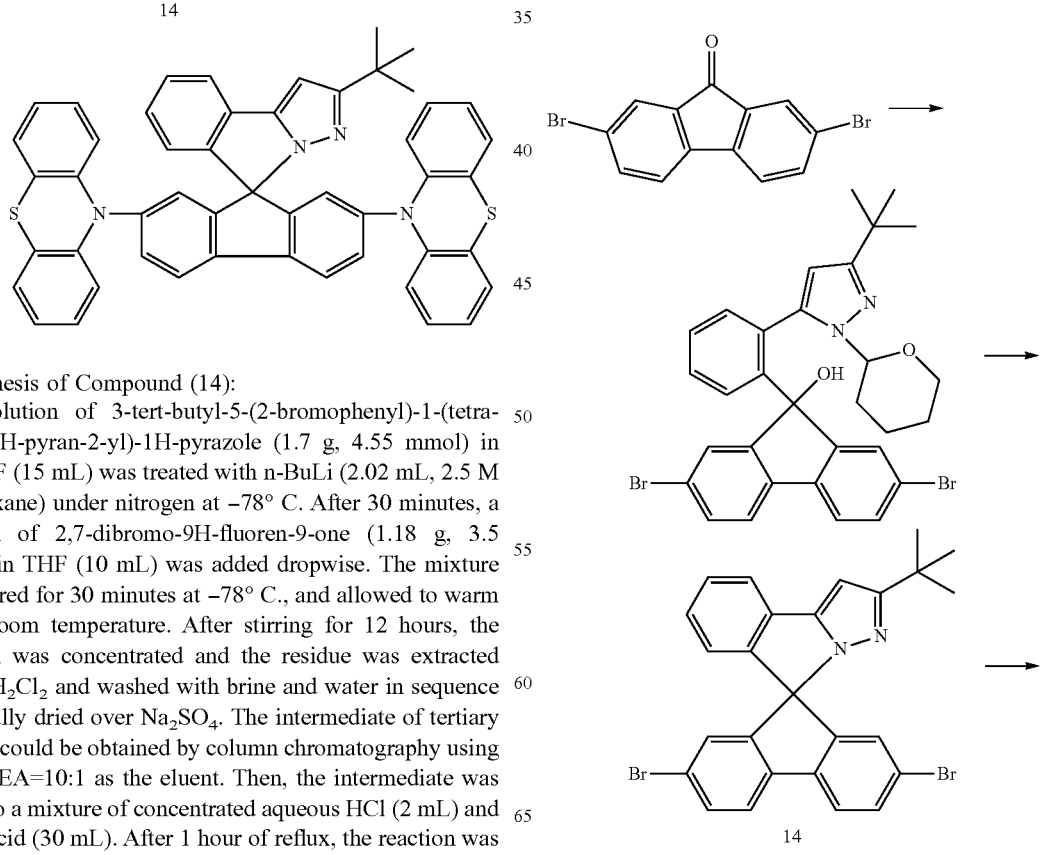

-continued

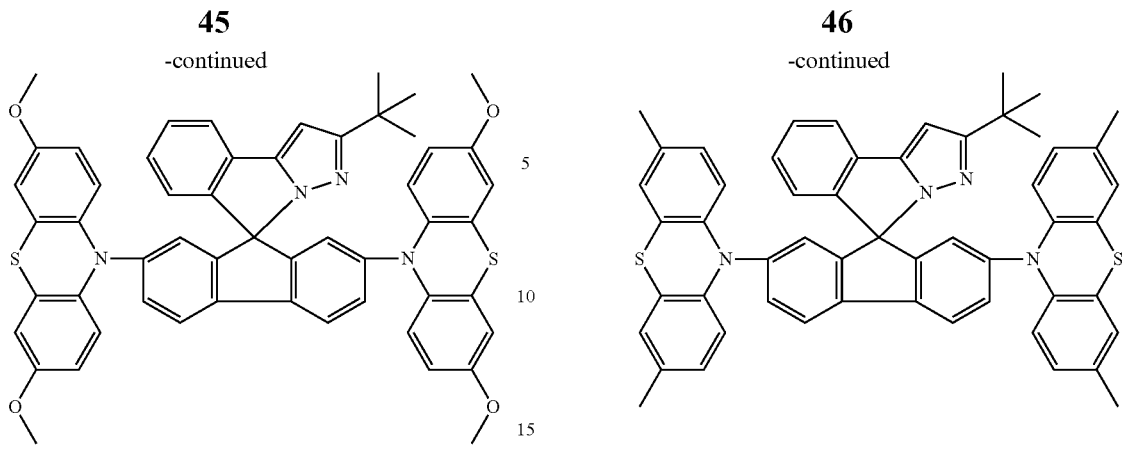

Synthesis of Compound (IA-17):

The procedure described for compound (IA-16) was performed, except that different reactants were employed, to obtain a pure product of compound (IA-17) in a yield of 78%.

Spectral data of compound (IA-17): $^1$H NMR (400 MHz, DMSO-$d_6$): δ 7.98 (d, J=8.2 Hz, 2H), 7.68 (d, J=7.5 Hz, 1H), 7.36 (t, J=7.6 Hz, 1H), 7.21 (dd, J=8.3, 1.9 Hz, 2H), 7.15 (td, J=7.6, 1.0 Hz, 1H), 6.79-6.76 (m, 5H), 6.56 (dd, J=8.9, 2.6 Hz, 4H), 6.49 (d, J=8.9 Hz, 4H), 6.41 (s, 1H), 6.28 (d, J=1.8 Hz, 2H), 3.63 (s, 12H), 1.10 (s, 9H). MS [EI], m/z 876.2 M$^+$. Anal. Calcd. for $C_{54}H_{44}N_4O_4S_2$: C, 73.95; H, 5.06; N, 6.39. Found: C, 73.90; H, 5.00; N, 6.30.

Embodiment 8: Synthesis of Compound (IA-18)

Synthesis of Compound (IA-18):

The procedure described for compound (IA-16) was performed, except that different reactants were employed, to obtain a pure product of compound (IA-18) in a yield of 80%.

Spectral data of compound (IA-18): $^1$H NMR (400 MHz, $CD_2Cl_2$): δ 8.07-8.05 (m, 2H), 7.62-7.59 (m, 1H), 7.46 (br, 2H), 7.39-7.34 (m, 1H), 7.20-7.16 (m, 1H), 6.95-6.91 (m, 1H), 6.80 (br, 6H), 6.61 (br, 4H), 6.31 (s, 1H), 6.10 (br, 4H), 2.14 (s, 12H), 1.24 (s, 9H). MS [FAB], m/z 812.3 M$^+$. Anal. Calcd. for $C_{54}H_{46}N_4S_2$: C, 79.77; H, 5.45; N, 6.89. Found: C, 79.70; H, 5.51; N, 6.81.

Embodiment 9: Synthesis of Compound (IA-13)

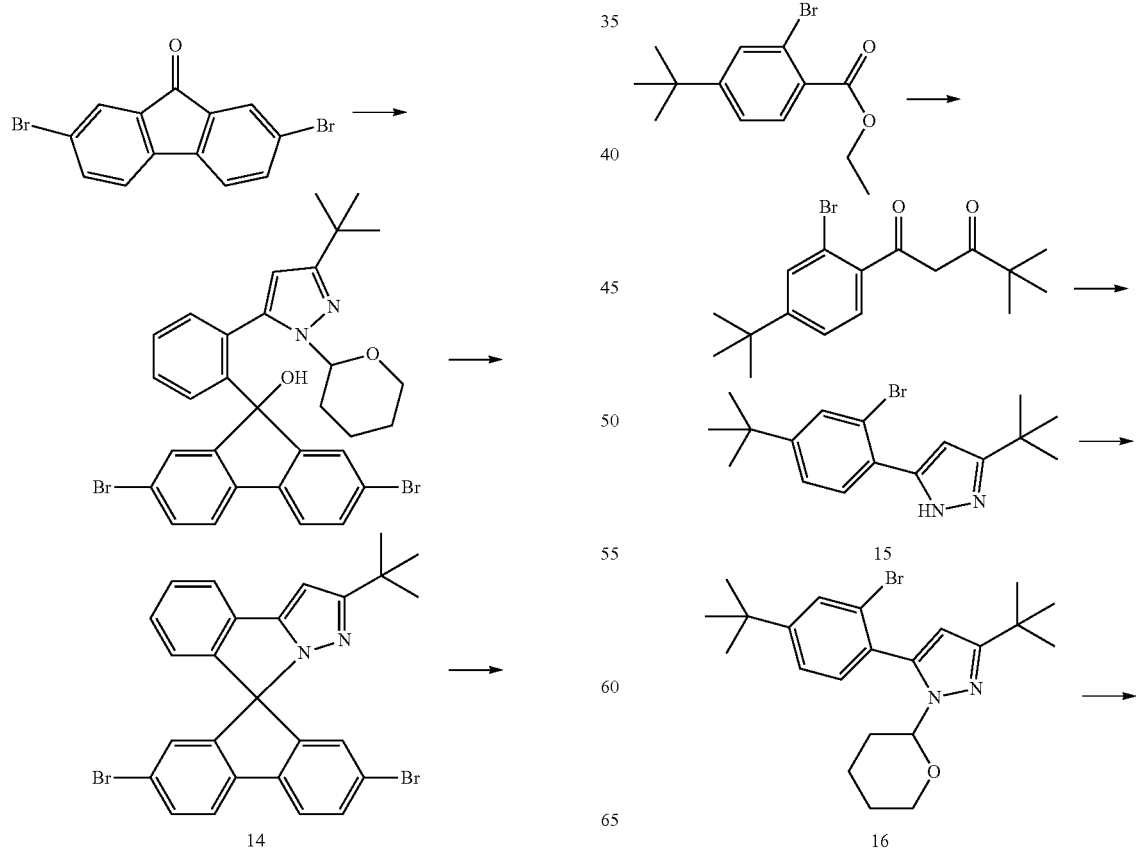

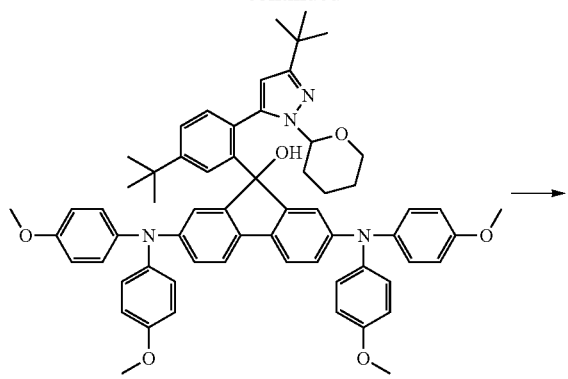

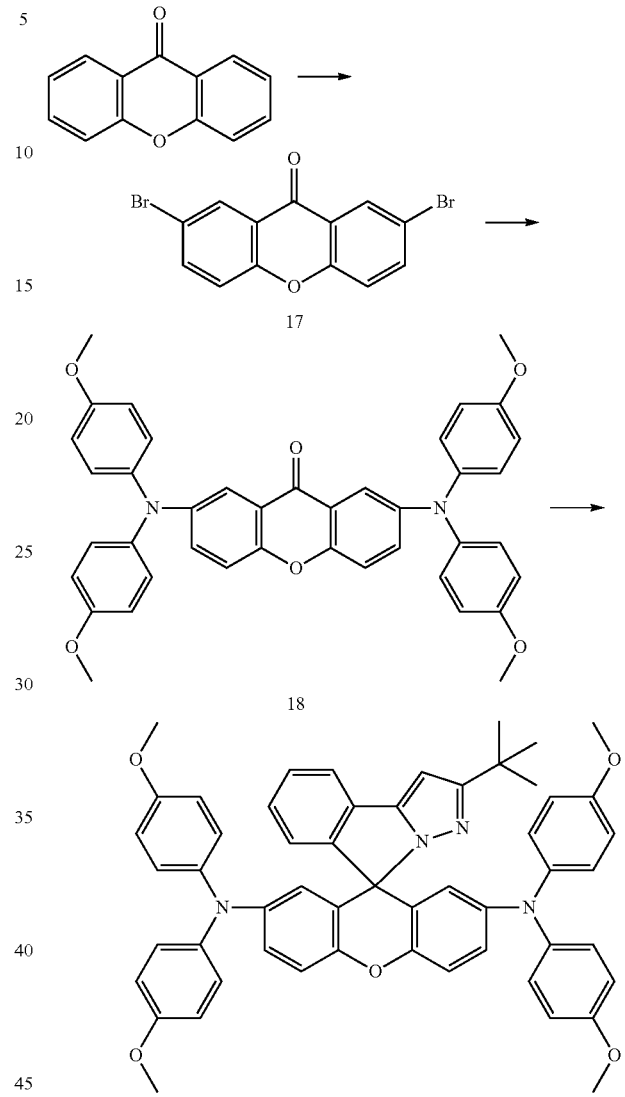

Synthesis of Compound (15):

The procedure described for compound (2) was performed, except that different reactants were employed, to obtain a pure product of compound (15) in a yield of 70%.

Spectral data of compound (15): $^1$H NMR (400 MHz, CDCl$_3$): δ 7.62 (d, J=1.7 Hz, 1H), 7.50 (dd, J=8.2, 2.3 Hz, 1H), 7.34 (dd, J=8.2, 2.0 Hz, 1H), 6.45 (s, 1H), 1.36 (s, 9H), 1.31 (s, 9H).

Synthesis of Compound (16):

The procedure described for compound (3) was performed, except that different reactants were employed, to obtain a pure product of compound (16) in a yield of 82%.

Spectral data of compound (16): $^1$H NMR (400 MHz, CDCl$_3$): δ 7.65-7.64 (m, 1H), 7.35 (d, J=1.1 Hz, 2H), 6.14 (s, 1H), 4.92-4.88 (m, 1H), 4.00-3.95 (m, 1H), 3.43-3.37 (m, 1H), 2.49-2.41 (m, 1H), 2.05-1.98 (m, 1H), 1.91-1.83 (m, 4H), 1.34 (s, 9H), 1.32 (s, 9H).

Synthesis of Compound (IA-13):

The procedure described for compound (IA-10) was performed, except that different reactants were employed, to obtain a pure product of compound (IA-13) in a yield of 40%.

Spectral data of compound (IA-13): $^1$H NMR (400 MHz, DMSO-d$_6$): δ 7.58 (d, J=8.3 Hz, 2H), 7.49 (d, J=8.1 Hz, 1H), 7.39 (dd, J=8.1, 1.7 Hz, 1H), 6.80-6.75 (m, 9H), 6.74-6.70 (m, 9H), 6.67 (d, J=1.7 Hz, 1H), 6.28 (s, 1H), 6.03 (d, J=2.2 Hz, 2H), 3.64 (s, 12H), 1.18 (s, 9H), 1.15 (s, 9H). MS [EI], m/z 872.4 M$^+$. Anal. Calcd. for C$_{58}$H$_{56}$N$_4$O$_4$: C, 79.79; H, 6.46; N, 6.42. Found: C, 79.90; H, 6.64; N, 6.31.

Embodiment 10: Synthesis of Compound (IA-19)

Synthesis of Compound (17):

9H-xanthen-9-one (5 g, 25 mmol) was dissolved in 50 mL of acetic acid, and 10 mL of Br$_2$ was added dropwise at room temperature and heated to reflux for 20 hours. After that, the mixture was cooled and poured into ice water. The precipitate was washed with saturated solution of NaHCO$_3$, 20% aqueous solution of NaHSO$_3$, and water in sequence. The solid product was dried under vacuum and recrystallized in toluene to give yellow solid 6.1 g with a yield of 69%.

Spectral data of compound (17): $^1$H NMR (400 MHz, CDCl$_3$): δ 8.41 (d, J=1.7 Hz, 2H), 7.79 (d, J=9.0, 1.6 Hz, 2H), 7.38 (dd, J=8.9 Hz, 2H).

Synthesis of Compound (18):

A solution of compound (17) (708 mg, 2 mmol), bis(4-methoxyphenyl)amine (983 mg, 4.2 mmol), Pd(dba)$_2$ (114 mg, 0.2 mmol), P(t-Bu)$_3$ (81 mg, 0.4 mmol) and Na$^t$OBu (588 mg, 6.2 mmol) in anhydrous toluene (15 mL) was heated to reflux for 12 hours under nitrogen. After cooling, the reaction mixture was filtered, followed by removal of all volatile components. Then, CH$_2$Cl$_2$ and water were added, the organic layer was washed with brine and water in sequence, and dried over Na$_2$SO$_4$. The pure product (1.22 g) can be obtained by column chromatography using hexane: CH$_2$Cl$_2$=1:1 as the eluent in a yield of 94%.

Spectral data of compound (18): $^1$H NMR (400 MHz, CDCl$_3$): δ 7.74 (d, J=2.7 Hz, 2H), 7.34 (dd, J=9.1, 2.8 Hz, 2H), 7.28 (d, J=9.1 Hz, 2H), 7.02 (d, J=9.0 Hz, 8H), 6.81 (d, J=9.0 Hz, 8H), 3.82 (s, 12H).

Synthesis of Compound (IA-19):

The procedure described for compound (IA-10) was performed, except that different reactants were employed, to obtain a pure product of compound (IA-19) in a yield of 35%.

Spectral data of compound (IA-19): $^1$H NMR (400 MHz, DMSO-d$_6$): δ 7.54 (d, J=7.9 Hz, 1H), 7.36-7.27 (m, 1H), 7.23-7.19 (m, 3H), 7.02 (d, J=8.1 Hz, 1H), 6.75 (dd, J=8.9, 2.8 Hz, 2H), 6.70 (s, 16H), 6.26 (s, 1H), 5.73 (d, J=2.7 Hz, 2H), 3.64 (s, 12H), 1.11 (s, 9H). MS [FAB], m/z 832.4 M$^+$. Anal. Calcd. for C$_{54}$H$_{48}$N$_4$O$_5$: C, 77.86; H, 5.81; N, 6.73. Found: C, 78.01; H, 5.90; N, 6.70.

Embodiment 11: Synthesis of Compound (IA-20)

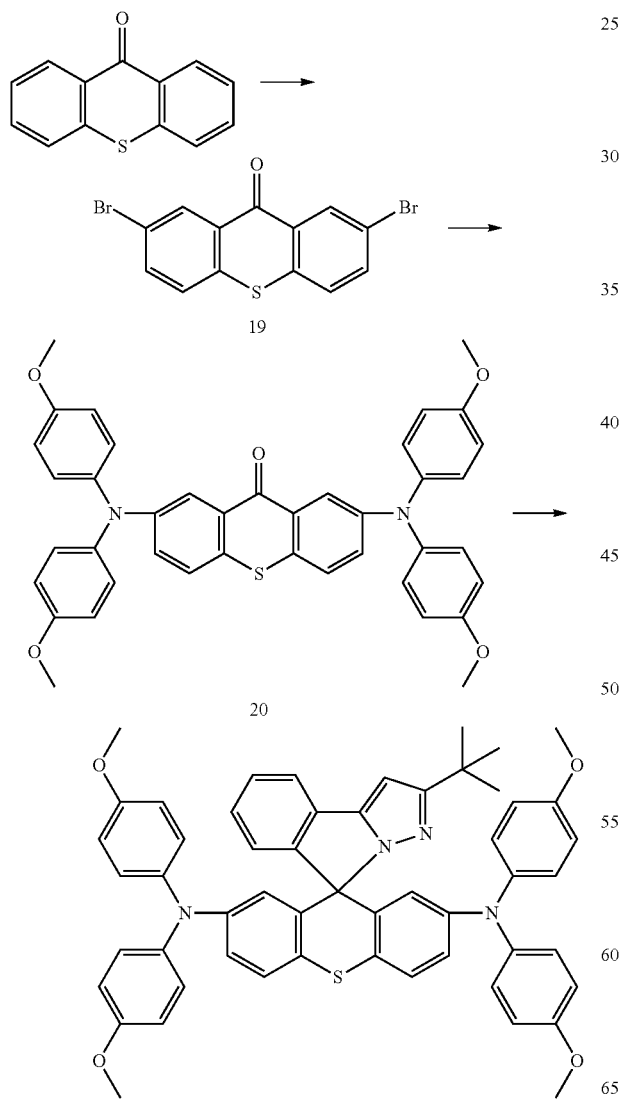

Synthesis of Compound (19):

The procedure described for compound (17) was performed, except that different reactants were employed, to obtain a pure product of compound (19) in a yield of 74%.

Spectral data of compound (19): $^1$H NMR (400 MHz, CDCl$_3$): δ 8.72 (dd, J=2.3, 0.9 Hz, 2H), 7.72 (ddd, J=8.6, 2.3, 1.2 Hz, 2H), 7.45 (dd, J=8.6, 0.8 Hz, 2H).

Synthesis of Compound (20):

The procedure described for compound (18) was performed, except that different reactants were employed, to obtain a pure product of compound (20) in a yield of 92%.

Spectral data of compound (20): $^1$H NMR (400 MHz, CDCl$_3$): δ 8.00 (d, J=2.0 Hz, 2H), 7.33 (d, J=8.8 Hz, 2H), 7.24 (dd, J=8.4, 3.0 Hz, 2H), 7.04 (d, J=8.8 Hz, 8H), 6.81 (d, J=8.9 Hz, 8H), 3.77 (s, 12H).

Synthesis of Compound (IA-20):

The procedure described for compound (IA-10) was performed, except that different reactants were employed, to obtain a pure product of compound (IA-20) in a yield of 54%.

Spectral data of compound (IA-20): $^1$H NMR (400 MHz, DMSO-d$_6$): δ 7.90 (d, J 7.8 Hz, 1H), 7.57 (d, J=7.5 Hz, 1H), 7.35 (d, J=8.6 Hz, 2H), 7.31 (d, J=7.5 Hz, 1H), 7.14 (t, J=7.7 Hz, 1H), 6.74 (s, 16H), 6.66 (dd, J=8.5, 2.5 Hz, 2H), 6.23 (s, 1H), 5.66 (d, J=2.4 Hz, 2H), 3.61 (s, 12H), 0.94 (s, 9H). MS [FAB], m/z 848.4 M$^+$. Anal. Calcd. for C$_{54}$H$_{48}$N$_4$O$_4$S: C, 76.39; H, 5.70; N, 6.60. Found: C, 76.13; H, 5.57; N, 6.60.

Embodiment 12: Synthesis of Compound (IA-21)

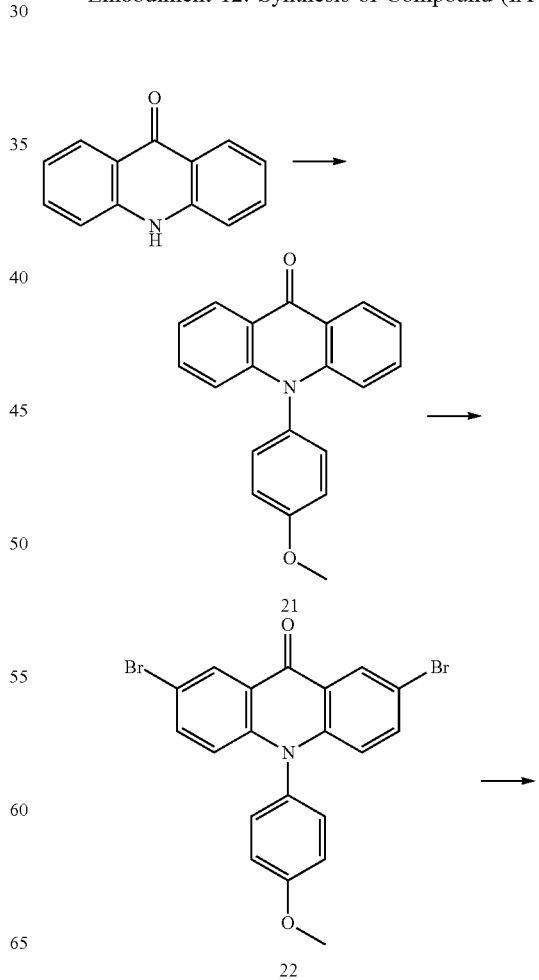

-continued

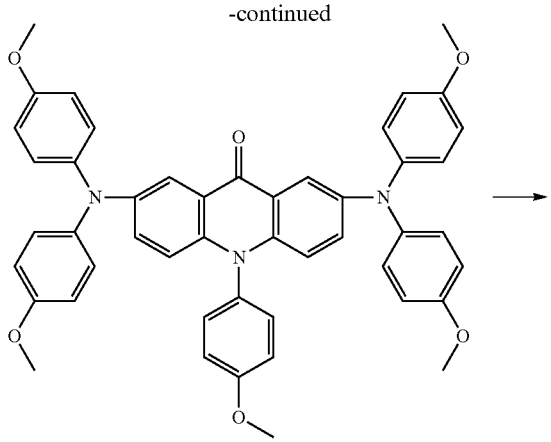

23

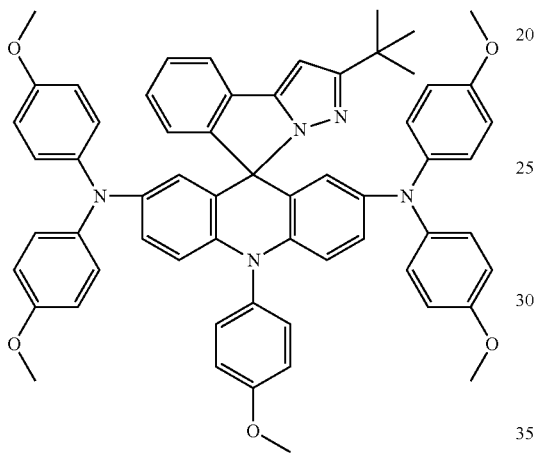

Synthesis of Compound (21):

A solution of acridin-9(10H)-one (2.93 g, 15 mmol), 4-iodoanisole (5.4 g, 22.5 mmol), CuI (278 mg, 1.5 mmol), K$_2$CO$_3$ (3.09 g, 22.5 mmol) and 2,2,6,6-tetramethylheptane-3,5-dione (627 µL, 3 mmol) in anhydrous DMF (35 mL) was heated to reflux for 20 h under nitrogen. After cooling, the reaction mixture was poured into water, filtered and washed with water, and finally, dried under vacuum. The pure product (4 g) can be obtained by column chromatography using hexane:CH$_2$Cl$_2$=3:1 as the eluent in a yield of 89%.

Spectral data of compound (21): $^1$H NMR (400 MHz, CDCl$_3$): δ 8.56 (ddd, J=8.0, 1.7, 0.5 Hz, 2H), 7.51-7.46 (m, 2H), 7.27-7.23 (m, 4H), 7.18-7.16 (m, 2H), 6.80 (d, J=10.1 Hz, 2H), 3.94 (s, 3H).

Synthesis of Compound (22):

Compound (21) (903 mg, 3 mmol) was dissolved in 27 mL of DMF, and 9 mL of NBS (1.12 g, 6.3 mmol) in DMF was added dropwise at 0° C. and then heated to 80° C. for 6 hours. After that, the mixture was cooled and poured into water, filtered, washed with water, ethanol and hot hexane in sequence. Finally, the solid was dried under vacuum to obtain yellow product (1.2 g) with a yield of 88%.

Spectral data of compound (22): $^1$H NMR (400 MHz, CDCl$_3$): δ 8.61 (d, J=2.4 Hz, 1H), 7.54 (dd, J=9.1, 2.5 Hz, 2H), 7.25-7.22 (m, 3H), 7.18 (d, J=9.0 Hz, 2H), 6.69 (dd, J=9.1, 2.8 Hz, 2H), 3.94 (s, 3H).

Synthesis of Compound (23):

The procedure described for compound (18) was performed, except that different reactants were employed, to obtain a pure product of compound (23) in a yield of 87%.

Spectral data of compound (23): $^1$H NMR (400 MHz, DMSO-d$_6$): δ 7.59 (d, J=2.5 Hz, 2H), 7.39 (d, J=8.8 Hz, 2H), 7.22-7.17 (m, 4H), 6.93 (d, J=8.9 Hz, 8H), 6.85 (d, J=8.9 Hz, 8H), 6.65 (d, J=9.3 Hz, 2H), 3.84 (s, 3H), 3.69 (s, 12H).

Synthesis of Compound (IA-21):

The procedure described for compound (IA-10) was performed, except that different reactants were employed, to obtain a pure product of compound (IA-21) in a yield of 40%.

Spectral data of compound (IA-21): $^1$H NMR (400 MHz, DMSO-d$_6$): δ 7.54 (d, J=7.6 Hz, 1H), 7.48 (d, J=8.6 Hz, 2H), 7.36-7.29 (m, 2H), 7.25-7.22 (m, 3H), 6.66-6.59 (m, 18H), 6.27 (d, J=8.9 Hz, 2H), 6.25 (s, 1H), 5.71 (d, J=2.6 Hz, 2H), 3.84 (s, 3H), 3.61 (s, 12H), 1.07 (s, 9H). MS [FAB], m/z 937.4 M$^+$. Anal. Calcd. for C$_{61}$H$_{55}$N$_5$O$_5$: C, 78.10; H, 5.91; N, 7.47. Found: C, 77.85; H, 5.70; N, 7.35.

Embodiment 13: Synthesis of Compound (IA-22)

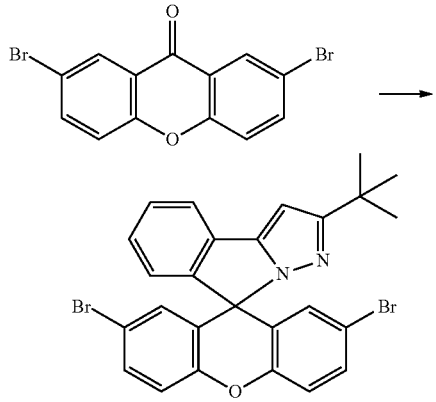

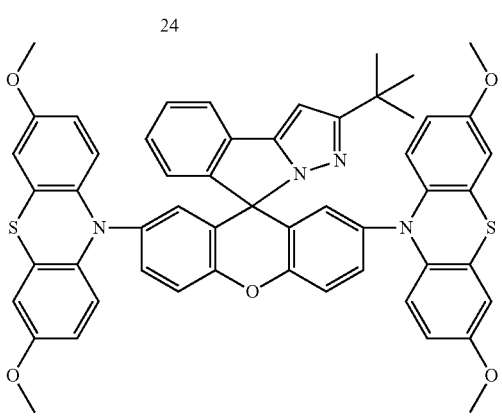

Synthesis of Compound (24):

The procedure described for compound (14) was performed, except that different reactants were employed, to obtain a pure product of compound (24) in a yield of 20%.

Spectral data of compound (24): $^1$H NMR (400 MHz, CDCl$_3$): δ 7.59 (d, J=7.6 Hz, 1H), 7.38-7.31 (m, 3H), 7.16-7.12 (m, 3H), 6.94 (d, J=7.7 Hz, 1H), 6.45 (d, J=2.3 Hz, 2H), 6.42 (s, 1H), 1.34 (s, 9H). MS [FAB], m/z 536.0 M$^+$.

Synthesis of Compound (IA-22):

The procedure described for compound (IA-16) was performed, except that different reactants were employed, to obtain a pure product of compound (IA-22) in a yield of 70%.

Spectral data of compound (IA-22): $^1$H NMR (400 MHz, DMSO-d$_6$): δ 7.66 (d, J=7.5 Hz, 1H), 7.50 (d, J=8.8 Hz, 2H), 7.37 (t, J=7.8 Hz, 1H), 7.23 (t, J=7.6 Hz, 1H), 7.17 (dd, J=8.9, 2.5 Hz, 2H), 7.11 (d, J=7.3 Hz, 1H), 6.74 (d, J=2.7 Hz, 4H), 6.48 (dd, J=8.9, 2.7 Hz, 4H), 6.40 (s, 1H), 6.26 (d, J=8.9 Hz, 4H), 5.99 (d, J=2.5 Hz, 2H), 3.62 (s, 12H), 1.09 (s, 9H). MS [FAB], m/z 892.2 M$^+$. Anal. Calcd. for C$_{54}$H$_{44}$N$_4$O$_5$S$_2$: C, 72.62; H, 4.97; N, 6.27. Found: C, 72.57; H, 4.90; N, 6.20.

Embodiment 14: Synthesis of Compound (IA-23)

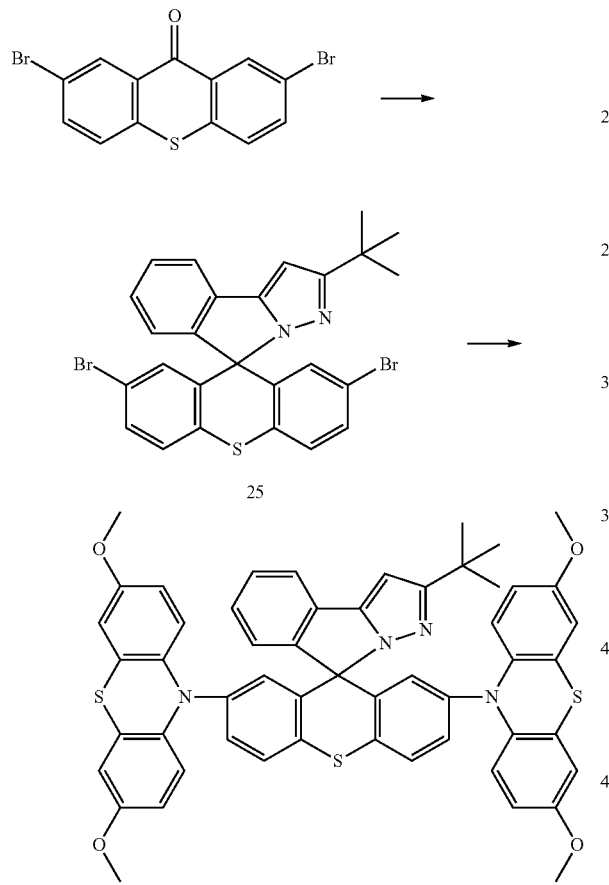

Synthesis of Compound (25):

The procedure described for compound (14) was performed, except that different reactants were employed, to obtain a pure product of compound (25) in a yield of 22%.

Spectral data of compound (25): $^1$H NMR (400 MHz, CDCl$_3$): δ 7.83 (d, J=7.3 Hz, 1H), 7.56 (d, J=7.6 Hz, 1H), 7.34-7.28 (m, 5H), 7.06 (t, J=8.2 Hz, 1H), 6.50 (s, 1H), 6.35 (d, J=1.5 Hz, 2H), 1.43 (s, 9H). MS [FAB], m/z 551.9 M$^+$.

Synthesis of Compound (IA-23):

The procedure described for compound (IA-16) was performed, except that different reactants were employed, to obtain a pure product of compound (IA-23) in a yield of 82%.

Spectral data of compound (IA-23): $^1$H NMR (400 MHz, DMSO-d$_6$): δ 7.71 (d, J=7.7 Hz, 1H), 7.65 (d, J=7.8 Hz, 1H), 7.51 (d, J=8.5 Hz, 2H), 7.33 (t, J=8.2 Hz, 1H), 7.15 (t, J=7.7 Hz, 1H), 6.93 (d, J=8.7 Hz, 2H), 6.85 (s, 4H), 6.60 (s, 8H), 6.42 (s, 1H), 5.82 (br, 2H), 3.66 (s, 12H), 1.01 (s, 9H). MS [FAB], m/z 908.2 M$^+$. Anal. Calcd. for C$_{54}$H$_{44}$N$_4$O$_4$S$_3$: C, 71.34; H, 4.88; N, 6.16. Found: C, 71.20; H, 4.90; N, 6.10.

Embodiment 15: Synthesis of Compound (IA-1)

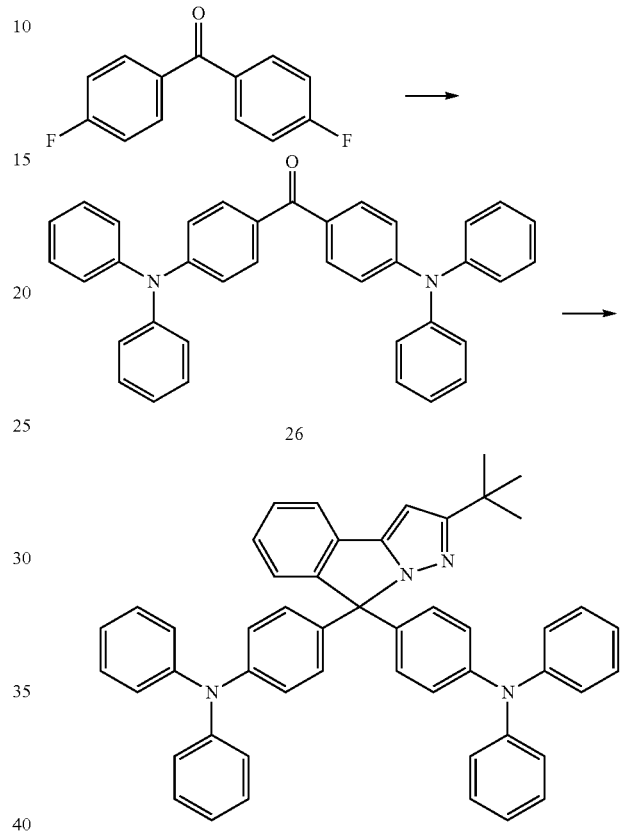

Synthesis of Compound (26):

(1.2 g, 12.49 mmol) were dissolved in 25 mL of anhydrous dimethylformamide under N$_2$ atmosphere. Then, bis(4-fluorophenyl)methanone (0.86 g, 3.94 mmol) in 15 mL of anhydrous dimethylformamide solution was slowly added. The reaction mixture was refluxed for 12 hours. Upon cooling, the mixture was poured into water, filtered, and dried under vacuum. The pure product was obtained by recrystallization from hexane:DCM=5:1 in a yield of 70%.

Spectral data of compound (26): $^1$H NMR (400 MHz, CDCl$_3$): δ 7.68-7.64 (m, 4H), 7.32-7.27 (m, 7H), 7.25-7.23 (m, 1H), 7.16-7.07 (m, 12H), 7.02-6.98 (m, 4H).

Synthesis of Compound (IA-1):

The procedure described for compound (IA-10) was performed, except that different reactants were employed, to obtain a pure product of compound (IA-1) in a yield of 34%.

Spectral data of compound (IA-1): H NMR (400 MHz, DMSO-d$_6$): δ 7.67 (d, J=7.0 Hz, 1H), 7.53 (d, J=7.5 Hz, 1H), 7.40 (td, J=7.5, 1.1 Hz, 1H), 7.34 (td, J=7.5, 1.2 Hz, 1H), 7.27-7.22 (m, 8H), 7.02-6.95 (m, 16H), 6.84 (d, J=8.9 Hz, 4H), 6.44 (s, 1H), 1.25 (s, 9H). MS [FAB], m/z 698.3 M$^+$. Anal. Calcd. for C$_{50}$H$_{42}$N$_4$: C, 85.93; H, 6.06; N, 8.02. Found: C, 85.91; H, 6.10; N, 8.01.

Embodiment 16: Synthesis of Compound (IA-2)

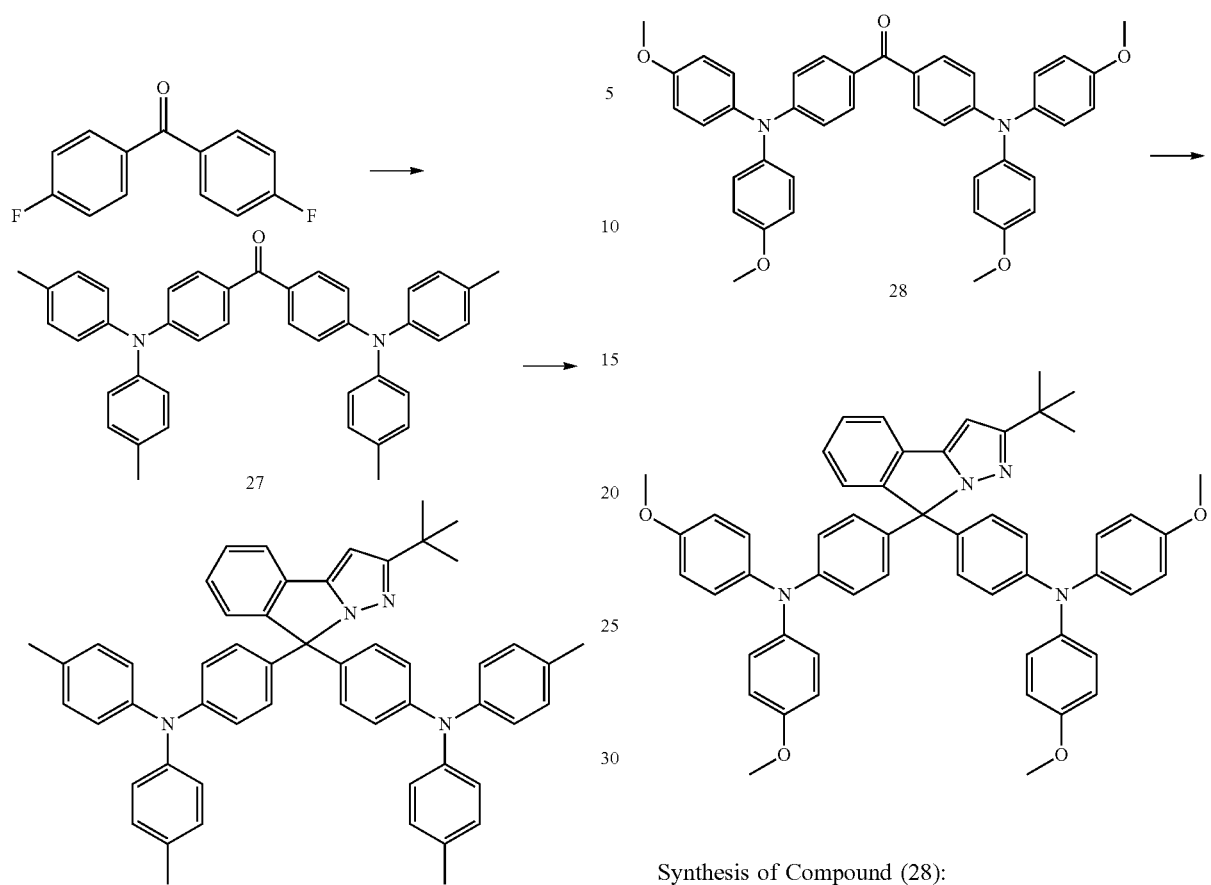

Synthesis of Compound (27):

The procedure described for compound (26) was performed, except that different reactants were employed, to obtain a pure product of compound (27) in a yield of 64%.

Spectral data of compound (27): $^1$H NMR (400 MHz, CDCl$_3$): δ 7.63 (d, J=8.6 Hz, 4H), 7.10 (d, J=7.7 Hz, 8H), 7.04 (d, J=8.2 Hz, 8H), 6.92 (d, J=8.0 Hz, 4H), 2.32 (s, 12H).

Synthesis of Compound (IA-2):

The procedure described for compound (IA-10) was performed, except that different reactants were employed, to obtain a pure product of compound (IA-2) in a yield of 44%.

Spectral data of compound (IA-2): $^1$H NMR (400 MHz, DMSO-d$_6$): δ 7.65 (d, J=7.5 Hz, 1H), 7.48 (d, J=7.6 Hz, 1H), 7.38 (t, J=7.5 Hz, 1H), 7.31 (t, J=7.5 Hz, 1H), 7.05 (d, J=8.2 Hz, 8H), 6.92 (d, J=8.7 Hz, 4H), 6.85 (d, J=8.2 Hz, 8H), 6.74 (d, J=8.7 Hz, 4H), 6.42 (s, 1H), 2.20 (s, 12H), 1.24 (s, 9H). MS [FAB], m/z 754.4 M$^+$. Anal. Calcd. for C$_{54}$H$_{50}$N$_4$: C, 85.90; H, 6.68; N, 7.42. Found: C, 85.89; H, 6.70; N, 7.42.

Synthesis of Compound (28):

The procedure described for compound (26) was performed, except that different reactants were employed, to obtain a pure product of compound (28) in a yield of 76%.

Spectral data of compound (28): $^1$H NMR (400 MHz, CDCl$_3$): δ 7.61 (d, J=7.7 Hz, 4H), 7.10 (d, J=8.9 Hz, 8H), 6.85 (d, J=9.0 Hz, 10H), 6.81 (d, J=1.0 Hz, 2H), 3.79 (s, 12H).

Synthesis of Compound (IA-3):

The procedure described for compound (IA-10) was performed, except that different reactants were employed, to obtain a pure product of compound (IA-3) in a yield of 43%.

Spectral data of compound (IA-3): $^1$H NMR (400 MHz, DMSO-d$_6$): δ 7.64 (d, J=7.4 Hz, 1H), 7.44 (d, J=7.6 Hz, 1H), 7.38-7.35 (m, 1H), 7.31-7.27 (m, 1H), 6.98-6.94 (m, 8H), 6.87-6.82 (m, 12H), 6.59 (d, J=8.9 Hz, 4H), 6.40 (s, 1H), 3.68 (s, 12H), 1.23 (s, 9H). MS [FAB], m/z 818.4 M$^+$. Anal. Calcd. for C$_{54}$H$_{50}$N$_4$O$_4$: C, 79.19; H, 6.15; N, 6.84. Found: C, 79.20; H, 6.13; N, 6.83.

Embodiment 17: Synthesis of Compound (IA-3)

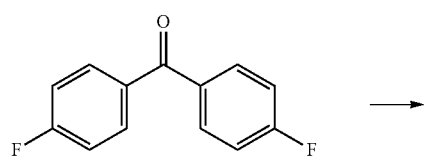

Embodiment 18: Synthesis of Compound (IA-4)

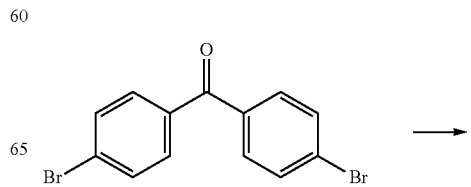

57
-continued

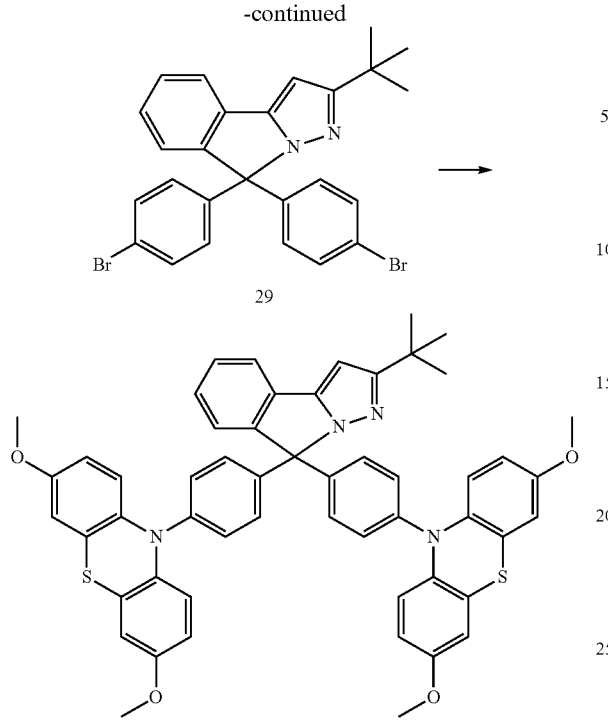

Synthesis of Compound (29):

A solution of 3-tert-butyl-5-(2-bromophenyl)-1-(tetrahydro-2H-pyran-2-yl)-1H-pyrazole (673 mg, 1.8 mmol) in dry THF (7 mL) was treated with n-BuLi (742 μL, 2.5 M in n-hexane) under nitrogen at −78° C. After 30 minutes, a solution of 2,7-dibromo-9H-fluoren-9-one (425 mg, 1.25 mmol) in THF (6 mL) was added dropwise. The mixture was stirred for 30 minutes at −78° C., and allowed to warm up to room temperature. After stirring for 12 hours, the solution was concentrated and the residue was extracted with $CH_2Cl_2$ and washed with brine and water in sequence and finally dried over $Na_2SO_4$. The intermediate of tertiary alcohol could be obtained by column chromatography using hexane:EA=8:1 as the eluent. Then, the intermediate was added to a mixture of concentrated aqueous HCl (1.5 mL) and acetic acid (15 mL). After stirring at room temperature for 1 hour, the reaction was quenched with ice water and neutralized with $NaHCO_3$(aq). The crude product was extracted with $CH_2Cl_2$ and washed with water. The organic layer was dried over anhydrous $Na_2SO_4$ and purified by silica gel column chromatography eluting with hexane:EA=12:1 as the eluent in a yield of 40%.

Spectral data of compound (29): $^1$H NMR (400 MHz, DMSO-$d_6$): δ 7.72 (d, J=7.4 Hz, 1H), 7.56-7.52 (min, 5H), 7.45 (t, J=7.5 Hz, 1H), 7.36 (t, J=8.1 Hz, 1H), 7.02 (d, J=8.6 Hz, 4H), 6.49 (s, 1H), 1.25 (s, 9H). MS [FAB], m/z 522.0 M$^+$.

Synthesis of Compound (IA-4):

The procedure described for compound (IA-16) was performed, except that different reactants were employed, to obtain a pure product of compound (IA-4) in a yield of 79%.

Spectral data of compound (IA-4): $^1$H NMR (400 MHz, DMSO-$d_6$): δ 7.66 (d, J=7.3 Hz, 1H), 7.48 (d, J=7.7 Hz, 1H), 7.38 (t, J=7.4 Hz, 1H), 7.29 (t, J=7.6 Hz, 1H), 6.99-6.93 (m, 12H), 6.85 (d, J=8.8 Hz, 4H), 6.77 (dd, J=8.8, 2.8 Hz, 4H), 6.42 (s, 1H), 3.69 (s, 12H), 1.24 (s, 9H). MS [FAB], m/z 878.3 M$^+$. Anal. Calcd. for $C_{54}H_{46}N_4O_4S_2$: C, 73.78; H, 5.27; N, 6.37. Found: C, 73.88; H, 5.30; N, 6.25.

58

Embodiment 19: Synthesis of Compound (IA-5)

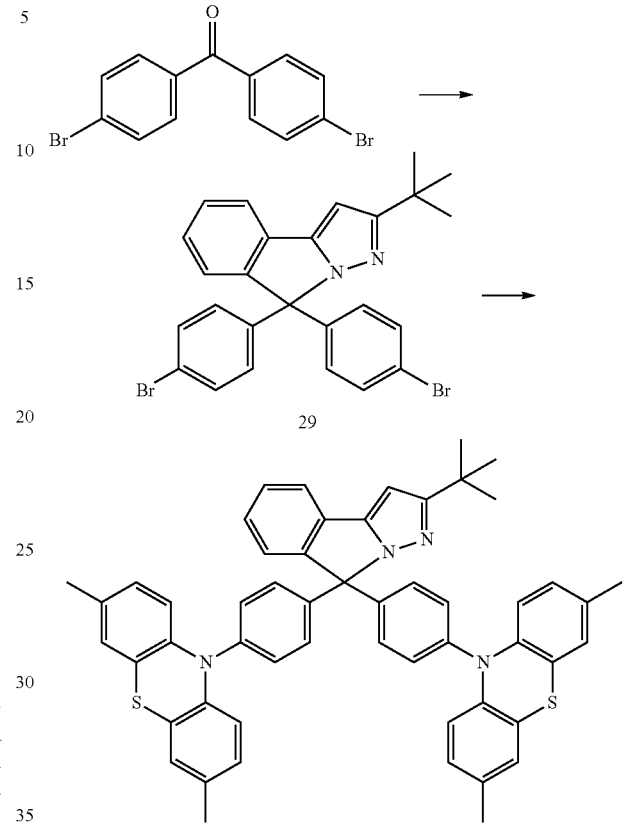

Synthesis of Compound (IA-5):

The procedure described for compound (IA-16) was performed, except that different reactants were employed, to obtain a pure product of compound (IA-5) in a yield of 83%.

Spectral data of compound (IA-5): $^1$H NMR (400 MHz, DMSO-$d_6$): δ 7.73 (d, J=7.5 Hz, 1H), 7.66 (d, J=7.8 Hz, 1H), 7.47-7.43 (m, 1H), 7.40-7.36 (m, 1H), 7.26 (d, J=8.5 Hz, 4H), 7.17 (d, J=8.5 Hz, 4H), 6.97-6.94 (m, 4H), 6.79 (d, J=9.2 Hz, 4H), 6.49 (s, 1H), 6.37 (d, J=8.1 Hz, 4H), 2.13 (s, 12H), 1.27 (s, 9H). MS [FAB], m/z 814.3 M$^+$. Anal. Calcd. for $C_{54}H_{46}N_4S_2$: C, 79.57; H, 5.69; N, 6.87. Found: C, 79.65; H, 5.70; N, 6.80.

Embodiment 20: Synthesis of Compound (IA-6)

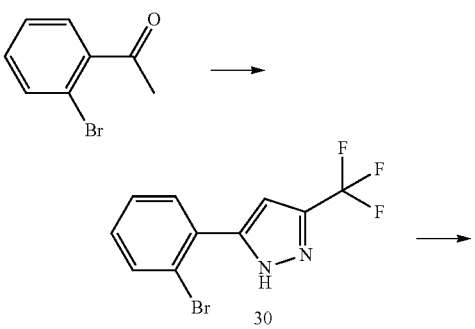

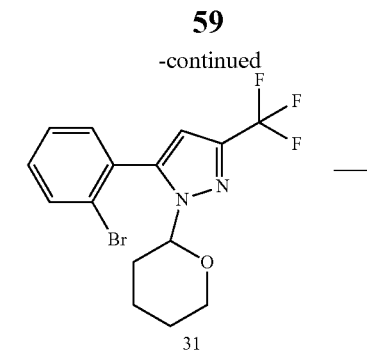

31

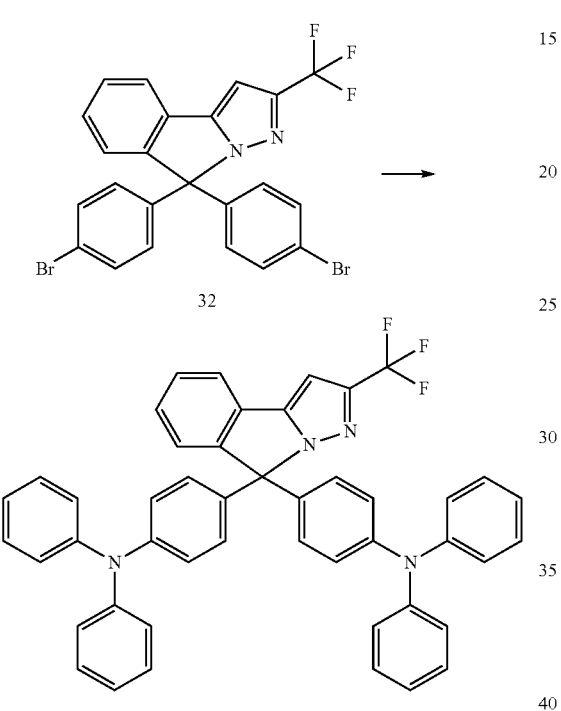

32

Synthesis of Compound (30):

The procedure described for compound (2) was performed, except that different reactants were employed, to obtain a pure product of compound (30) in a yield of 80%.

Spectral data of compound (30): $^1$H NMR (400 MHz, CDCl$_3$): δ 7.70 (d, J=8.0 Hz, 1H), 7.49 (d, J=7.7 Hz, 1H), 7.42-7.38 (m, 1H), 7.31-7.26 (m, 1H), 6.82 (s, 1H). $^{19}$F NMR (376 MHz, CDCl$_3$): δ −62.11 (s, 3F).

Synthesis of Compound (31):

The procedure described for compound (3) was performed, except that different reactants were employed, to obtain a pure product of compound (31) in a yield of 70%.

Spectral data of compound (31): $^1$H NMR (400 MHz, CDCl$_3$): δ 7.70 (d, J=7.9 Hz, 1H), 7.41-7.40 (m, 2H), 7.36-7.32 (m, 1H), 6.56 (s, 1H), 5.00 (dd, J=9.8, 2.4 Hz, 1H), 3.99-3.94 (m, 1H), 3.37 (td, J=11.4, 2.5 Hz, 1H), 2.48-2.39 (m, 1H), 2.07-2.02 (m, 1H), 1.94-1.89 (m, 1H), 1.71-1.62 (m, 1H), 1.51-1.45 (m, 2H). $^{19}$F NMR (376 MHz, CDCl$_3$): δ −62.05 (s, 3F).

Synthesis of Compound (32):

The procedure described for compound (29) was performed, except that different reactants were employed, to obtain a pure product of compound (32) in a yield of 55%.

Spectral data of compound (32): $^1$H NMR (400 MHz, CDCl$_3$): δ 7.66 (d, J=6.9 Hz, 1H), 7.47-7.34 (m, 7H), 7.04-7.01 (m, 4H), 6.68 (s, 1H). $^{19}$F NMR (376 MHz, CDCl$_3$): δ −62.11 (s, 3F). MS [EI], m/z 533.2 M$^+$.

Synthesis of Compound (IA-6):

The procedure described for compound (IA-16) was performed, except that different reactants were employed, to obtain a pure product of compound (IA-6) in a yield of 70%.

Spectral data of compound (IA-6): $^1$H NMR (400 MHz, DMSO-d$_6$): δ 7.84 (d, J=6.9 Hz, 1H), 7.57 (d, J=6.8 Hz, 1H), 7.52-7.44 (m, 2H), 7.27-7.23 (m, 8H), 7.10 (s, 1H), 7.04-7.00 (m, 4H), 6.98-6.95 (m, 12H), 6.85 (d, J=8.8 Hz, 4H). $^{19}$F NMR (376 MHz, CDCl$_3$): δ −60.35 (s, 3F). MS [FAB], m/z 710.3 M$^+$.

Embodiment 21: Synthesis of Compound (IA-7)

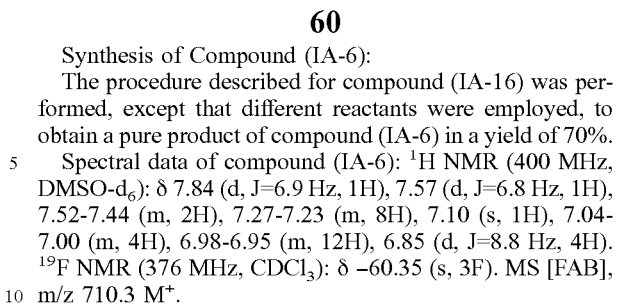

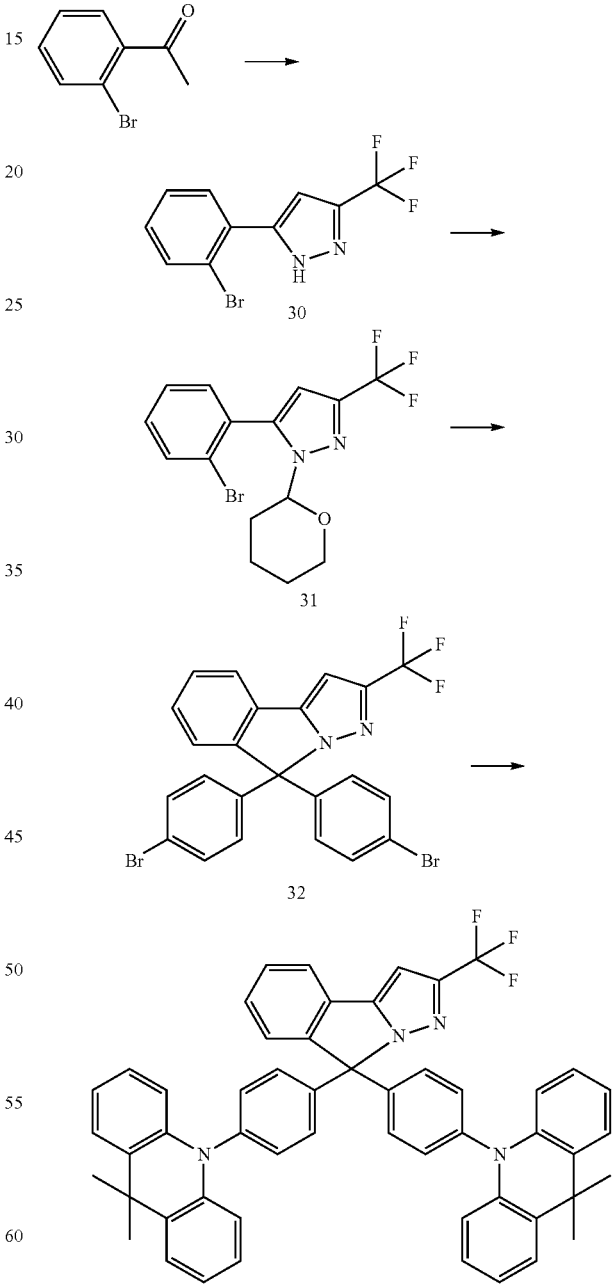

Synthesis of Compound (IA-7):

The procedure described for compound (IA-16) was performed, except that different reactants were employed, to obtain a pure product of compound (IA-7) in a yield of 60%.

Spectral data of compound (IA-7): $^1$H NMR (400 MHz, CDCl$_3$): δ 7.79-7.75 (m, 1H), 7.65 (m, J=4.8, 3.1 Hz, 1H), 7.57-7.49 (m, 6H), 7.43 (dd, J=7.6, 1.6 Hz, 4H), 7.36-7.32 (dd 4H), 6.98-6.88 (m, 8H), 6.81 (s, 1H), 6.24 (dd, J=8.1, 1.3 Hz, 4H), 1.65 (s, 12H). $^{19}$F NMR (376 MHz, CDCl$_3$): δ −61.80 (s, 3F).

Embodiment 22: Synthesis of Compound (IA-8)

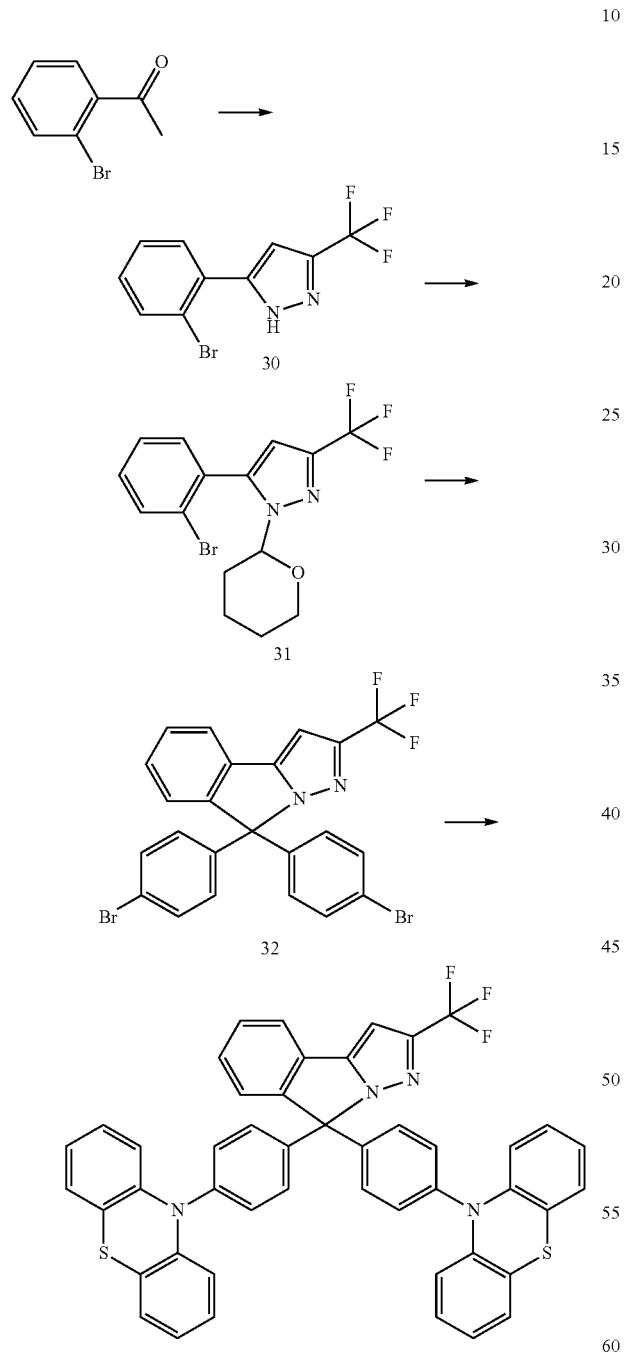

Synthesis of Compound (IA-8):

The procedure described for compound (IA-16) was performed, except that different reactants were employed, to obtain a pure product of compound (IA-8) in a yield of 50%.

Spectral data of compound (IA-8): $^1$H NMR (400 MHz, CD$_2$Cl$_2$): δ 7.78 (d, J=6.2 Hz, 1H), 7.58 (d, 1H), 7.55-7.47 (m, 2H), 7.40 (d, J=8.8 Hz, 4H), 7.31 (d, J=8.7 Hz, 4H), 7.08 (dd, J=1.8 Hz, 4H), 6.90 (m, J=12.2, 6.2 Hz, 8H), 6.81 (s, 1H), 6.45 (dd, J=1.3 Hz, 4H). $^{19}$F NMR (376 MHz, CD$_2$Cl$_2$): 6-62.17 (s, 3F).

Embodiment 23: Synthesis of Compound (IA-9)

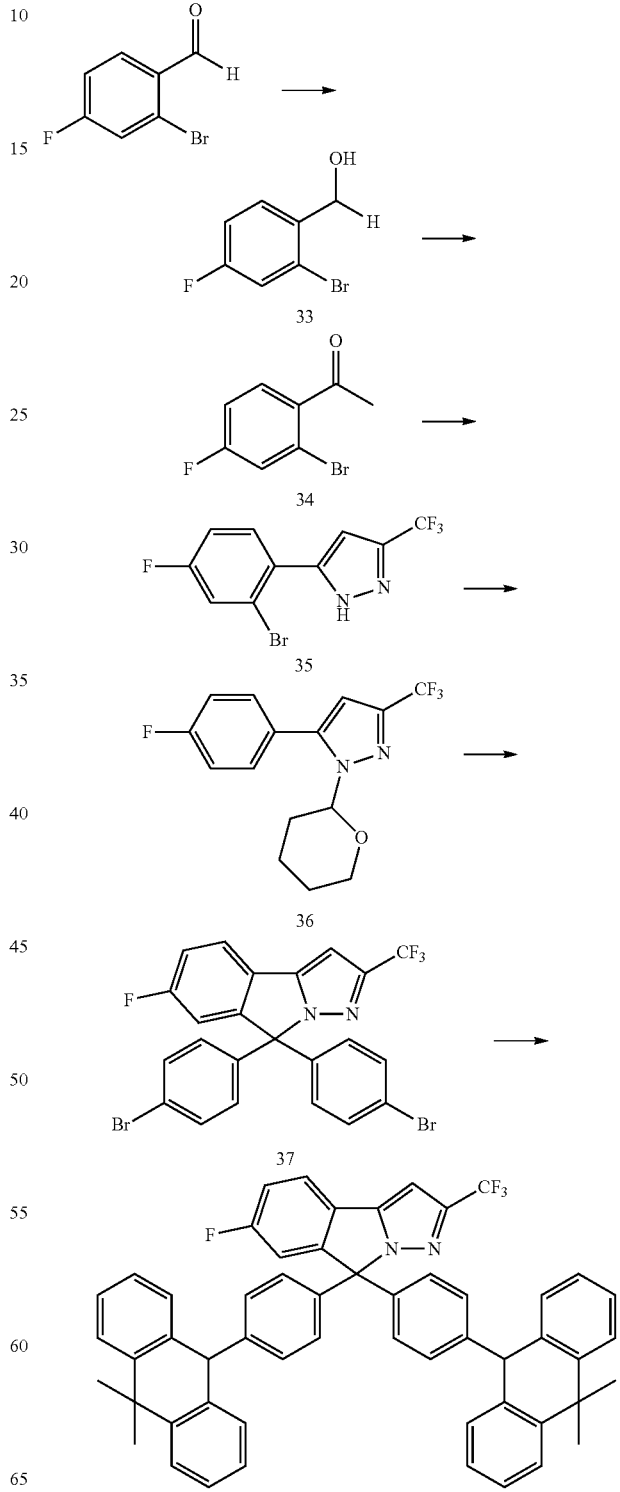

Synthesis of Compound (33):

To a solution of 2-bromo-4-fluorobenzaldehyde (2 g, 9.9 mmol) in dry ether (19.8 mL) at 0° C. was added slowly dropwise a solution of methylmagnesium bromide (6.6 mL, 19.8 mmol) under $N_2$ atmosphere. The resulting mixture was stirred at 0° C. for 3 hours, then quenched with saturated aqueous $NH_4Cl$ solution and extracted with ethyl acetate. The organic layers were washed with brine, dried over $Na_2SO_4$, filtered and concentrated in vacuo. The crude product was purified by column chromatography to afford the compound (33) in a yield of 92%.

Spectral data of compound (33): $^1H$ NMR (400 MHz, $CDCl_3$): δ 7.56 (dd, J=8.7, 6.1 Hz, 1H), 7.28-7.22 (m, 1H), 7.06 (td, J=8.3, 2.6 Hz, 1H), 5.20 (q, J=6.4 Hz, 1H), 1.97 (s, 1H), 1.45 (d, J=6.4 Hz, 3H). $^{19}F$ NMR (376 MHz, $CDCl_3$): δ −113.55 (s, 1F).

Synthesis of Compound (34):

To a solution of compound (33) (1.83 g, 8.35 mmol) in dry $CH_2Cl_2$ (41.75 mL) was added a mixture of pyridinium chlorochromate (PCC) (5.4 g, 25.1 mmol). The resulting suspension was stirred at room temperature for 2 hours, filtered through a pad of silica gel, washed with $CH_2Cl_2$ and concentrated in vacuo. The crude product was purified by flash column chromatography to afford the compound (34) in a yield of 92%.

Spectral data of compound (34): $^1H$ NMR (400 MHz, $CDCl_3$): δ 7.54 (dd, J=8.6, 5.9 Hz, 1H), 7.35 (dd, J=8.3, 2.5 Hz, 1H), 7.08 (ddd, J=8.6, 7.7, 2.5 Hz, 1H), 2.62 (s, 3H). $^{19}F$ NMR (376 MHz, $CDCl_3$): δ −107.01 (s, 1F).

Synthesis of Compound (35):

The procedure described for compound (2) was performed, except that different reactants were employed, to obtain a product of compound (35) in a crude yield of 38% and used in the next step without further purification.

Synthesis of Compound (36):

The procedure described for compound (3) was performed, except that different reactants were employed, to obtain a pure product of compound (36) in a yield of 71%.

Spectral data of compound (36): $^1H$ NMR (400 MHz, $CDCl_3$): δ 7.47-7.38 (m, 2H), 7.13 (td, J=8.0, 2.2 Hz, 1H), 6.55 (s, 1H), 5.01-4.92 (dd, 1H), 3.96 (d, J=11.5 Hz, 1H), 3.38 (td, J=11.2, 2.4 Hz, 1H), 2.44 (d, J=12.1 Hz, 1H), 2.05 (d, J=13.2 Hz, 1H), 1.91 (dd, J=13.3, 3.1 Hz, 1H), 1.72-1.61 (m, 1H), 1.53-1.45 (m, 2H). $^{19}F$ NMR (376 MHz, $CDCl_3$): δ −62.12 (s, 3F), −108.60 (s, 1F).

Synthesis of Compound (37):

The procedure described for compound (29) was performed, except that different reactants were employed, to obtain a pure product of compound (37) in a yield of 23%.

Spectral data of compound (37): $^1H$ NMR (400 MHz, $CDCl_3$): δ 7.63 (dd, J=8.4, 4.9 Hz, 1H), 7.48-7.42 (d, 4H), 7.17 (t, J=8.6 Hz, 1H), 7.07 (d, J=8.1 Hz, 1H), 7.03-6.98 (d, 4H), 6.64 (s, 1H). $^{19}F$ NMR (376 MHz, $CDCl_3$): δ −62.04 (s, 3F), −109.77 (s, 1F).

Synthesis of Compound (IA-9):

The procedure described for compound (IA-16) was performed, except that different reactants were employed, to obtain a pure product of compound (IA-9) in a yield of 66%.

Spectral data of compound (IA-9): $^1H$ NMR (400 MHz, $CD_2Cl_2$): δ 7.55 (d, J=8.7 Hz, 4H), 7.45 (dd, J=7.6, 1.6 Hz, 5H), 7.39 (d, J=8.7 Hz, 6H), 6.98-6.88 (m, 8H), 6.82 (s, 1H), 6.26 (dd, J=8.0, 1.2 Hz, 4H), 1.66 (s, 12H). $^{19}F$ NMR (376 MHz, $CD_2Cl_2$): δ −62.21 (s, 3F), −110.71 (s, 1F).

Embodiment 24: Synthesis of Compound (IA-33)

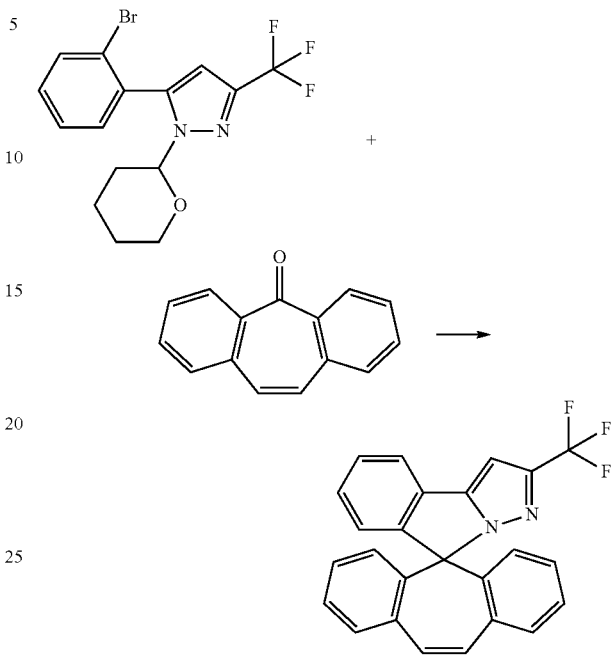

A solution of compound (31) (220 mg, 0.59 mmol) in dry THF (3 mL) was treated with n-BuLi (300 μL, 2.5 M in n-hexane) under nitrogen at −78° C. After 30 minutes, a solution of 5-dibenzosuberenone (91 mg, 0.45 mmol) in THF (4 mL) was added dropwise. The mixture was stirred for 30 minutes at −78° C., and gradually allowed to warm up to room temperature. After stirring for 12 hours, the solution was concentrated and the residue was extracted with $CH_2Cl_2$ and washed with brine and water in sequence and finally dried over $Na_2SO_4$. Then, the intermediate was added to a mixture of concentrated aqueous HCl (0.3 mL) and acetic acid (9 mL). After stirring at room temperature for 1 hour, the solvent was removed. The crude product was extracted with $CH_2Cl_2$ and washed with water. The organic layer was dried over anhydrous $Na_2SO_4$ and purified by silica gel column chromatography eluting with hexane:EA=20:1 as the eluent; yield: 83%.

Spectral data of compound (IA-33): $^1H$ NMR (400 MHz, $CDCl_3$): δ 8.34-8.31 (d, J=8 Hz, 1H), 7.56 (d, J=7.6 Hz, 1H), 7.41 (dd, J=7.6, 1.4 Hz, 2H), 7.29 (m, 3H), 7.19 (t, J=6.6 Hz, 2H), 7.13 (t, J=6.8 Hz, 1H), 7.02 (s, 2H), 6.90 (s, 1H), 6.33 (dd, J=8.2, 1.1 Hz, 2H). $^{19}F$ NMR (376 MHz, $CDCl_3$): δ −61.81 (s, 1F).

Embodiment 25: Synthesis of Compound (IA-34)

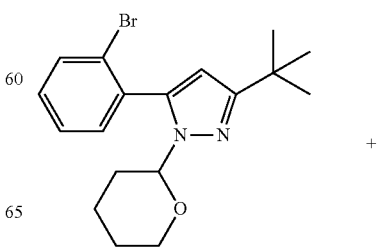

-continued

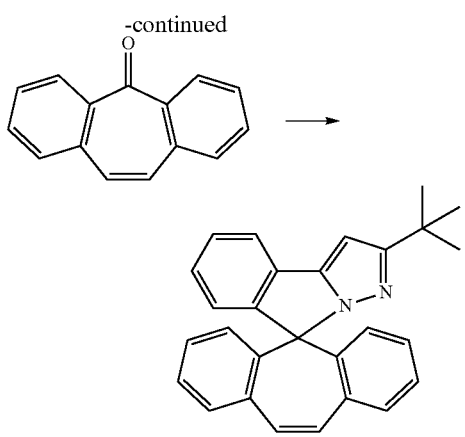

A solution of compound (3) (264 mg, 0.73 mmol) in dry THF (3 mL) was treated with n-BuLi (330 μL, 2.5 M in n-hexane) under nitrogen at −78° C. After 30 minutes, a solution of 5-dibenzosuberenone (100 mg, 0.49 mmol) in THF (4 mL) was added dropwise. The mixture was stirred for 30 minutes at −78° C., and gradually allowed to warm up to room temperature. After stirring for 12 hours, the solution was concentrated and the residue was extracted with $CH_2Cl_2$ and washed with brine and water in sequence and finally dried over $Na_2SO_4$. Then, the intermediate was added to a mixture of concentrated aqueous HCl (0.33 mL) and acetic acid (10 mL). After stirring at room temperature for 1 hour, the solvent was removed. The crude product was extracted with $CH_2Cl_2$ and washed with water. The organic layer was dried over anhydrous $Na_2SO_4$ and purified by silica gel column chromatography eluting with hexane:EA=20:1 as the eluent; yield: 51%.

Spectral data of compound (IA-34): $^1$H NMR (400 MHz, $CDCl_3$): δ 8.29 (d, J=8.0 Hz, 1H), 7.47 (d, J=7.6 Hz, 1H), 7.36 (dd, J=7.5, 1.5 Hz, 2H), 7.23 (m, 3H), 7.17-7.12 (t, J=6.8 Hz, 2H), 7.04-6.99 (t, J=6.4 Hz, 1H), 6.98 (s, 2H), 6.48 (s, 1H), 6.44 (dd, J=8.2, 1.1 Hz, 2H), 1.52 (s, 9H).

Embodiment 26: Synthesis of Compound (IA-35)

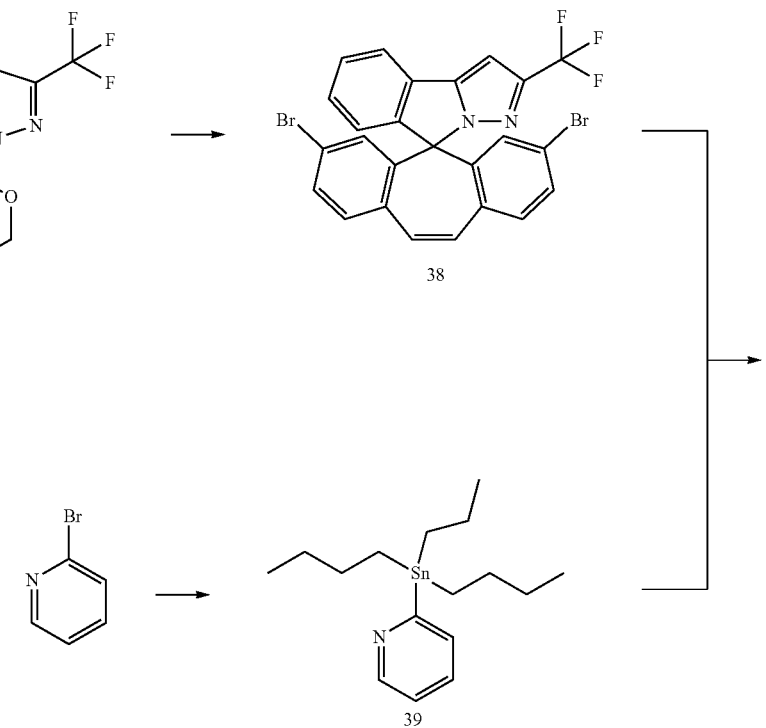

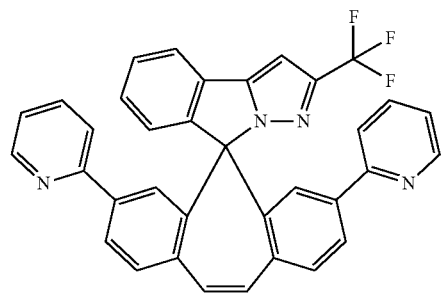

Synthesis of Compound (38):

The procedure described for compound (29) was performed, except that different reactants were employed, to obtain a pure product of compound (38) in a yield of 23%.

Spectral data of compound (38): $^1$H NMR (400 MHz, CDCl$_3$): δ 8.23 (dd, J=8.1, 0.4 Hz, 1H), 7.60-7.57 (d 1H), 7.40 (dd, J=8.2, 1.9 Hz, 2H), 7.36-7.30 (t, 1H), 7.25-7.24 (m, 1H), 7.23 (s, 1H), 7.17-7.11 (m, 1H), 6.95 (s, 2H), 6.92 (s, 1H), 6.42 (d, J=1.9 Hz, 2H). $^{19}$F NMR (376 MHz, CDCl$_3$): δ −62.21 (s, 3F).

Synthesis of Compound (39):

n-BuLi (1.4 mL, 3.5 mmol) was added dropwise to a solution of 2-bromopyridine (0.5 g, 3.19 mmol) in dry THF (7 mL) at −78° C. and stirred for 1 hour. Tributyltin chloride (0.87 mL, 3.19 mmol) was added to the solution at −78° C. and continuously stirred for 3 hours at −78° C., followed by another 30 minutes at room temperature. The reaction was quenched with saturated aqueous NH$_4$Cl solution and extracted with ethylacetate (3×25 mL). The combined organic layers were washed with brine, and dried over anhydrous Na$_2$SO$_4$. The solvent was evaporated under reduced pressure and used in the next step without further purification.

Spectral data of compound (39): $^1$H NMR (400 MHz, CDCl$_3$): δ 8.75-8.68 (m, 1H), 7.46 (td, J=7.5, 1.8 Hz, 1H), 7.38 (d, J=7.4 Hz, 1H), 7.09 (m, J=4.9, 4.1, 1.7 Hz, 1H), 1.56 (m, J=17.2, 15.9, 7.1 Hz, 6H), 1.31 (dd, J=14.6, 7.3 Hz, 6H), 1.19-1.01 (m, 6H), 0.91-0.81 (m, 9H).

Synthesis of Compound (IA-35):

A solution of compound (38) (0.1 g, 0.18 mmol), compound (39) (0.16 g, 0.43 mmol), PdCl$_2$(dppf) (0.013 g, 0.018 mmol) in degassed toluene (4 mL) was heated to reflux for 12 hours under nitrogen. After cooling, the reaction mixture was filtered, followed by removal of all volatile components. Then, EA and water were added, the organic layer was washed with brine and water, and dried over Na$_2$SO$_4$. The pure product can be obtained by column chromatography using hexane:EA=3:1 as the eluent in a yield of 80%.

Spectral data of compound (IA-35): $^1$H NMR (400 MHz, CD$_2$Cl$_2$): δ 8.58 (ddd, J=4.8, 1.8, 0.9 Hz, 2H), 8.38 (d, J=8.1 Hz, 2H), 8.03 (dd, J=8.0, 1.7 Hz, 2H), 7.69-7.62 (m, 3H), 7.54 (d, J=8.0 Hz, 4H), 7.48 (d, J=8.1 Hz, 3H), 7.12 (s, 2H), 6.98 (d, J=1.7 Hz, 2H), 6.95 (s, 1H). $^{19}$F NMR (376 MHz, CDCl$_3$): δ −62.06 (s, 3F).

Figure 2:
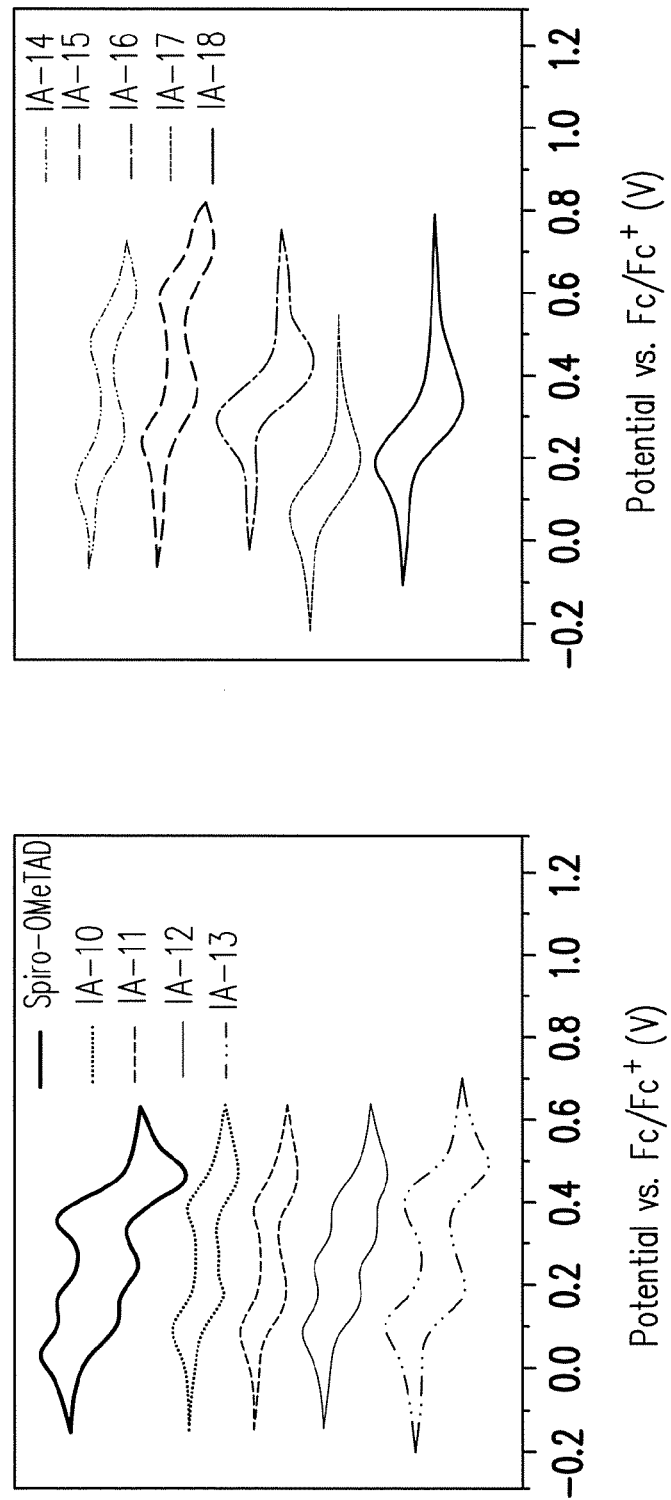
FIG. 2 is the cyclic voltammogram of each of compounds (IA-10) to (IA-18) of some embodiments of the invention.

FIG. 1 is the absorption spectrum of each of compounds (IA-10) to (IA-18) of some embodiments of the invention. The absorption spectrum is measured by using THF as a solvent and the compound Spiro-OMeTAD (2,2',7,7'-tetrakis[N,N-di(4-methoxyphenyl)amino]-9,9'-spirobifluorene) as a comparative example. FIG. 2 is the cyclic voltammogram of each of compounds (IA-10) to (IA-18) of some embodiments of the invention. The cyclic voltammogram is measured by using DCM as a solvent and the compound Spiro-OMeTAD as a comparative example. The absorption wavelength ($\lambda_{abs}$), energy difference ($E_{g,opt}$), oxidation potential ($E_{ox}$), highest occupied molecular orbital (HOMO), lowest unoccupied molecular orbital (LUMO) of each of compounds (IA-10) to (IA-18) of some embodiments of the invention are listed in Table 1.

As shown in FIG. 1 and Table 1, the compounds of the invention have excellent absorption within the range of short wavelength, so the application thereof in the field of photoelectric materials is excellent. As shown in FIG. 2 and Table 1, the compounds of the invention have excellent reversible oxidation-reduction property and appropriate orbital energy difference, so the application thereof in the field of photoelectric materials is excellent.

TABLE 1

|  | $\lambda_{abs}$ (nm) | $E_{g,opt}^{[a]}$ (eV) | $E_{ox}$ (V) | HOMO[b] (eV) | LUMO[c] (eV) |
|---|---|---|---|---|---|
| Spiro-OMeTAD | 303, 365, 386 | 3.00 | 0.002 | −5.10 | −2.10 |
| compound (IA-10) | 290, 386 | 2.98 | 0.065 | −5.16 | −2.18 |
| compound (IA-11) | 269, 386 | 2.98 | 0.065 | −5.16 | −2.18 |
| compound (IA-12) | 306, 346, 386 | 2.98 | 0.057 | −5.15 | −2.17 |
| compound (IA-14) | 269, 354, 386 | 2.93 | 0.132 | −5.23 | −2.30 |
| compound (IA-15) | 268, 354, 382 | 3.03 | 0.232 | −5.33 | −2.30 |
| compound (IA-16) | 258,285 | 3.13 | 0.277 | −5.38 | −2.25 |
| compound (IA-17) | 258, 285, 331 | 2.93 | 0.023 | −5.12 | −2.19 |
| compound (IA-18) | 260, 286, 336 | 3.21 | 0.171 | −5.27 | −2.06 |
| compound (IA-13) | 290, 386 | 2.98 | 0.074 | −5.17 | −2.19 |

Figure 3:
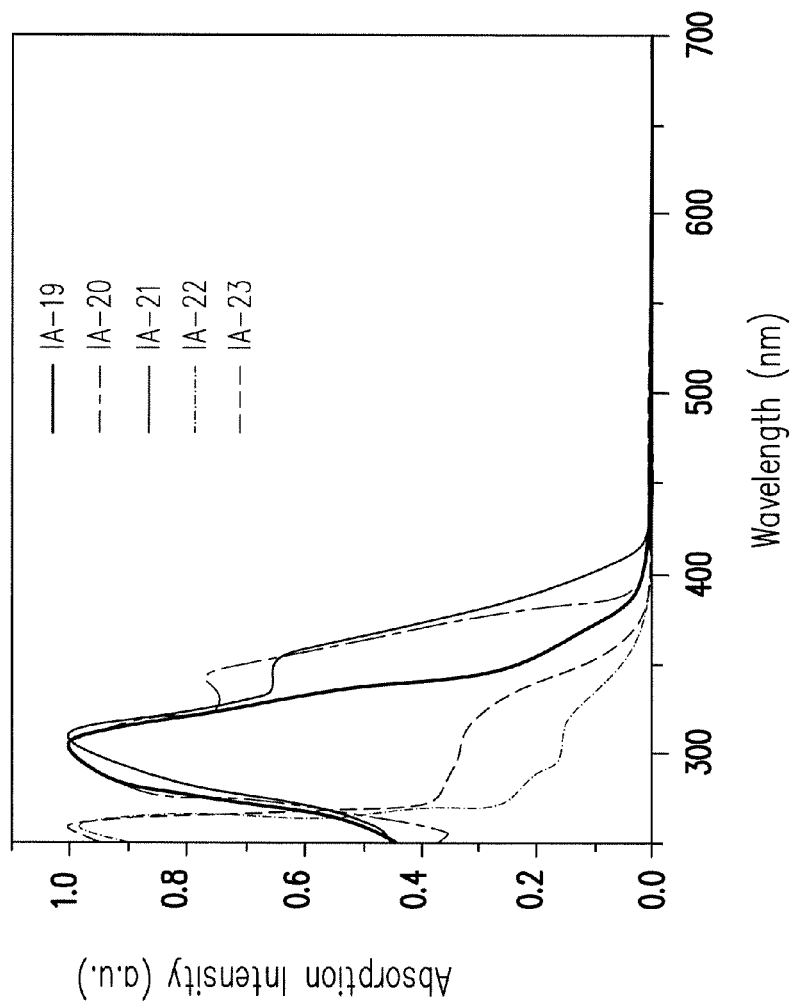
FIG. 3 is the absorption spectrum of each of compounds (IA-19) to (IA-23) of some embodiments of the invention.
Figure 4:
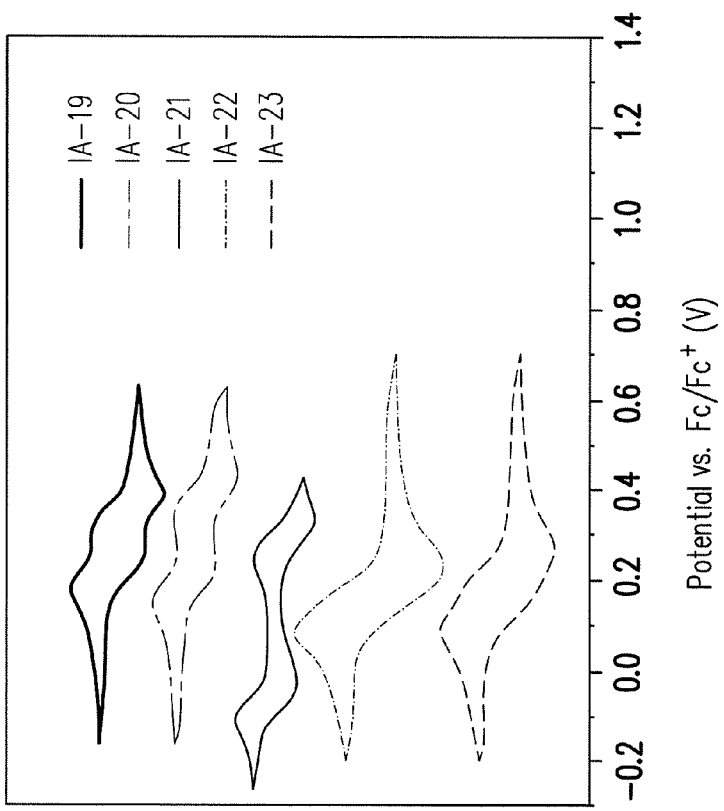
FIG. 4 is the cyclic voltammogram of each of compounds (IA-19) to (IA-23) of some embodiments of the invention.

[a]From the absorption onset
[b]HOMO = −(E$_{ox}$ + 5.1) eV
[c]LUMO = HOMO + E$_{g,opt}$ FIG. 3 is the absorption spectrum of each of compounds (IA-19) to (IA-23) of some embodiments of the invention. The absorption spectrum is measured by using THF as a solvent. FIG. 4 is the cyclic voltammogram of each of compounds (IA-19) to (IA-23) of some embodiments of the invention. The cyclic voltammogram is measured by using DCM as a solvent. The absorption wavelength ($\lambda_{abs}$), energy difference ($E_{g,opt}$), oxidation potential ($E_{ox}$), highest occupied molecular orbital (HOMO), lowest unoccupied molecular orbital (LUMO) of each of compounds (IA-10) to (IA-18) of some embodiments of the invention are listed in Table 2.

As show in FIG. 3 and Table 2, the compounds of the invention have excellent absorption within the range of short wavelength, so the application thereof in the field of photoelectric materials is excellent. As shown in FIG. 4 and Table 2, the compounds of the invention have excellent reversible oxidation-reduction property and appropriate orbital energy difference, so the application thereof in the field of photoelectric materials is excellent.

TABLE 2

|  | $\lambda_{abs}$ (nm) | $E_{g,opt}^{[a]}$ (eV) | $E_{ox}$ (V) | HOMO[b] (eV) | LUMO[c] (eV) |
|---|---|---|---|---|---|
| compound (IA-19) | 303 | 3.17 | 0.146 | −5.24 | −2.07 |
| compound (IA-20) | 303, 340 | 3.19 | 0.129 | −5.23 | −2.04 |
| compound (IA-21) | 307, 350 | 3.01 | −0.136 | −4.96 | −1.95 |
| compound (IA-22) | 258, 315 | 3.30 | 0.060 | −5.16 | −1.86 |
| compound (IA-23) | 258, 318 | 3.40 | 0.058 | −5.16 | −1.76 |

Figure 5:
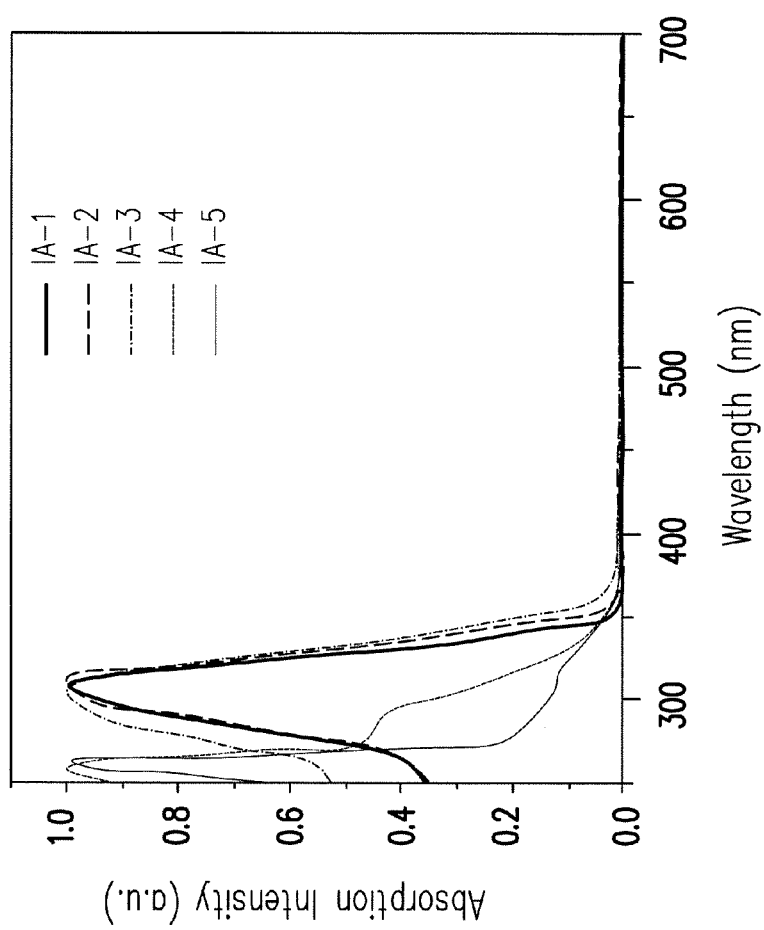
FIG. 5 is the absorption spectrum of each of compounds (IA-1) to (IA-5) of some embodiments of the invention.
Figure 6:
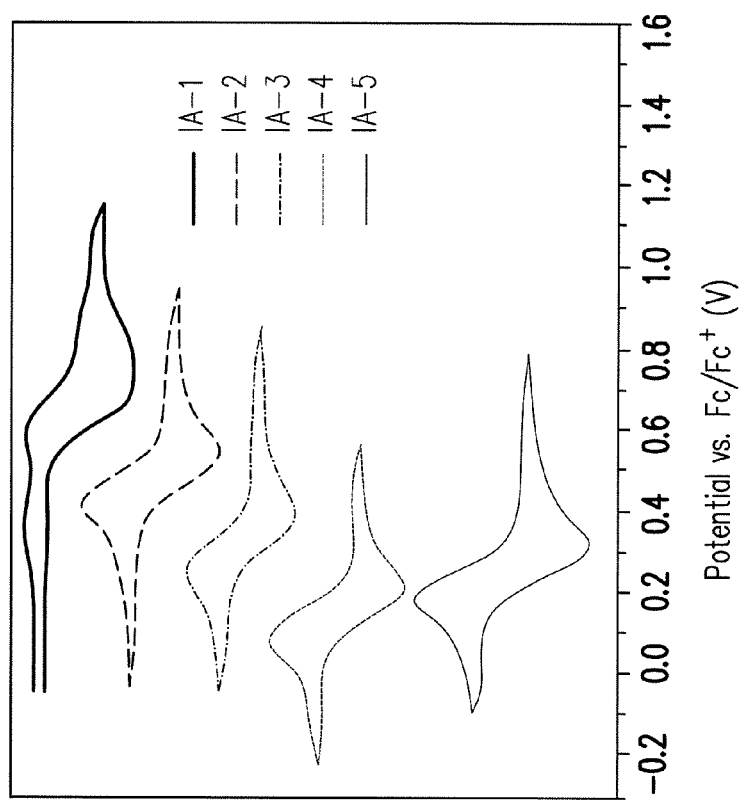
FIG. 6 is the cyclic voltammogram of each of compounds (IA-1) to (IA-5) of some embodiments of the invention.

[a]From the absorption onset
[b]HOMO = −(E$_{ox}$ + 5.1) eV
[c]LUMO = HOMO + E$_{g,opt}$ FIG. 5 is the absorption spectrum of each of compounds (IA-1) to (IA-5) of some embodiments of the invention. The absorption spectrum is measured by using THF as a solvent. FIG. 6 is the cyclic voltammogram of each of compounds (IA-1) to (IA-5) of some embodiments of the invention. The cyclic voltammogram is measured by using DCM as a solvent. The absorption wavelength ($\lambda_{abs}$), energy difference ($E_{g,opt}$), oxidation potential ($E_{ox}$), highest occupied molecular orbital (HOMO), lowest unoccupied molecular orbital (LUMO) of each of compounds (IA-1) to (IA-5) of some embodiments of the invention are listed in Table 3.

As shown in FIG. 5 and Table 3, the compounds of the invention have excellent absorption within the range of short wavelength, so the application thereof in the field of photoelectric materials is excellent. As shown in FIG. 6 and Table 3, the compounds of the invention have excellent reversible oxidation-reduction property and appropriate orbital energy difference, so the application thereof in the field of photoelectric materials is excellent.

TABLE 3

| | $\lambda_{abs}$ (nm) | $E_{g,opt}$[a] (eV) | $E_{ox}$ (V) | HOMO[b] (eV) | LUMO[c] (eV) |
|---|---|---|---|---|---|
| compound (IA-1) | 305 | 3.57 | 0.530 | −5.63 | −2.06 |
| compound (IA-2) | 305 | 3.50 | 0.381 | −5.48 | −1.98 |
| compound (IA-3) | 304 | 3.44 | 0.234 | −5.33 | −1.89 |
| compound (IA-4) | 256, 285 | 3.33 | 0.065 | −5.16 | −1.83 |
| compound (IA-5) | 259, 319 | 3.40 | 0.168 | −5.27 | −1.87 |

[a]From the absorption onset
[b]HOMO = −($E_{ox}$ + 5.1) eV
[c]LUMO = HOMO + $E_{g,opt}$ The device performance data of the solar cell devices produced by using the compounds (IA-10) to (IA-12), (IA-19) to (IA-20) of some embodiments of the invention are listed in Table 4. JSC is short-circuit current density, VOC is open-circuit voltage, FF is fill-factor, PCE is power conversion efficiency.

As shown in Table 4, as compared to the conventional technology, the solar cell produced by using the compound of the invention has comparable (or even better) energy conversion efficiency, so the application thereof in the field of photoelectric materials is excellent.

TABLE 4

| | $J_{SC}$ (mA/cm$^2$) | $V_{OC}$ (V) | Fill Factor (FF) | PCE (%) |
|---|---|---|---|---|
| Spiro-OMeTAD | 19.20 | 1.041 | 0.742 | 14.84 |
| compound (IA-10) | 19.48 | 1.053 | 0.691 | 14.19 |
| compound (IA-11) | 18.50 | 1.057 | 0.696 | 13.60 |
| compound (IA-12) | 18.27 | 1.047 | 0.674 | 12.89 |
| compound (IA-19) | 19.10 | 1.07 | 0.787 | 16.08 |
| compound (IA-20) | 20.60 | 1.10 | 0.797 | 18.06 |

Based on the above, in the organic compound of the invention, at least one C—N bond replaces the conventional C—C bond, so that the organic compound of the invention has an asymmetry tetrahedral-like geometry. The organic compounds of the invention have excellent absorption within the range of short wavelength, and have excellent reversible oxidation-reduction property and appropriate orbital energy difference, so the application thereof in the field of photoelectric materials is excellent. In addition, as compared to the conventional technology, the solar cell containing the organic compound of the invention has comparable (or even better) energy conversion efficiency. Therefore, the organic compound of the invention has a considerably high application value.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. An organic compound having a structure represented by formula (IA):

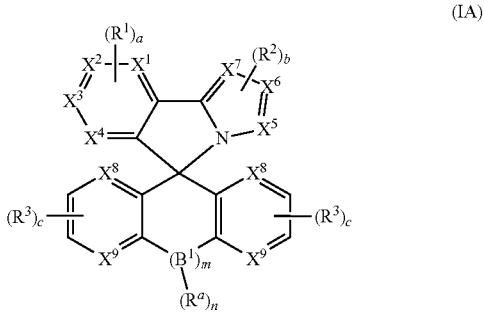

wherein
$X^1$ to $X^9$ are each independently carbon or nitrogen;
each of $R^1$'s and $R^2$'s is independently hydrogen, $C_1$-$C_6$ alkoxy, $C_6$-$C_{12}$ aryl or —$C_yF_{2y+1}$, y is an integer of 0 to 3;
a is an integer of 0 to 4;
b is an integer of 0 to 3;
each of $R^3$'s is independently hydrogen, halogen, cyano, $C_1$-$C_{12}$ alkyl, $C_1$-$C_6$ alkoxy, $C_6$-$C_{12}$ aryl, amino or phosphinyl;
c is an integer of 0 to 4;
when c is equal to or greater than 1, each of $R^3$'s can be the same or different;
$B^1$ represents direct bonding, —C—, —O—, —N—, —S— or —C=C—;
m is 1;
each of $R^a$'s is independently hydrogen, fluorine, oxygen, $C_1$-$C_{12}$ alkyl or $C_6$-$C_{12}$ aryl; and
n is an integer of 0 to 2.

2. The organic compound of claim 1, having a structure represented by formula (IA-a):

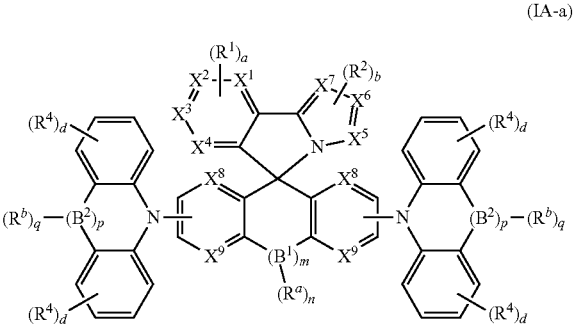

wherein
each of $R^4$'s is independently hydrogen, fluorine, $C_1$-$C_{12}$ alkyl, $C_1$-$C_6$ alkoxy or $C_6$-$C_{12}$ aryl;
d is an integer of 0 to 4;
when d is equal to or greater than 1, each of $R^4$'s can be the same or different, and two or more $R^4$'s can joint to form a $C_3$-$C_8$ aromatic ring;
$B^2$ represents —O—, —S—, —C— or —N—;
p is 0 or 1;
each of $R^b$'s is independently hydrogen, fluorine, $C_1$-$C_{12}$ alkyl; and
q is an integer of 0 to 2.

3. The organic compound of claim 2, having a structure represented by one of formula (IA-10) to formula (IA-32):

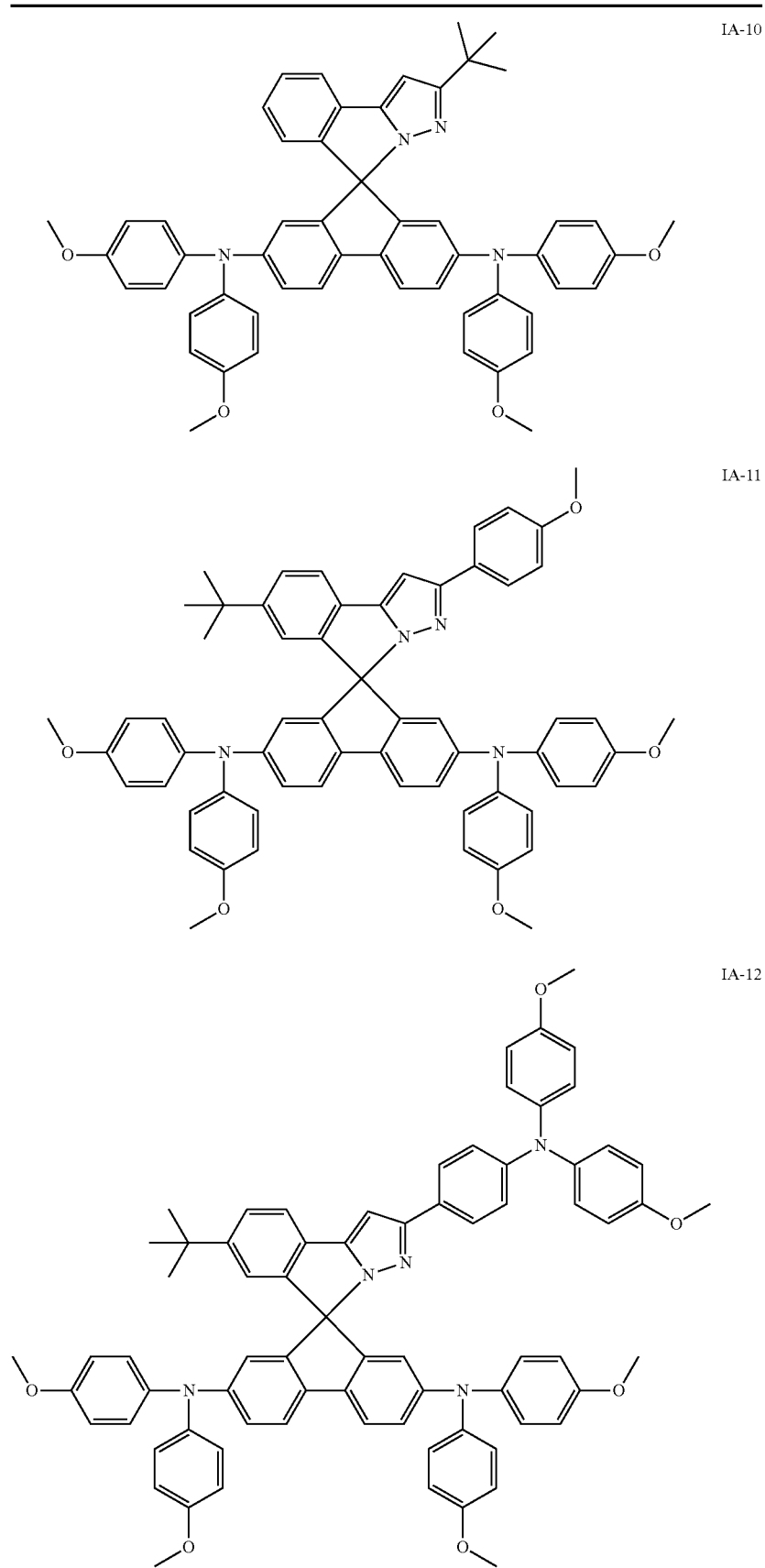

IA-13
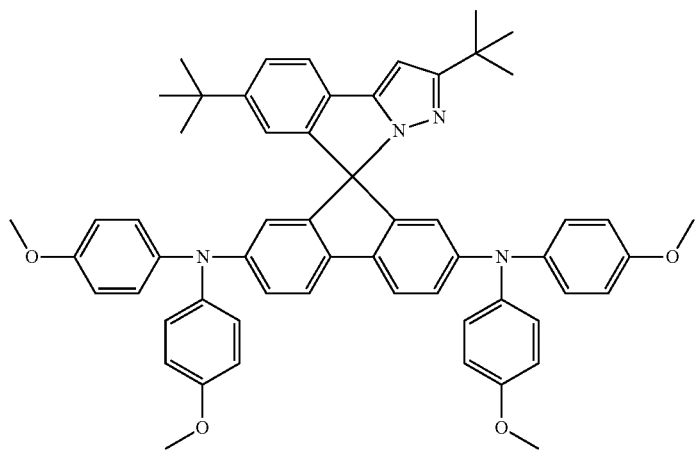
IA-14
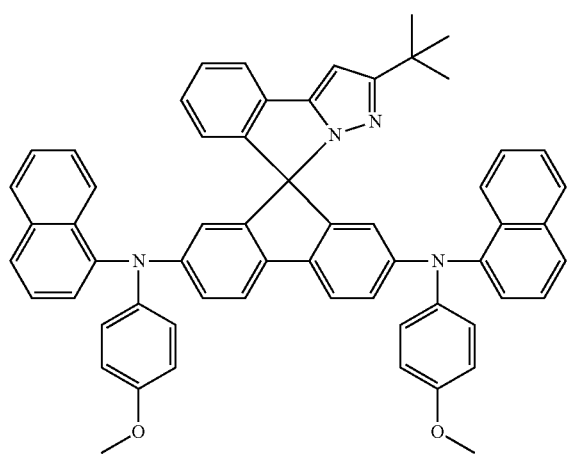 [SMILES: COc1ccc(N(c2ccc3c(c2)C2(c4cc(N(c5ccc(OC)cc5)c5cccc6ccccc56)ccc4-3)c3ccccc3-c3cc(C(C)(C)C)nn32)c2cccc3ccccc23)cc1]
IA-15
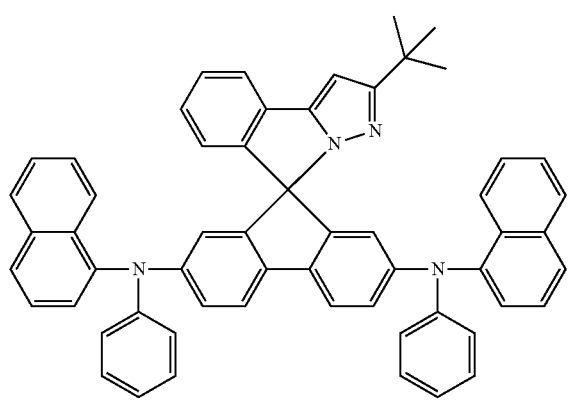 [SMILES: CC(C)(C)c1cc2n(n1)C1(c3cc(N(c4ccccc4)c4cccc5ccccc45)ccc3-c3ccc(N(c4ccccc4)c4cccc5ccccc45)cc31)c1ccccc1-2]

IA-16
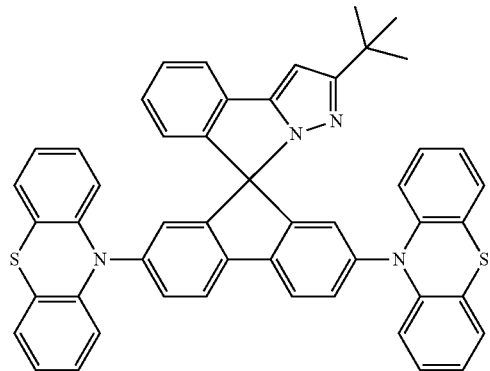 [SMILES: CC(C)(C)c1cc2n(n1)C1(c3cc(N4c5ccccc5Sc5ccccc54)ccc3-c3ccc(N4c5ccccc5Sc5ccccc54)cc31)c1ccccc1-2]
IA-17
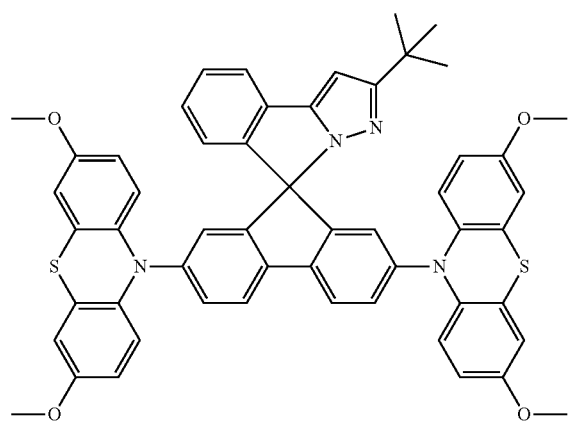
IA-18
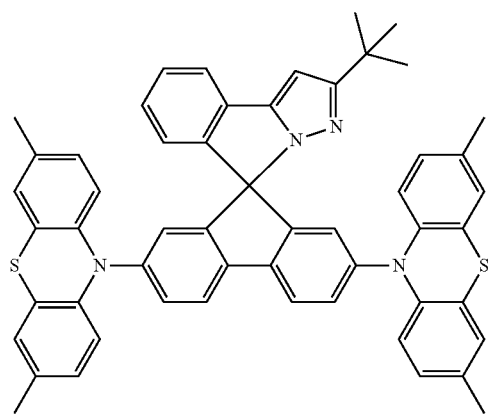 [SMILES: Cc1ccc2c(c1)Sc1cc(C)ccc1N2c1ccc2c(c1)C1(c3cc(N4c5ccc(C)cc5Sc5cc(C)ccc54)ccc3-2)c2ccccc2-c2cc(C(C)(C)C)nn21]
IA-19
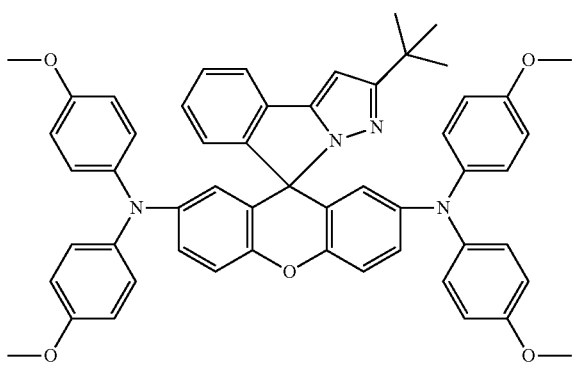

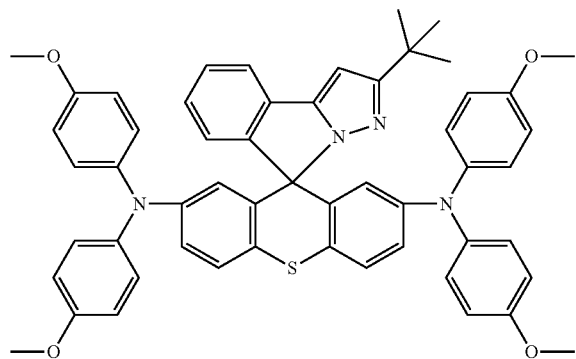
IA-20
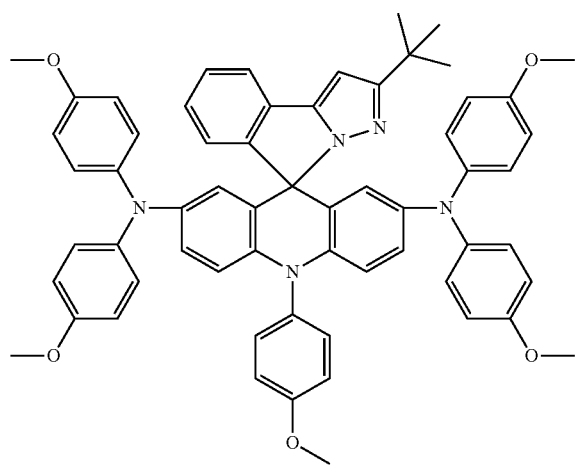
IA-21
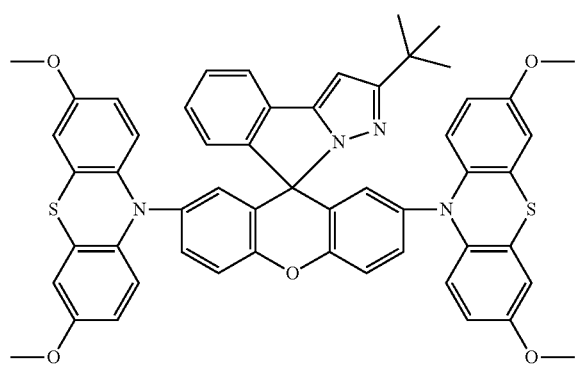
IA-22
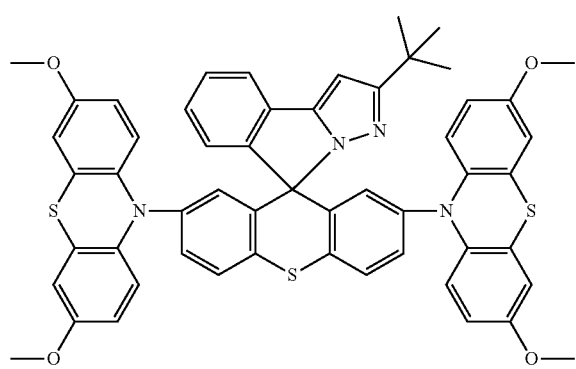
IA-23

-continued
IA-24
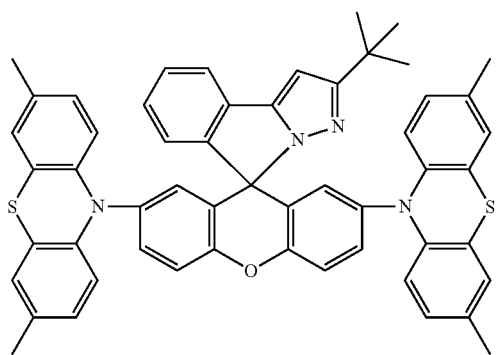
IA-25
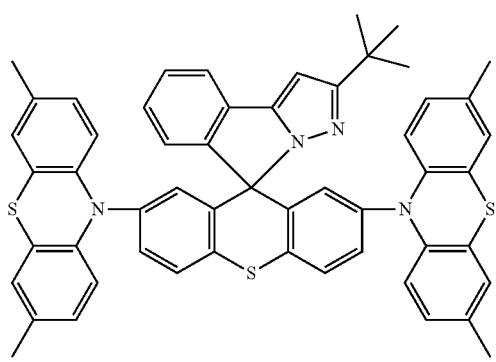 [SMILES: Cc1ccc2c(c1)Sc1cc(C)ccc1N2c1ccc2c(c1)C1(c3cc(N4c5ccc(C)cc5Sc5cc(C)ccc54)ccc3O2)c2ccccc2-c2cc(C(C)(C)C)nn21]
IA-26
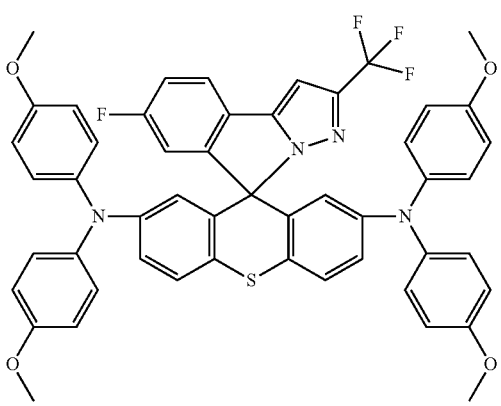 [SMILES: COc1ccc(N(c2ccc(OC)cc2)c2ccc3c(c2)C2(c4cc(N(c5ccc(OC)cc5)c5ccc(OC)cc5)ccc4S3)c3cc(F)ccc3-c3cc(C(F)(F)F)nn32)cc1]
IA-27
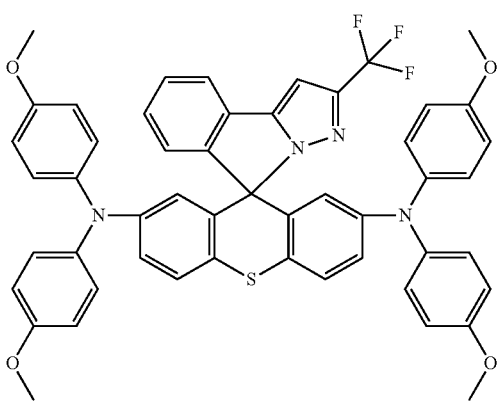 [SMILES: COc1ccc(N(c2ccc(OC)cc2)c2ccc3c(c2)C2(c4cc(N(c5ccc(OC)cc5)c5ccc(OC)cc5)ccc4S3)c3ccccc3-c3cc(C(F)(F)F)nn32)cc1]

-continued
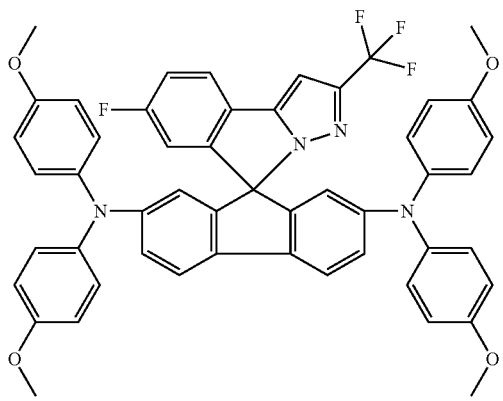 [SMILES: COc1ccc(N(c2ccc(OC)cc2)c2ccc3c(c2)C2(c4cc(N(c5ccc(OC)cc5)c5ccc(OC)cc5)ccc4-3)c3cc(F)ccc3-c3cc(C(F)(F)F)nn32)cc1]
IA-28
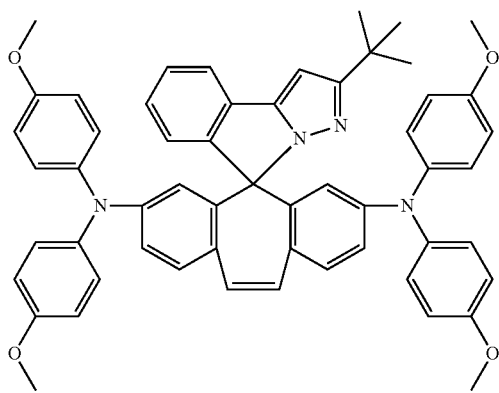 [SMILES: COc1ccc(N(c2ccc(OC)cc2)c2ccc3c(c2)C2(c4cc(N(c5ccc(OC)cc5)c5ccc(OC)cc5)ccc4C=C3)c3ccccc3-c3cc(C(C)(C)C)nn32)cc1]
IA-29
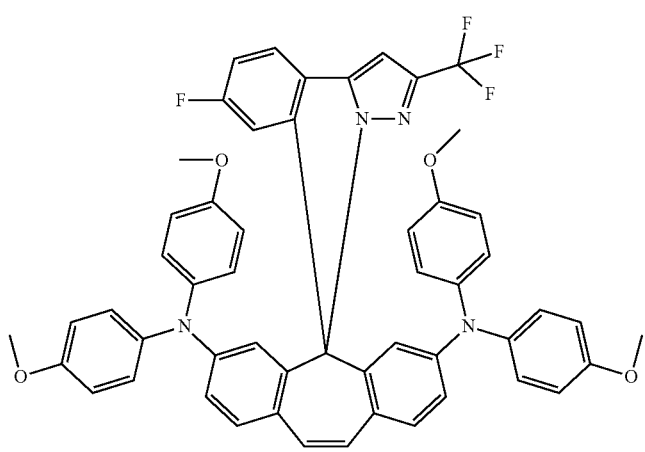
IA-30

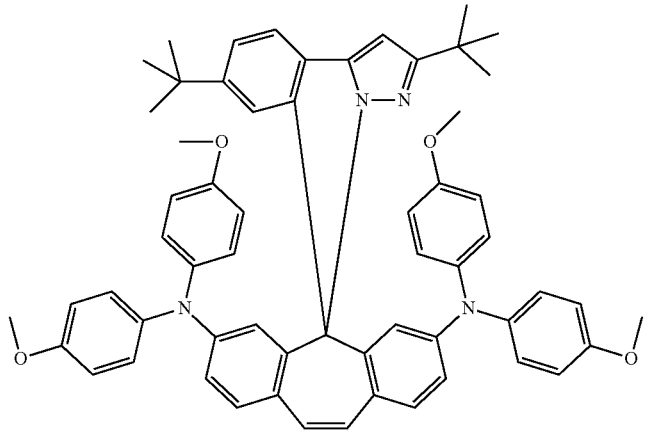

IA-31

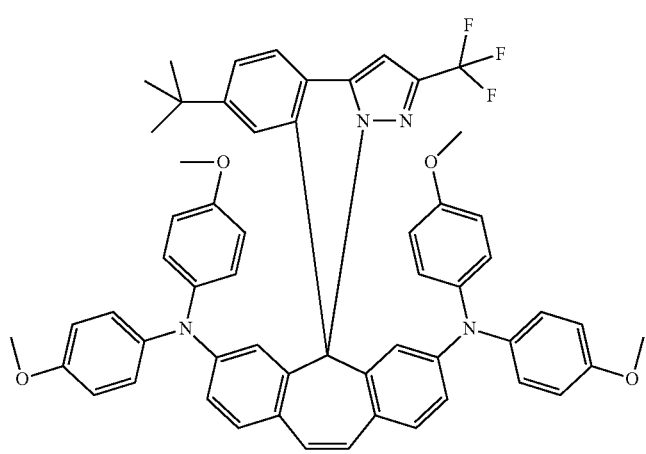

IA-32

4. The organic compound of claim 1, having a structure represented by formula (IA-b):

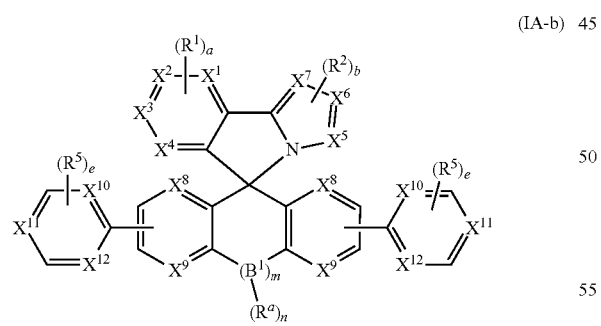

(IA-b)

wherein
$X^{10}$ to $X^{12}$ are each independently carbon or nitrogen;
each $X^{10}$ can be the same or different;
each $X^{11}$ can be the same or different;
each $X^{12}$ can be the same or different;
each of $R^5$'s is independently hydrogen, fluorine, $C_1$-$C_{12}$ alkyl, $C_1$-$C_6$ alkoxy or $C_6$-$C_{12}$ aryl;
e is an integer of 0 to 5; and
when e is equal to or greater than 1, each of $R^5$'s can be the same or different.

5. The organic compound of claim 4, having a structure represented by one of formula (IA-33) to formula (IA-46):

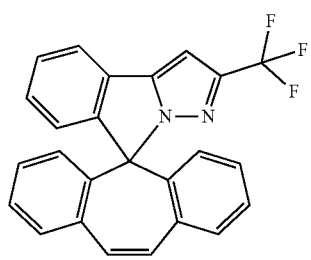 [SMILES: FC(F)(F)c1cc2n(n1)C1(c3ccccc3C=Cc3ccccc31)c1ccccc1-2]

IA-33

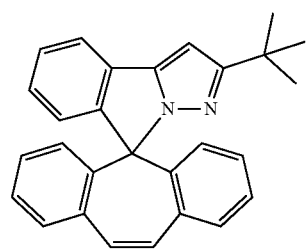 [SMILES: CC(C)(C)c1cc2n(n1)C1(c3ccccc3C=Cc3ccccc31)c1ccccc1-2]

IA-34

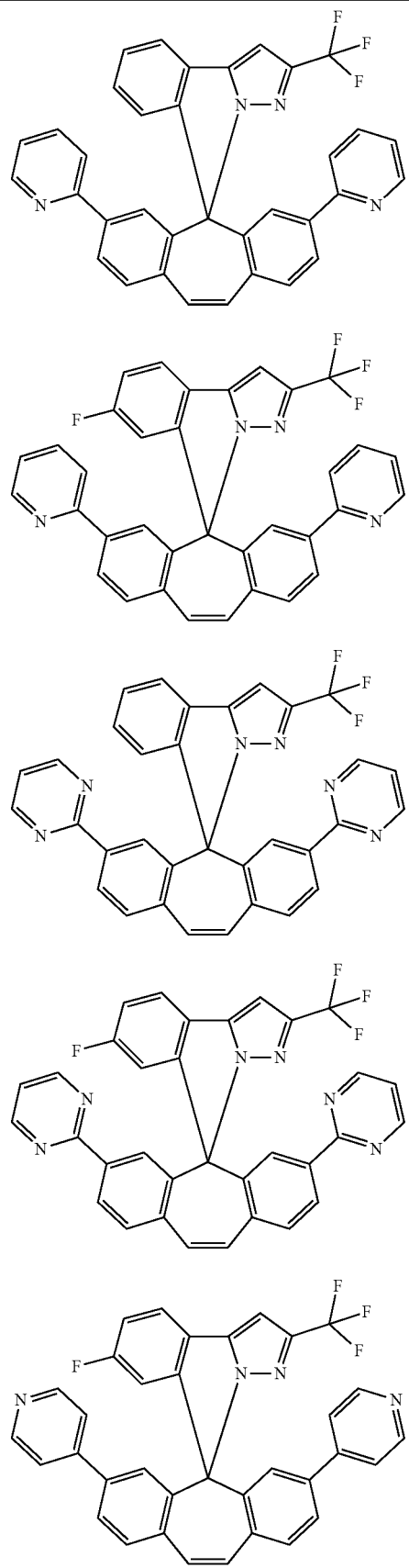
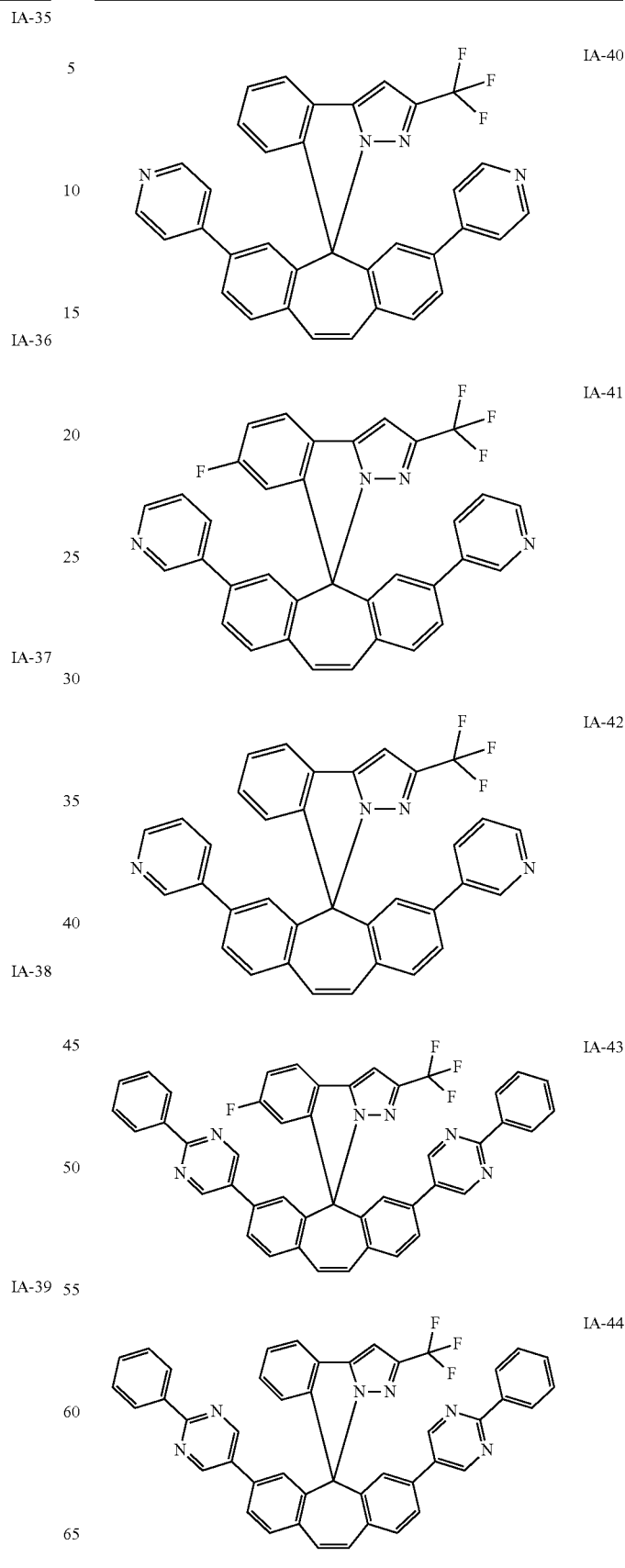

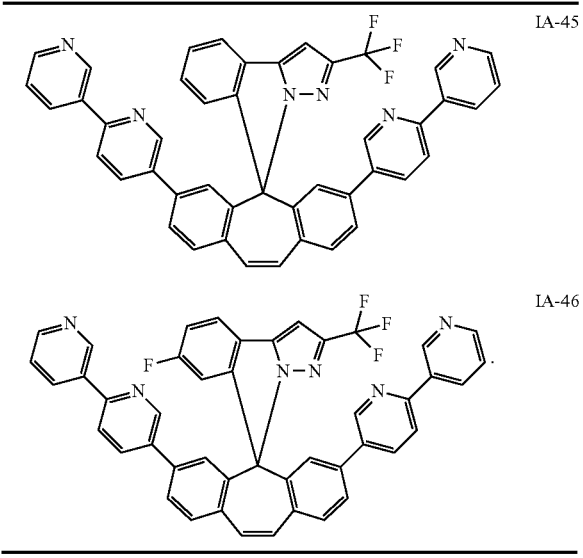

6. The organic compound of claim 1, having a structure represented by formula (IA-c):

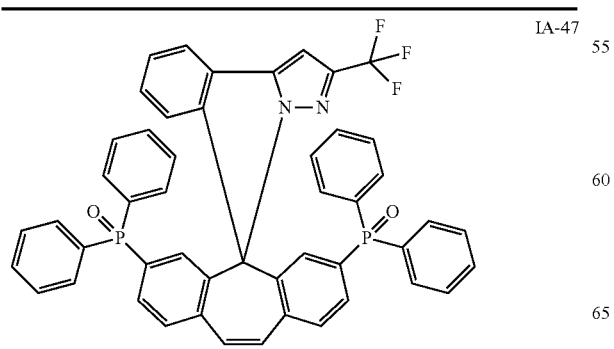

wherein
each of $R^6$'s is independently hydrogen, fluorine, $C_1$-$C_{12}$ alkyl, $C_1$-$C_6$ alkoxy or $C_6$-$C_{12}$ aryl;
f is an integer of 0 to 5; and
when f is equal to or greater than 1, each of $R^6$'s can be the same or different.

7. The organic compound of claim 6, having a structure represented by one of formula (IA-47) to formula (IA-48):

8. The organic compound of claim 1, wherein at least one of $X^1$ to $X^4$ is nitrogen.

9. The organic compound of claim 1, having a structure represented by one of formula (IA-49) to formula (IA-52):

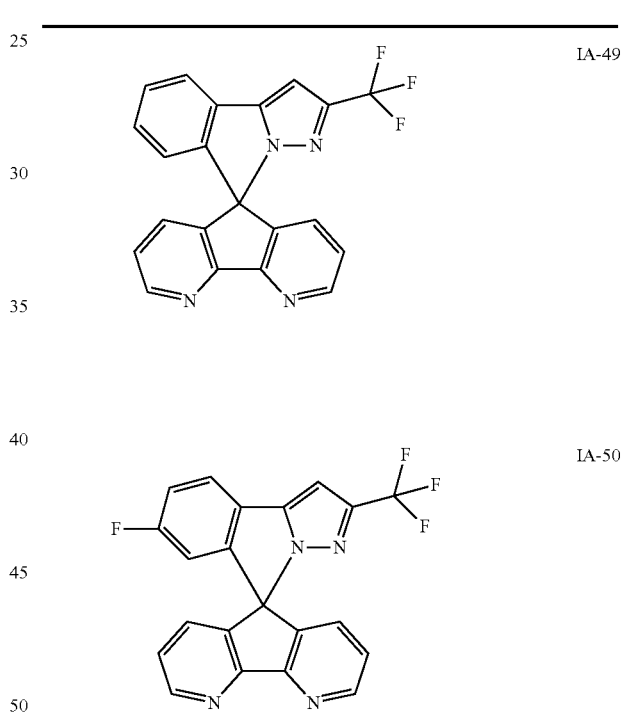

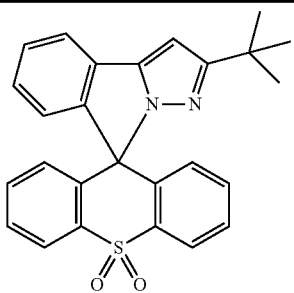
IA-52